(12) United States Patent
Nakamura et al.

(10) Patent No.: US 9,052,592 B2
(45) Date of Patent: Jun. 9, 2015

(54) RESIST COMPOSITION AND RESIST PATTERN FORMING METHOD

(71) Applicant: Tokyo Ohka Kogyo Co., Ltd., Kawasaki-shi (JP)

(72) Inventors: Tsuyoshi Nakamura, Kawasaki (JP); Kazuishi Tanno, Kawasaki (JP); Akiya Kawaue, Kawasaki (JP); Takayoshi Mori, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 0 days.

(21) Appl. No.: 14/218,249

(22) Filed: Mar. 18, 2014

(65) Prior Publication Data

US 2014/0287360 A1 Sep. 25, 2014

(30) Foreign Application Priority Data

Mar. 25, 2013 (JP) .................. 2013-062887

(51) Int. Cl.

| | | |
|---|---|---|
| *G03F 7/004* | (2006.01) | |
| *C08F 28/00* | (2006.01) | |
| *G03F 7/038* | (2006.01) | |
| *C08F 220/24* | (2006.01) | |
| *C08F 220/56* | (2006.01) | |
| *C08F 20/52* | (2006.01) | |
| *C07C 381/12* | (2006.01) | |

(52) U.S. Cl.
CPC .............. *G03F 7/038* (2013.01); *C08F 220/24* (2013.01); *C08F 220/56* (2013.01); *C08F 20/52* (2013.01); *C07C 381/12* (2013.01)

(58) Field of Classification Search
USPC ............ 430/270.1, 913, 914; 526/243, 307.2, 526/303.1
See application file for complete search history.

(56) References Cited

U.S. PATENT DOCUMENTS

| | | | |
|---|---|---|---|
| 6,949,325 | B2 | 9/2005 | Li et al. |
| 8,187,789 | B2 * | 5/2012 | Yonemura et al. ......... 430/270.1 |
| 2001/0049073 | A1 | 12/2001 | Hada et al. |
| 2002/0068235 | A1 * | 6/2002 | Fujita et al. ................... 430/192 |
| 2004/0110085 | A1 | 6/2004 | Iwai et al. |
| 2009/0197204 | A1 | 8/2009 | Shiono et al. |
| 2009/0226842 | A1 * | 9/2009 | Shimizu et al. ............. 430/281.1 |
| 2009/0317743 | A1 | 12/2009 | Shiono et al. |
| 2010/0196820 | A1 * | 8/2010 | Kawaue et al. ............. 430/270.1 |
| 2010/0285405 | A1 * | 11/2010 | Shimokawa et al. ....... 430/270.1 |
| 2010/0310985 | A1 | 12/2010 | Mori et al. |
| 2011/0014569 | A1 * | 1/2011 | Kasahara et al. .......... 430/270.1 |
| 2011/0053082 | A1 * | 3/2011 | Ichikawa et al. ........... 430/270.1 |
| 2011/0117499 | A1 | 5/2011 | Matsumiya et al. |
| 2012/0009527 | A1 * | 1/2012 | Hatakeyama et al. ........ 430/325 |
| 2012/0149916 | A1 | 6/2012 | Utsumi et al. |
| 2012/0171616 | A1 * | 7/2012 | Thackeray et al. ........ 430/285.1 |
| 2013/0095427 | A1 * | 4/2013 | Yahagi et al. ............... 430/285.1 |
| 2013/0115554 | A1 * | 5/2013 | Takaki et al. .............. 430/283.1 |
| 2013/0157201 | A1 * | 6/2013 | Takaki et al. ................. 430/325 |

FOREIGN PATENT DOCUMENTS

| | | | |
|---|---|---|---|
| JP | A-2000-206694 | | 7/2000 |
| JP | 2000310857 A | * | 11/2000 |
| JP | A-2003-241385 | | 8/2003 |
| JP | A-2005-336452 | | 12/2005 |
| JP | A-2006-063318 | | 3/2006 |
| JP | A-2006-259582 | | 9/2006 |
| JP | A-2006-317803 | | 11/2006 |
| JP | A-2009-025723 | | 2/2009 |
| JP | A-2010-002870 | | 1/2010 |
| JP | A-2010-032994 | | 2/2010 |
| JP | A-2010-277043 | | 12/2010 |
| JP | A-2011-013569 | | 1/2011 |
| JP | A-2011-128226 | | 6/2011 |

OTHER PUBLICATIONS

Iwamura et al, Hydrogen-Transfer Polymerization Behavior of N-Acylacrylamide, Journal of Polymer Science:Part A:Polymer Chemistry, vol. 38, pp. 430-435 (2000).*
Machine translation of JP 2000-310857 (no date).*

* cited by examiner

*Primary Examiner* — Amanda C Walke
(74) *Attorney, Agent, or Firm* — Knobbe Martens Olson & Bear LLP

(57) ABSTRACT

A resist composition contains a high-molecular weight compound which has a partial structure represented by a general formula (a0-r-1) and has a constituent unit represented by a general formula (a0-1). In the formula (a0-r-1), $Y^1$ represents a divalent linking group; each of $R^2$ and $R^3$ represents a group having 0 to 20 carbon atoms, which is not a fluorine atom, and either $R^2$ or $R^3$ may form a ring with $Y^1$; m represents an integer of 1 or more; and $M^{m+}$ represents an m-valent organic cation. In the formula (a0-1), R represents a hydrogen atom, an alkyl group, or a halogenated alkyl group; $Ya^{01}$ represents a single bond or a divalent linking group; $X^{01}$ represents a sulfur atom or an oxygen atom; and $Ra^{01}$ represents an optionally substituted cyclic group, chain alkyl group or chain alkenyl group.

15 Claims, No Drawings

RESIST COMPOSITION AND RESIST PATTERN FORMING METHOD

CROSS-REFERENCE TO RELATED APPLICATIONS

Priority is claimed on Japanese Patent Application No. 2013-062887, filed Mar. 25, 2013, the content of which is incorporated herein by reference.

BACKGROUND OF THE INVENTION

1. Field of the Invention

The present invention relates to a resist composition and a resist pattern forming method.

2. Background Art

In lithography techniques, for example, a process including forming a resist film formed of a resist material on a substrate, performing selective exposure on the resist film, and performing a development treatment, thereby forming a resist pattern having a predetermined shape on the resist film is performed. A resist material whose characteristics are changed so that the exposed areas of the resist film are dissolved in a developing solution is referred to as a positive type, and a resist material whose characteristics are changed so that the exposed areas are not dissolved in a developing solution is referred to as a negative type.

In recent years, in the manufacturing of semiconductor elements and liquid crystal display elements, advances in lithography technologies have led to rapid progress in the field of pattern miniaturization. In general, these miniaturization techniques involve shortening of the wavelength (increasing the energy) of the exposure light source. Specifically, ultraviolet rays represented by g-line or i-line have hitherto been used. But nowadays, KrF excimer lasers and ArF excimer lasers are starting to be introduced in mass production of semiconductors. In addition, investigations are also being conducted on EUV (extreme ultraviolet radiation), EB (electron beams), X-rays, and the like, which have a shorter wavelength (higher energy) than these excimer lasers.

The resist material is required to have lithography properties such as sensitivity to the exposure light source and resolution capable of reproducing patterns of minute dimensions.

As the resist material that satisfies such requirements, a chemically amplified resist composition containing a base material component which exhibits changed solubility in a developing solution by the action of an acid and an acid generator component that generates an acid upon exposure has been used.

For example, in the case where the developing solution is an alkali developing solution (alkali development process), a composition containing a resin component (base resin) exhibiting increased solubility in the alkali developing solution by the action of an acid and an acid generator component is generally used as a positive-type chemically amplified resist composition. When a resist film formed using such a resist composition is selectively exposed during the formation of a resist pattern, an acid is generated from the acid generator component in the exposed areas, the polarity of the base resin increases by the action of the acid, and thus the exposed areas become soluble in the alkali developing solution. Therefore, alkali development is performed to form a positive type pattern in which the unexposed areas remain as a pattern.

When such a chemically amplified resist composition is applied to a solvent development process using a developing solution (organic developing solution) containing an organic solvent, the solubility in an organic developing solution relatively decreases as the polarity of the base resin increases. Thus, the unexposed areas of the resist film are dissolved and removed by the organic developing solution and a negative type resist pattern in which the exposed areas remain as a pattern is formed. The solvent development process adapted to form a negative type resist pattern as described above is sometimes referred to as a negative type development process (see, for example, JP-A-2009-025723).

In general, the base resin used in the chemically amplified resist composition has plural kinds of constituent units for the purpose of enhancing lithography properties and the like.

For example, in the case of a resin component which exhibits increased solubility in an alkali developing solution by the action of an acid, a constituent unit including an acid decomposable group which is decomposed by the action of an acid generated from an acid generator to increase its polarity is used. In addition, a constituent unit including a lactone-containing cyclic group, a constituent unit including a polar group such as a hydroxyl group, and the like are used in combination (see, for example, JP-A-2003-241385).

Recently, a demand for a high-molecular weight compound which is useful as a base resin for a resist composition has increased with gradual progress in the field of pattern miniaturization.

JP-A-2006-063318 proposes a resist composition using a high-molecular weight compound having a constituent unit having an imide group in a side chain for the purpose of increasing resolution.

SUMMARY OF THE INVENTION

While lithography techniques advance and application fields thereof are expanded, enhancements of various lithography properties such as an increase of sensitivity and an improvement of roughness in the formation of a resist pattern are required. However, in the resist composition described in JP-A-2006-063318, it is particularly necessary to improve roughness of the resist pattern.

The invention is contrived in view of the circumstances, and an object thereof is to provide a resist composition which can form a resist pattern whose roughness is decreased, while maintaining good sensitivity.

According to a first aspect of the invention, there is provided a resist composition which generates an acid upon exposure and exhibits changed solubility in a developing solution by the action of the acid, including a partial structure represented by the following general formula (a0-r-1), and a base material component (A) which exhibits changed solubility in a developing solution by the action of an acid, in which the base material component (A) contains a high-molecular weight compound having a constituent unit (a0) represented by the following general formula (a0-1).

[Chemical formula 1]

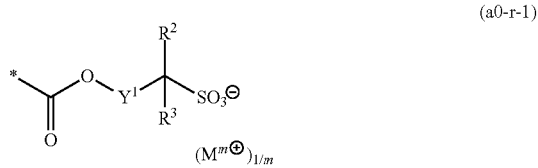

(a0-r-1)

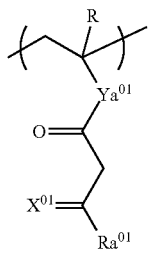

(a0-1)

In the formula (a0-r-1), $Y^1$ represents a divalent linking group; each of $R^2$ and $R^3$ independently represents a group having 0 to 20 carbon atoms, which is not a fluorine atom, and either $R^2$ or $R^3$ may form a ring with $Y^1$; m represents an integer of 1 or more; $M^{m+}$ represents an m-valent organic cation; and * represents a bond (and has the same usage below). In the formula (a0-1), R represents a hydrogen atom, an alkyl group having 1 to 5 carbon atoms, or a halogenated alkyl group having 1 to 5 carbon atoms; $Ya^{01}$ represents a single bond or a divalent linking group; $X^{01}$ represents a sulfur atom or an oxygen atom; and $Ra^{01}$ represents an optionally substituted cyclic group, an optionally substituted chain alkyl group, or an optionally substituted chain alkenyl group.

According to a second aspect of the invention, there is provided a resist pattern forming method including: forming a resist film on a support using the resist composition of the first aspect of the invention; exposing the resist film; and developing the resist film after the exposure to form a resist pattern.

According to a resist composition and a resist pattern forming method of the invention, it is possible to form a resist pattern whose roughness is decreased, while maintaining good sensitivity.

DETAILED DESCRIPTION OF THE INVENTION

In the present specification and claims, the term "aliphatic" is a relative concept used in relation to the term "aromatic" and defines a group or a compound each having no aromaticity.

The term "alkyl group" includes a linear, branched or cyclic, monovalent saturated hydrocarbon group, unless otherwise specified. The same applies for the alkyl group within an alkoxy group.

The term "alkylene group" includes a linear, branched or cyclic, divalent saturated hydrocarbon group, unless otherwise specified.

The term "halogenated alkyl group" refers to a group in which some or all hydrogen atoms of an alkyl group are substituted with a halogen atom. Examples of the halogen atom include a fluorine atom, a chlorine atom, a bromine atom, and an iodine atom.

The term "fluorinated alkyl group" or "fluorinated alkylene group" refers to a group in which some or all hydrogen atoms of an alkyl group or an alkylene group are substituted with a fluorine atom.

The term "constituent unit" means a monomer unit constituting a high-molecular weight compound (for example, a resin, a polymer, or a copolymer).

The case of describing "may have a substituent" or "optionally substituted" includes both of the case where the hydrogen atom (—H) is substituted with a monovalent group and the case where the methylene group (—$CH_2$—) is substituted with a divalent group.

The term "exposure" is a concept including irradiation with any form of radiation.

The term "constituent unit derived from an acrylic ester" means a constituent unit constituted upon cleavage of an ethylenic double bond of an acrylic ester.

The term "acrylic ester" refers to a compound in which a terminal hydrogen atom of a carboxy group of acrylic acid ($CH_2$=CH—COOH) is substituted with an organic group.

In the acrylic ester, a hydrogen atom bonded to a carbon atom at the α-position may be substituted with a substituent. The substituent ($R^{α0}$) with which the hydrogen atom bonded to the carbon atom at the α-position is substituted is an atom other than the hydrogen atom or a group, and examples thereof include an alkyl group having 1 to 5 carbon atoms and a halogenated alkyl group having 1 to 5 carbon atoms. In addition, examples of the acrylic ester also include an itaconic acid diester in which the substituent ($R^{α0}$) is substituted with an ester bond-containing substituent and an α-hydroxyacrylic ester in which the substituent ($R^{α0}$) is substituted with a hydroxyalkyl group or a group in which the hydroxyl group of the hydroxyalkyl group is modified. It is to be noted that the carbon atom at the α-position of the acrylic ester refers to a carbon atom to which the carbonyl group of acrylic acid is bonded, unless otherwise specified.

The acrylic ester in which the hydrogen atom bonded to the carbon atom at the α-position is substituted with a substituent is hereinafter sometimes referred to as "α-substituted acrylic ester". In addition, the acrylic ester and the α-substituted acrylic ester are sometimes referred to comprehensively as "(α-substituted) acrylic ester".

The term "constituent unit derived from acrylamide" means a constituent unit constituted upon cleavage of an ethylenic double bond of acrylamide.

In the acrylamide, the hydrogen atom bonded to the carbon atom at the α-position may be substituted with a substituent, and either one or both of the hydrogen atoms of the amino group of the acrylamide may be substituted with a substituent. It is to be noted that the carbon atom at the α-position of the acrylamide refers to a carbon atom to which the carbonyl group of the acrylamide is bonded, unless otherwise specified.

Examples of the substituent with which the hydrogen atom bonded to the carbon atom at the α-position of the acrylamide is substituted include those exemplified above as the substituent at the α-position (substituent ($R^{α0}$)) for the α-substituted acrylic ester.

The term "constituent unit derived from hydroxystyrene or a hydroxystyrene derivative" means a constituent unit constituted upon cleavage of an ethylenic double bond of hydroxystyrene or a hydroxystyrene derivative.

The term "hydroxystyrene derivative" is a concept including compounds in which the hydrogen atom at the α-position of hydroxystyrene is substituted with other substituent such as an alkyl group and a halogenated alkyl group, and derivatives thereof. Examples of such derivatives include those in which the hydrogen atom of the hydroxyl group of hydroxystyrene in which the hydrogen atom at the α-position may be substituted with a substituent is substituted with an organic group; and those in which a substituent other than the hydroxyl group is bonded to the benzene ring of hydroxystyrene in which the hydrogen atom at the α-position may be substituted with a substituent. It is to be noted that the term "α-position (carbon atom at the α-position)" refers to a carbon atom to which the benzene ring is bonded, unless otherwise specified.

Examples of the substituent with which the hydrogen atom at the α-position of hydroxystyrene is substituted include those exemplified above as the substituent at the α-position for the α-substituted acrylic ester.

The term "constituent unit derived from vinylbenzoic acid or a vinylbenzoic acid derivative" means a constituent unit constituted upon cleavage of an ethylenic double bond of vinylbenzoic acid or a vinylbenzoic acid derivative.

The term "vinylbenzoic acid derivative" is a concept including compounds in which the hydrogen atom at the α-position of vinylbenzoic acid is substituted with other substituent such as an alkyl group and a halogenated alkyl group, and derivatives thereof. Examples of such derivatives include those in which the hydrogen atom of the carboxy group of vinylbenzoic acid in which the hydrogen atom at the α-position may be substituted with a substituent is substituted with an organic group; and those in which a substituent other than a hydroxyl group and a carboxy group is bonded to the benzene ring of vinylbenzoic acid in which the hydrogen atom at the α-position may be substituted with a substituent. It is to be noted that the term "α-position (carbon atom at the α-position)" refers to a carbon atom to which the benzene ring is bonded, unless otherwise specified.

The term "styrene" is a concept including styrene and compounds in which the hydrogen atom at the α-position of styrene is substituted with other substituent such as an alkyl group and a halogenated alkyl group.

The term "constituent unit derived from styrene" or "constituent unit derived from a styrene derivative" means a constituent unit constituted upon cleavage of an ethylenic double bond of styrene or a styrene derivative.

The alkyl group as the substituent at the α-position is preferably a linear or branched alkyl group. Specifically, examples thereof include an alkyl group having 1 to 5 carbon atoms (for example, a methyl group, an ethyl group, a propyl group, an isopropyl group, an n-butyl group, an isobutyl group, a tert-butyl group, a pentyl group, an isopentyl group, or a neopentyl group).

In addition, specifically, examples of the halogenated alkyl group as the substituent at the α-position include a group in which some or all hydrogen atoms of the above-described "alkyl group as the substituent at the α-position" are substituted with a halogen atom. Examples of the halogen atom include a fluorine atom, a chlorine atom, a bromine atom, and an iodine atom, with a fluorine atom being especially preferable.

In addition, specifically, examples of the hydroxyalkyl group as the substituent at the α-position include a group in which some or all hydrogen atoms of the above-described "alkyl group as the substituent at the α-position" are substituted with a hydroxyl group. The number of the hydroxyl groups in the hydroxyalkyl group is preferably 1 to 5, and most preferably 1.

Resist Composition

A resist composition of a first aspect of the invention is a resist composition which generates an acid upon exposure and exhibits changed solubility in a developing solution by the action of the acid. The resist composition has a partial structure represented by a general formula (a0-r-1) therein and contains a base material component (A) (hereinafter, also referred to as "component (A)") which exhibits changed solubility in a developing solution by the action of an acid.

When a resist film is formed using such a resist composition and is selectively exposed, an acid is generated in the exposed areas of the resist film and the solubility of the component (A) in the developing solution changes by the action of the acid, whereas the solubility of the component (A) in the developing solution does not change in the unexposed areas of the resist film. Thus, a difference is caused between the exposed areas and the unexposed areas in solubility in the developing solution. Therefore, when the resist film is developed, the exposed areas are dissolved and removed and a positive type resist pattern is formed in the case where the resist composition is a positive type. In the case where the resist composition is a negative type, the unexposed areas are dissolved and removed and a negative type resist pattern is formed.

In the present specification, the resist composition which is used to form a positive type resist pattern by dissolving and removing exposed areas is referred to as a positive type resist composition, and the resist composition which is used to form a negative type resist pattern by dissolving and removing unexposed areas is referred to as a negative type resist composition.

The resist composition of this aspect may be a positive type resist composition, or a negative type resist composition.

In addition, the resist composition of this aspect may be for use in an alkali development process using an alkali developing solution in a development treatment when a resist pattern is formed, or in a solvent development process using a developing solution containing an organic solvent (organic developing solution) in the development treatment.

The resist composition of this aspect has acid generating ability to generate an acid upon exposure, and the acid may be generated upon exposure from the component (A) or an additive component blended separately from the component (A).

Specifically, the resist composition of this aspect may be:

(1) a composition which contains an acid generator component (B) which generates an acid upon exposure (hereinafter, referred to as "component (B)");

(2) a composition in which the component (A) generates an acid upon exposure; or (3) a composition in which the component (A) generates an acid upon exposure, and which further contains a component (B).

That is, in the cases of the above-described (2) and (3), the component (A) is a "base material component which generates an acid upon exposure and exhibits changed solubility in a developing solution by the action of the acid". When the component (A) is a base material component which generates an acid upon exposure and exhibits changed solubility in a developing solution by the action of the acid, a high-molecular weight compound having a constituent unit (a0) represented by a general formula (a0-1) to be described later is preferably a high-molecular weight compound which generates an acid upon exposure and exhibits changed solubility in a developing solution by the action of the acid. As such a high-molecular weight compound, a resin having a constituent unit which generates an acid upon exposure can be used. A constituent unit having a partial structure represented by the general formula (a0-r-1) or a known constituent unit can be used as the constituent unit which generates an acid upon exposure.

The resist composition of this aspect is preferably the composition described in (1).

Partial structure represented by general formula (a0-r-1)

The resist composition of this aspect has a partial structure represented by the following general formula (a0-r-1) therein.

The partial structure represented by the general formula (a0-r-1) may be included in the base material component (A)

blended with the resist composition, or may be included in a component other than the component (A).

In the resist composition, the anion moiety of the partial structure represented by the general formula (a0-r-1) becomes an appropriate weakly acidic anion upon exposure to exhibit a quenching (acid diffusion control) effect to thus trap the acid generated upon exposure. In the formation of a resist pattern, in exposed areas of a resist film, the partial structure is decomposed upon exposure to lose acid diffusion controlling properties (basicity), and thus the quenching effect is not exhibited. In unexposed areas of the resist film, the partial structure exhibits the quenching effect.

[Chemical formula 2]

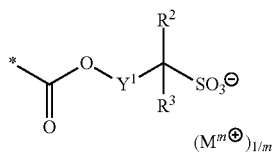

(a0-r-1)

In the formula, $Y^1$ represents a divalent linking group; each of $R^2$ and $R^3$ independently represents a group having 0 to 20 carbon atoms, which is not a fluorine atom, and either $R^2$ or $R^3$ may form a ring with $Y^1$; m represents an integer of 1 or more; and $M^{m+}$ represents an m-valent organic cation.

In the formula (a0-r-1), $Y^1$ represents a divalent linking group.

Preferred examples of the divalent linking group in $Y^1$ include an optionally substituted divalent hydrocarbon group and a hetero atom-containing divalent linking group.
Optionally Substituted Divalent Hydrocarbon Group:

When $Y^1$ represents an optionally substituted divalent hydrocarbon group, the hydrocarbon group may be an aliphatic hydrocarbon group or an aromatic hydrocarbon group.
Aliphatic Hydrocarbon Group in $Y^1$ The aliphatic hydrocarbon group means a hydrocarbon group having no aromaticity. The aliphatic hydrocarbon group may be either saturated or unsaturated, and in general, it is preferably saturated.

Examples of the aliphatic hydrocarbon group include a linear or branched aliphatic hydrocarbon group, and an aliphatic hydrocarbon group containing a ring in a structure thereof.
Linear or Branched Aliphatic Hydrocarbon Group The linear or branched aliphatic hydrocarbon group preferably has 1 to 10 carbon atoms, more preferably 1 to 8 carbon atoms, still more preferably 1 to 5 carbon atoms, and most preferably 1 to 3 carbon atoms.

The linear aliphatic hydrocarbon group is preferably a linear alkylene group, and specifically, examples thereof include a methylene group [—$CH_2$—], an ethylene group [—($CH_2$)$_2$—], r a trimethylene group [—($CH_2$)$_3$—], a tetramethylene group [—($CH_2$)$_4$—], and a pentamethylene group [—($CH_2$)$_5$—].

The branched aliphatic hydrocarbon group is preferably a branched alkylene group, and specifically, examples thereof include alkylalkylene groups, including alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)—, and —C($CH_2CH_3$)$_2$—; alkylethylene groups such as —CH($CH_3$)$CH_2$—, —CH($CH_3$)CH($CH_3$)—, —C($CH_3$)$_2CH_2$—, —CH($CH_2CH_3$)$CH_2$—, and —C($CH_2CH_3$)$_2$—$CH_2$—; alkyltrimethylene groups such as —CH($CH_3$)$CH_2CH_2$— and —$CH_2$CH($CH_3$)$CH_2$—; and alkyltetramethylene groups such as —CH($CH_3$)$CH_2CH_2CH_2$— and —$CH_2$CH($CH_3$)$CH_2CH_2$—. As the alkyl group in the alkylalkylene group, a linear alkyl group having 1 to 5 carbon atoms is preferable.

The linear or branched aliphatic hydrocarbon group may or may not have a substituent. Examples of the substituent include a fluorine atom, a fluorinated alkyl group having 1 to 5 carbon atoms, which is substituted with a fluorine atom, an alkoxy group having 1 to 10 carbon atoms, an alkoxyalkyl group having 2 to 15 carbon atoms, and a carbonyl group.
Aliphatic Hydrocarbon Group Containing Ring in Structure Thereof Examples of the aliphatic hydrocarbon group containing a ring in a structure thereof include an optionally substituted cyclic aliphatic hydrocarbon group containing a hetero atom in a ring structure thereof (a group in which two hydrogen atoms are eliminated from an aliphatic hydrocarbon ring), a group in which the cyclic aliphatic hydrocarbon group is bonded to the terminal of a linear or branched aliphatic hydrocarbon group, and a group in which the cyclic aliphatic hydrocarbon group intervenes on the way of a linear or branched aliphatic hydrocarbon group. Examples of the linear or branched aliphatic hydrocarbon group include the same groups as those described above.

The cyclic aliphatic hydrocarbon group has preferably 3 to 20 carbon atoms, and more preferably 3 to 12 carbon atoms.

The cyclic aliphatic hydrocarbon group may be either a polycyclic group or a monocyclic group. The monocyclic alicyclic hydrocarbon group is preferably a group in which two hydrogen atoms are eliminated from a monocycloalkane. The monocycloalkane is preferably one having 3 to 6 carbon atoms. Specifically, examples thereof include cyclopentane and cyclohexane. The polycyclic alicyclic hydrocarbon group is preferably a group in which two hydrogen atoms are eliminated from a polycycloalkane. The polycycloalkane preferably has 7 to 12 carbon atoms. Specifically, examples thereof include adamantane, norbornane, isobornane, tricyclodecane, tetracyclododecane, and tricyclotetradecane.

The cyclic aliphatic hydrocarbon group may or may not have a substituent. Examples of the substituent include an alkyl group, an alkoxy group, a halogen atom, a halogenated alkyl group, a hydroxyl group, and a carbonyl group.

The alkyl group as the substituent is preferably an alkyl group having 1 to 5 carbon atoms, and most preferably a methyl group, an ethyl group, a propyl group, an n-butyl group, or a tert-butyl group.

The alkoxy group as the substituent is preferably an alkoxy group having 1 to 5 carbon atoms, more preferably a methoxy group, an ethoxy group, an n-propoxy group, an isopropoxy group, an n-butoxy group, or a tert-butoxy group, and most preferably a methoxy group or an ethoxy group.

Examples of the halogen atom as the substituent include a fluorine atom, a chlorine atom, a bromine atom, and an iodine atom, with a fluorine atom being preferable.

Examples of the halogenated alkyl group as the substituent include a group in which some or all the hydrogen atoms of the above-described alkyl group are substituted with the above-described halogen atom.

In the cyclic aliphatic hydrocarbon group, some of the carbon atoms constituting the ring structure thereof may be substituted with a substituent containing a hetero atom. The substituent containing a hetero atom is preferably —O—, —C(=O)—O—, —S—, —S(=O)$_2$—, or —S(=O)$_2$—O—.

Aromatic Hydrocarbon Group in $Y^1$

The aromatic hydrocarbon group is a hydrocarbon group having at least one aromatic ring.

This aromatic ring is not particularly limited so long as it is a cyclic conjugated system having (4n+2) π electrons, and it may be either monocyclic or polycyclic. The number of carbon atoms of the aromatic ring is preferably 5 to 30, more preferably 5 to 20, still more preferably 6 to 15, and especially preferably 6 to 12. However, the number of carbon atoms does not include the number of carbon atoms in the substituent. Specifically, examples of the aromatic ring include an aromatic hydrocarbon ring such as benzene, naphthalene, anthracene, and phenanthrene; and an aromatic heterocyclic ring in which some of the carbon atoms constituting the above-described aromatic hydrocarbon ring are substituted with a hetero atom. Examples of the hetero atom in the aromatic heterocyclic ring include an oxygen atom, a sulfur atom, and a nitrogen atom. Specifically, examples of the aromatic heterocyclic ring include a pyridine ring and a thiophene ring.

Specifically, examples of the aromatic hydrocarbon group include a group in which two hydrogen atoms are eliminated from the above-described aromatic hydrocarbon ring or aromatic heterocyclic ring (an arylene group or a heteroarylene group); a group in which two hydrogen atoms are eliminated from an aromatic compound containing two or more aromatic rings (for example, biphenyl or fluorene); and a group in which one hydrogen atom of a group in which one hydrogen atom is eliminated from the above-described aromatic hydrocarbon ring or aromatic heterocyclic ring (an aryl group or a heteroaryl group) is substituted with an alkylene group (for example, a group in which one hydrogen atom is further eliminated from an aryl group in an arylalkyl group such as a benzyl group, a phenethyl group, a 1-naphthylmethyl group, a 2-naphthylmethyl group, a 1-naphthylethyl group, and a 2-naphthylethyl group). The number of carbon atoms of the alkylene group bonded to the above-described aryl group or heteroaryl group is preferably 1 to 4, more preferably 1 to 2, and especially preferably 1.

In the above-described aromatic hydrocarbon group, the hydrogen atom(s) which the aromatic hydrocarbon group has may be substituted with a substituent. For example, the hydrogen atom(s) bonded to the aromatic ring in the aromatic hydrocarbon group may be substituted with a substituent. Examples of the substituent include an alkyl group, an alkoxy group, a halogen atom, a halogenated alkyl group, and a hydroxyl group.

The alkyl group as the substituent is preferably an alkyl group having 1 to 5 carbon atoms. The alkyl group is most preferably a methyl group, an ethyl group, a propyl group, an n-butyl group, or a tert-butyl group.

Examples of the alkoxy group, the halogen atom, and the halogenated alkyl group as the substituent include those exemplified above for the substituent with which the hydrogen atom(s) which the cyclic aliphatic hydrocarbon group has is substituted.

Hetero Atom-Containing Divalent Linking Group:

When $Y^1$ represents a hetero atom-containing divalent linking group, preferred examples of the linking group include —O—, —C(=O)—O—, —C(=O)—, —O—C(=O)—O—, —C(=O)—NH—, —NH—, —NH—C(=NH)— (H may be substituted with a substituent such as an alkyl group and an acyl group), —S—, —S(=O)$_2$—, —S(=O)$_2$—O—, and a group represented by a general formula: —$Y^{21}$—O—$Y^{22}$—, —$Y^{21}$—O—, —$Y^{21}$—C(=O)—O—, —C(=O)—O—$Y^{21}$—, —[$Y^{21}$—C(=O)—O]$_{m''}$—$Y^{22}$—, —$Y^{21}$—O—C(=O)—$Y^{22}$—, or —$Y^{21}$—S(=O)$_2$—O—$Y^{22}$—. In the formulae, each of $Y^{21}$ and $Y^{22}$ independently represents an optionally substituted divalent hydrocarbon group, 0 represents an oxygen atom, and m" represents an integer of 0 to 3.

When the hetero atom-containing divalent linking group is —C(=O)—NH—, —C(=O)—NH—C(=O)—, —NH—, or —NH—C(=NH)—, H may be substituted with a substituent such as an alkyl group and an acyl group. The number of carbon atoms of the substituent (such as an alkyl group and an acyl group) is preferably 1 to 10, more preferably 1 to 8, and especially preferably 1 to 5.

In the general formula: —$Y^{21}$—O—$Y^{22}$—, —$Y^{21}$—O—, —$Y^{21}$—C(=O)—O—, —C(=O)—O—$Y^{21}$—, —[$Y^{21}$—C(=O)—O]$_{m''}$—$Y^{22}$—, —$Y^{21}$—O—C(=O)—$Y^{22}$—, or —$Y^{21}$—S(=O)$_2$—O—$Y^{22}$—, each of $Y^{21}$ and $Y^{22}$ independently represents an optionally substituted divalent hydrocarbon group. Examples of the divalent hydrocarbon group include the same divalent hydrocarbon groups as those exemplified above for the divalent linking group (optionally substituted divalent hydrocarbon group).

$Y^{21}$ is preferably a linear aliphatic hydrocarbon group, more preferably a linear alkylene group, still more preferably a linear alkylene group having 1 to 5 carbon atoms, and especially preferably a methylene group or an ethylene group.

$Y^{22}$ is preferably a linear or branched aliphatic hydrocarbon group, and more preferably a methylene group, an ethylene group, or an alkylmethylene group. The alkyl group in the alkylmethylene group is preferably a linear alkyl group having 1 to 5 carbon atoms, more preferably a linear alkyl group having 1 to 3 carbon atoms, and most preferably a methyl group.

In the group represented by the formula: —[$Y^{21}$—C(=O)—O]$_{m''}$—$Y^{22}$—, m" represents an integer of 0 to 3, preferably an integer of 0 to 2, more preferably 0 or 1, and especially preferably 1. Namely, the group represented by the formula: —[$Y^{21}$—C(=O)—O]$_{m''}$—$Y^{22}$— is especially preferably a group represented by the formula: —$Y^{21}$—C(=O)—O—$Y^{22}$—. Above all, a group represented by the formula: —(CH$_2$)$_{a'}$—C(=O)—O—(CH$_2$)$_{b'}$— is preferable. In the foregoing formula, a' represents an integer of 1 to 10, preferably an integer of 1 to 8, more preferably an integer of 1 to 5, still more preferably 1 or 2, and most preferably 1. b' represents an integer of 1 to 10, preferably 1 to 8, more preferably 1 to 5, still more preferably 1 or 2, and most preferably 1.

In the resist composition of this aspect, excluding the case in which $Y^1$ forms a ring with either $R^2$ or $R^3$ to be described later, $Y^1$ in the formula (a0-r-1) is preferably an optionally substituted divalent hydrocarbon group, more preferably an optionally substituted divalent aliphatic hydrocarbon group, still more preferably an optionally substituted linear or branched aliphatic hydrocarbon group, and especially preferably an optionally substituted linear or branched alkylene group having 1 to 5 carbon atoms.

In the formula (a0-r-1), each of $R^2$ and $R^3$ independently represents a group having 0 to 20 carbon atoms, which is not a fluorine atom, and either $R^2$ or $R^3$ may form a ring with Y. When $R^2$ and $R^3$ are not fluorine atoms, the anion moiety of the partial structure represented by the formula (a0-r-1) can become an appropriate weakly acidic anion.

Examples of the group having 0 to 20 carbon atoms which is represented by $R^2$ and $R^3$ include a hydrogen atom, an alkyl group (preferably having 1 to 20 carbon atoms, more preferably 1 to 12 carbon atoms, and especially preferably 1 to 8 carbon atoms, and examples thereof include a methyl group, an ethyl group, an i-propyl group, a t-butyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, and a nonadecyl group), an alkenyl group (preferably having 2 to 20 carbon atoms, more preferably 2 to 12 carbon atoms, and especially preferably 2 to 8 carbon atoms, and examples thereof include a vinyl group, an allyl group, a 2-butenyl group, and a 3-pentenyl group), an alkynyl group (preferably having 2 to 20 carbon atoms, more preferably 2 to 12 carbon atoms, and especially preferably 2 to 8 carbon atoms, and examples thereof include a propargyl group and a 3-pentynyl group), an aryl group (preferably having 6 to 30 carbon atoms, more preferably 6 to 20 carbon atoms, and especially preferably 6 to 12 carbon atoms, and examples thereof include a phenyl group, a p-methylphenyl group, and a naphthyl group), a substituted or unsubstituted amino group (preferably having 0 to 20 carbon atoms, more preferably 0 to 10 carbon atoms, and especially preferably 0 to 6 carbon atoms, and examples thereof include an amino group, a methylamino group, a dimethylamino group, a diethylamino group, and a dibenzylamino group), an alkoxy group (preferably having 1 to 20 carbon atoms, more preferably 1 to 12 carbon atoms, and especially preferably 1 to 8 carbon atoms, and examples thereof include a methoxy group, an ethoxy group, and a butoxy group), an aryloxy group (preferably having 6 to 20 carbon atoms, more preferably 6 to 16 carbon atoms, and especially preferably 6 to 12 carbon atoms, and examples thereof include a phenyloxy group and a 2-naphthyloxy group), an acyl group (preferably having 1 to 20 carbon atoms, more preferably 1 to 16 carbon atoms, and especially preferably 1 to 12 carbon atoms, and examples thereof include an acetyl group, a benzoyl group, a formyl group, and a pivaloyl group), an alkoxycarbonyl group (preferably having 2 to 20 carbon atoms, more preferably 2 to 16 carbon atoms, and especially preferably 7 to 12 carbon atoms, and examples thereof include a methoxycarbonyl group and an ethoxycarbonyl group), an aryloxycarbonyl group (preferably having 7 to 20 carbon atoms, more preferably 7 to 16 carbon atoms, and especially preferably 7 to 10 carbon atoms, and examples thereof include a phenyloxycarbonyl group), an acyloxy group (preferably having 2 to 20 carbon atoms, more preferably 2 to 16 carbon atoms, and especially preferably 2 to 10 carbon atoms, and examples thereof include an acetoxy group and a benzoyloxy group), an acylamino group (preferably having 2 to 20 carbon atoms, more preferably 2 to 16 carbon atoms, and especially preferably 2 to 10 carbon atoms, and examples thereof include an acetylamino group and a benzoylamino group), an alkoxycarbonylamino group (preferably having 2 to 20 carbon atoms, more preferably 2 to 16 carbon atoms, and especially preferably 2 to 12 carbon atoms, and examples thereof include a methoxycarbonylamino group), an aryloxycarbonylamino group (preferably having 7 to 20 carbon atoms, more preferably 7 to 16 carbon atoms, and especially preferably 7 to 12 carbon atoms, and examples thereof include a phenyloxycarbonylamino group), a sulfonylamino group (preferably having 1 to 20 carbon atoms, more preferably 1 to 16 carbon atoms, and especially preferably 1 to 12 carbon atoms, and examples thereof include a methanesulfonylamino group and a benzenesulfonylamino group), a hydroxy group, a mercapto group, a chlorine atom, a bromine atom, an iodine atom, a cyano group, a sulfo group, a carboxyl group, a nitro group, a hydroxamic acid group, a sulfino group, a hydrazino group, an imino group, a heterocyclic group (preferably having 1 to 30 carbon atoms, and more preferably 1 to 12 carbon atoms, in which the hetero atom is, for example, a nitrogen atom, an oxygen atom or a sulfur atom, concretely including imidazolyl, pyridyl, quinolyl, furyl, piperidyl, morpholino, benzoxazolyl, benzimidazolyl, and benzothiazolyl), and a silyl group (preferably having 3 to 40 carbon atoms, more preferably 3 to 30 carbon atoms, and especially preferably 3 to 24 carbon atom, and examples thereof include trimethylsilyl and triphenylsilyl).

In addition, when either $R^2$ or $R^3$ is an alkyl group (preferably, a methyl group), one hydrogen atom of the alkyl group may be substituted with —C(=O)—O—$R^{11}$ or —O—C(=O)—$R^{11}$ ($R^{11}$ represents an optionally substituted hydrocarbon group having 4 to 20 carbon atoms and is the same as $R^1$ in a formula (d1-1) to be described later).

When either $R^2$ or $R^3$ is a cyclic hydrocarbon group, it may be either an aliphatic group or an aromatic group. In addition, it may be either a polycyclic group or a monocyclic group.

The monocyclic alicyclic hydrocarbon group is preferably a group in which one hydrogen atom is eliminated from a monocycloalkane. As the monocycloalkane, a group having 3 to 8 carbon atoms, and preferably 4 to 8 carbon atoms is exemplified. Specifically, examples thereof include cyclopropane, cyclopentane, cyclohexane, and cyclooctane.

The polycyclic alicyclic hydrocarbon group is preferably a group in which one hydrogen atom is eliminated from a polycycloalkane. The polycycloalkane is preferably a group having 7 to 12 carbon atoms. Specifically, examples thereof include adamantane, norbornane, isobornane, tricyclodecane, and tetracyclododecane.

In addition, in the resist composition of this aspect, the alicyclic hydrocarbon group in $R^2$ and $R^3$ may contain a hetero atom in a ring structure thereof. Examples of the substituent containing the hetero atom include —O—, —C(=O)—O—, —S—, —S(=O)$_2$—, and —S(=O)$_2$—O—. Specific examples of such an alicyclic hydrocarbon group containing a hetero atom in a ring structure thereof include groups represented by general formulae (a2-r-1) to (a2-r-7), (a5-r-1) to (a5-r-4), and (ax3-r-1) to (ax3-r-3) to be described later, respectively, and preferred examples thereof include groups represented by formulae (r-lc-1-1), (r-lc-1-2), (r-lc-2-1), (r-lc-2-7), (r-lc-6-1), (r-lc-7-1), (r-sl-1-1), and (r-sl-1-18), respectively.

In the alicyclic hydrocarbon group in $R^2$ and $R^3$, some of hydrogen atoms bonded to the carbon atoms constituting the ring structure thereof may be substituted with a substituent. Examples of the substituent include an alkoxy group, a hydroxyl group, and an oxygen atom (=O).

The alkoxy group as the substituent preferably has an alkyl group having 1 to 5 carbon atoms. The alkyl group is especially preferably a methyl group, an ethyl group, a propyl group, an n-butyl group, or a tert-butyl group.

In the formula (a0-r-1), when either $R^2$ or $R^3$ forms a ring with $Y^1$, examples of the group represented by the following formula (a0-r-2), which is a part of the formula (a0-r-1), include any of groups represented by the following formulae (a0-r-21) to (a0-r-24), respectively.

[Chemical formula 3]

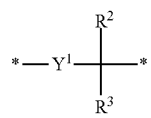

(a0-r-2)

-continued

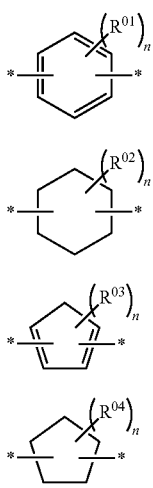

(a0-r-21)

(a0-r-22)

(a0-r-23)

(a0-r-24)

In the formulae, $Y^1$, $R^2$, and $R^3$ are the same as $Y^1$, $R^2$, and $R^3$ in the formula (a0-r-1); $R^{01}$ to $R^{04}$ represent an optionally substituted alkyl group having 1 to 10 carbon atoms; and n represents an integer of 0 to 2.

Examples of the optionally substituted alkyl group having 1 to 10 carbon atoms in $R^{01}$ to $R^{04}$ include a methyl group, an ethyl group, an i-propyl group, a t-butyl group, an n-octyl group, an n-decyl group, an n-hexadecyl group, a cyclopropyl group, a cyclopentyl group, and a cyclohexyl group. A substituent which $R^{01}$ to $R^{04}$ may have may be associated with any of a case in which the hydrogen atom (—H) in the alkyl group represented by $R^{01}$ to $R^{04}$ is substituted with a monovalent group and a case in which the methylene group (—$CH_2$—) in the alkyl group is substituted with a divalent group. Examples of the substituent include an imino group, an amino group, a hydroxy group, a mercapto group, a halogen atom (for example, a chlorine atom, a bromine atom, and an iodine atom), an oxygen atom (—O—), a cyano group, a sulfo group, a carboxyl group, and a nitro group.

Among these, each of $R^2$ and $R^3$ is preferably a hydrogen atom or a methyl group, and more preferably a hydrogen atom. Both $R^2$ and $R^3$ are especially preferably a hydrogen atom.

Specific examples of the anion moiety of the partial structure represented by the general formula (a0-r-1) are given below.

[Chemical formula 4]

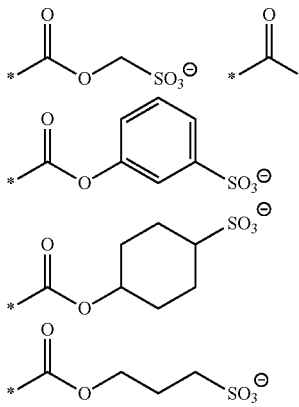

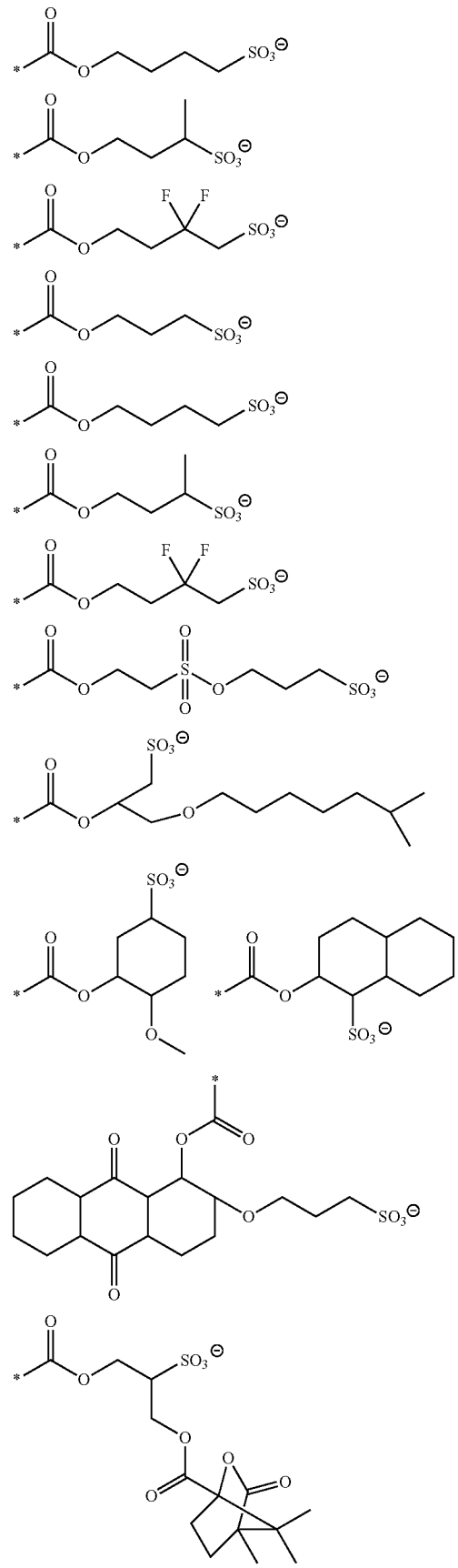

-continued

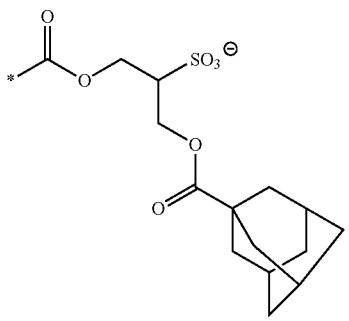

[Chemical formula 5]

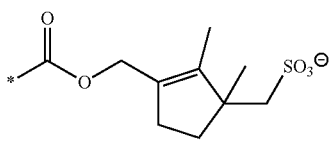

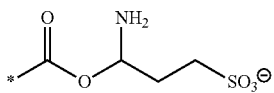

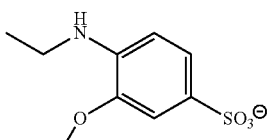

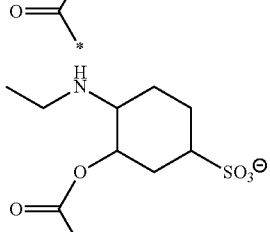

In the formula (a0-r-1), m represents an integer of 1 or more; and $M^{m+}$ represents an m-valent organic cation.

Examples of the organic cation represented by $M^{m+}$ include an onium cation, and preferred examples thereof include a sulfonium cation and an iodonium cation.

Specifically, preferred examples of the organic cation represented by $M^{m+}$ include organic cations represented by the following general formulae (ca-1) to (ca-4), respectively.

[Chemical formula 6]

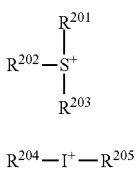
(ca-1)

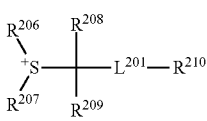
(ca-2)

(ca-3)

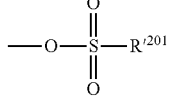

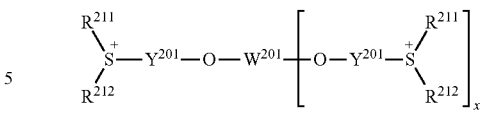
(ca-4)

In the formulae, each of $R^{201}$ to $R^{207}$, $R^{211}$, and $R^{212}$ independently represents an optionally substituted aryl group, alkyl group or alkenyl group, and $R^{201}$ to $R^{203}$, $R^{206}$ to $R^{207}$, or $R^{211}$ to $R^{212}$ may be bonded to each other to form a ring together with a sulfur atom in each formula; each of $R^{208}$ and $R^{209}$ independently represents a hydrogen atom or an alkyl group having 1 to 5 carbon atoms; $R^{210}$ represents an optionally substituted aryl group, alkyl group or alkenyl group, or an —$SO_2$—-containing cyclic group; $L^{201}$ represents —C(=O)— or —C(=O)—O—; each $Y^{201}$ independently represents an arylene group, an alkylene group, or an alkenylene group; x represents 1 or 2; and $W^{201}$ represents an (x+1)-valent linking group.

Examples of the aryl group in $R^{201}$ to $R^{207}$, $R^{211}$ and $R^{212}$ include an unsubstituted aryl group having 6 to 20 carbon atoms, and the aryl group is preferably a phenyl group or a naphthyl group.

The alkyl group in $R^{201}$ to $R^{207}$, $R^{211}$, and $R^{212}$ is preferably a chain or cyclic alkyl group having 1 to 30 carbon atoms.

The alkenyl group in $R^{201}$ to $R^{207}$, $R^{211}$, and $R^{212}$ is preferably an alkenyl group having 2 to 10 carbon atoms.

Examples of the substituent which each of $R^{201}$ to $R^{207}$ and $R^{210}$ to $R^{212}$ may have include an alkyl group, a halogen atom, a halogenated alkyl group, a carbonyl group, a cyano group, an amino group, an aryl group, and groups represented by the following formulae (a0-r-1) to (ca-r-7), respectively.

[Chemical formula 7]

—O—$R'^{201}$ [ca-r-1]

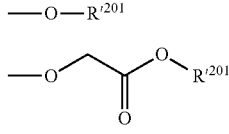 [ca-r-2]

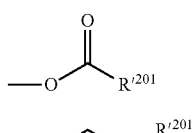 [ca-r-3]

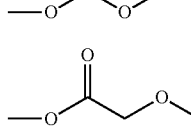 [ca-r-4]

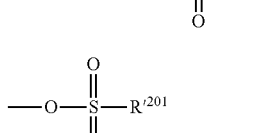 [ca-r-5]

—O—S(=O)(=O)—$R'^{201}$ [ca-r-6]

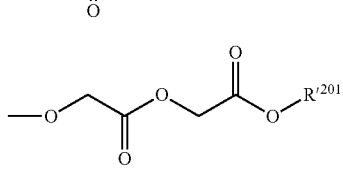 [ca-r-7]

In the formulae, each $R'^{201}$ independently represents a hydrogen atom or an optionally substituted cyclic group, chain alkyl group or chain alkenyl group.

Examples of the optionally substituted cyclic group, the optionally substituted chain alkyl group, or the optionally substituted chain alkenyl group represented by $R'^{201}$ include the same groups as those in $Ra^{01}$ in the formula (a0-1) to be described later. Besides, examples of the optionally substituted cyclic group or the optionally substituted chain alkyl group include the same acid dissociable group represented by a formula (a1-r-2) to be described later.

In the case where $R^{201}$ to $R^{203}$, $R^{206}$ to $R^{207}$, or $R^{211}$ to $R^{212}$ may be bonded to each other to form a ring together with a sulfur atom in each formula, they may be bonded to each other via a hetero atom such as a sulfur atom, an oxygen atom, and a nitrogen atom, or a functional group such as a carbonyl group, —SO—, —SO$_2$—, —SO$_3$—, —COO—, —CONH—, and —N($R_N$)— ($R_N$ represents an alkyl group having 1 to 5 carbon atoms). As for the ring to be formed, one ring containing a sulfur atom in the formula in a ring skeleton thereof is preferably a 3- to 10-membered ring, and especially preferably a 5- to 7-membered ring including the sulfur atom. Specific examples of the ring to be formed include a thiophene ring, a thiazole ring, a benzothiophene ring, a thianthrene ring, a benzothiophene ring, a dibenzothiophene ring, a 9H-thioxanthene ring, a thioxanthone ring, a phenoxathiin ring, a tetrahydrothiophenium ring, and a tetrahydrothiopyranium ring.

Each of $R^{208}$ and $R^{209}$ independently represents a hydrogen atom or an alkyl group having 1 to 5 carbon atoms. Of these, a hydrogen atom or an alkyl group having 1 to 3 carbon atoms is preferable. In the case where each of $R^{208}$ and $R^{209}$ is an alkyl group, they may be bonded to each other to form a ring.

$R^{210}$ represents an optionally substituted aryl group, an optionally substituted alkyl group, an optionally substituted alkenyl group, or an optionally substituted —SO$_2$—-containing cyclic group.

Examples of the aryl group in $R^{210}$ include an unsubstituted aryl group having 6 to 20 carbon atoms. Above all, a phenyl group or a naphthyl group is preferable.

Examples of the alkyl group in $R^{210}$ include a chain or cyclic alkyl group. Above all, an alkyl group having 1 to 30 carbon atoms is preferable.

The number of carbon atoms of the alkenyl group in $R^{210}$ is preferably 2 to 10.

Examples of the optionally substituted —SO$_2$—-containing cyclic group in $R^{210}$ include the same —SO$_2$—-containing cyclic groups as those exemplified above for the "—SO$_2$—-containing cyclic group" represented by $Ra^{21}$ in a general formula (a2-1) to be described later. Above all, the group represented by the general formula (a5-r-1) to be described later is preferable.

Each $Y^{201}$ independently represents an arylene group, an alkylene group, or an alkenylene group.

Examples of the arylene group in $Y^{201}$ include a group in which one hydrogen atom is eliminated from an aryl group exemplified for the aromatic hydrocarbon group in $Ra^{01}$ in the foregoing formula (a0-1).

Examples of the alkylene group and the alkenylene group in $Y^{201}$ include the same groups as those exemplified for the aliphatic hydrocarbon groups as the divalent hydrocarbon group in $Va^1$ in a general formula (a1-1) to be described later.

In the formula (ca-4), x is 1 or 2.

$W^{201}$ represents an (x+1)-valent (i.e., divalent or trivalent) linking group.

The divalent linking group in $W^{201}$ is preferably an optionally substituted divalent hydrocarbon group, and examples thereof include the same hydrocarbon groups as those exemplified for $Ya^{21}$ in the general formula (a2-1) to be described later. The divalent linking group in $W^{201}$ may be linear, branched, or cyclic, and it is preferably cyclic. Above all, a group in which two carbonyl groups are combined at the both ends of an arylene group is preferable. Examples of the arylene group include a phenylene group and a naphthylene group, with a phenylene group being especially preferable.

Examples of the trivalent linking group in $W^{201}$ include a group in which one hydrogen atom is eliminated from the above-described divalent linking group in $W^{201}$ and a group in which the above-described divalent linking group is further bonded to the above-described divalent linking group. The trivalent linking group in $W^{201}$ is preferably a group in which two carbonyl groups are bonded to an arylene group.

Specifically, preferred examples of the cation represented by the formula (ca-1) include cations represented by the following formulae (ca-1-1) to (ca-1-67), respectively.

[Chemical formula 8]

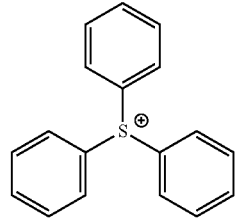

(ca-1-1)

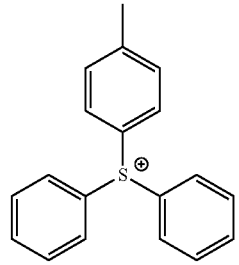

(ca-1-2)

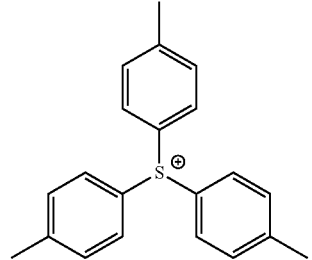

(ca-1-3)

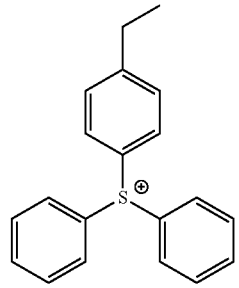

(ca-1-4)

(ca-1-5)
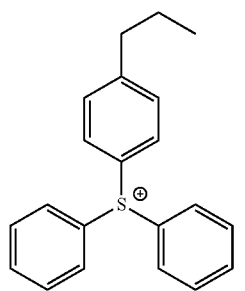
(ca-1-6)
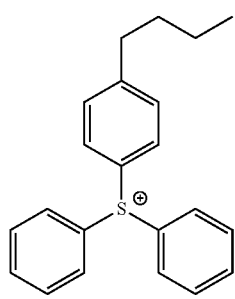
(ca-1-7)
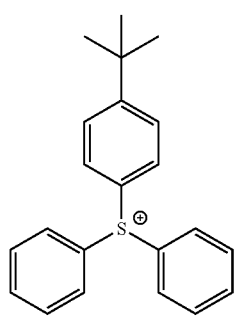
(ca-1-8)
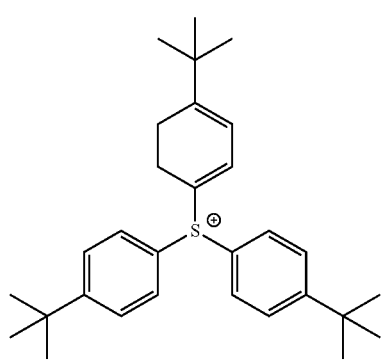
(ca-1-9)
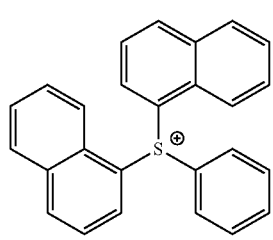
(ca-1-10)
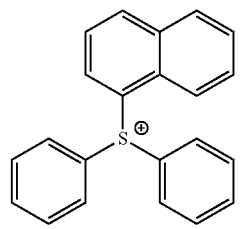
(ca-1-11)
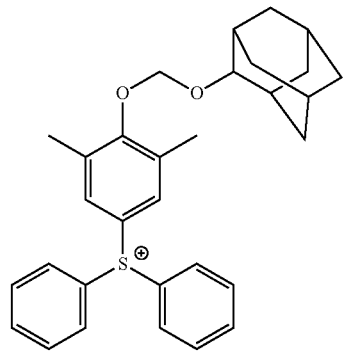
(ca-1-12)
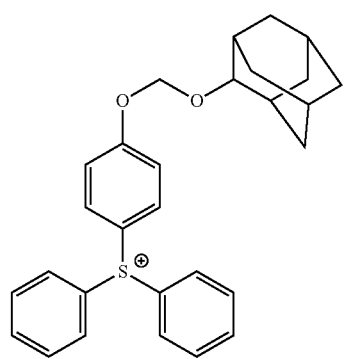
(ca-1-13)
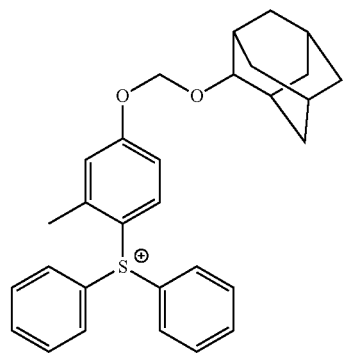
(ca-1-14)
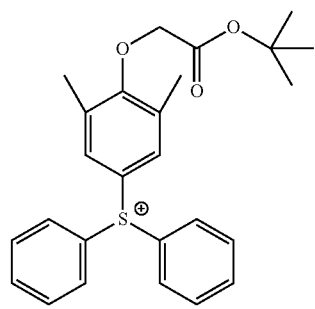

(ca-1-15)
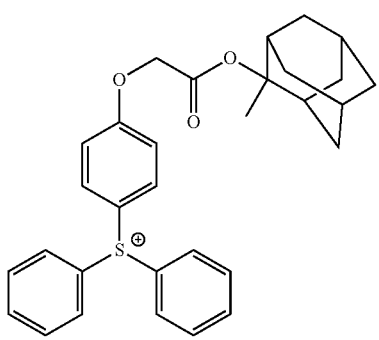
(ca-1-16)
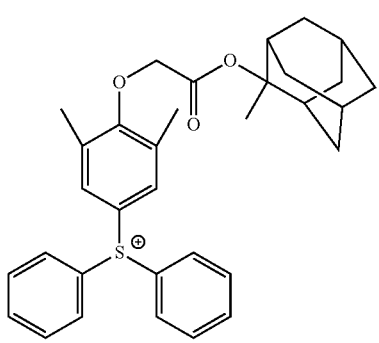
[Chemical formula 9]
(ca-1-17)
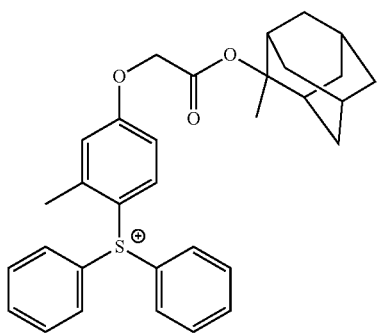
(ca-1-18)
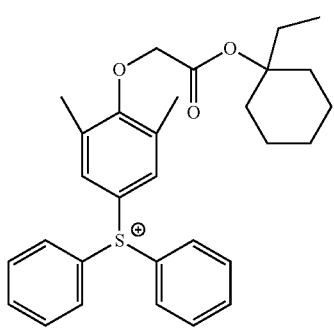
(ca-1-19)
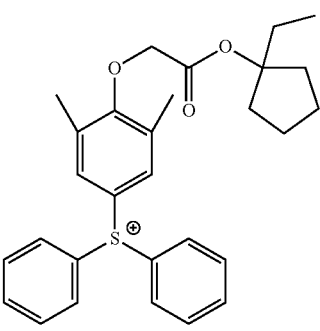
(ca-1-20)
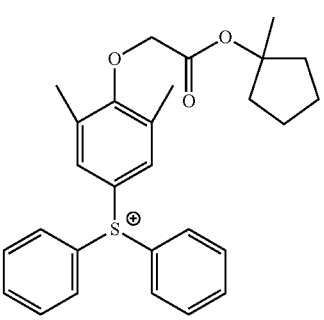
(ca-1-21)
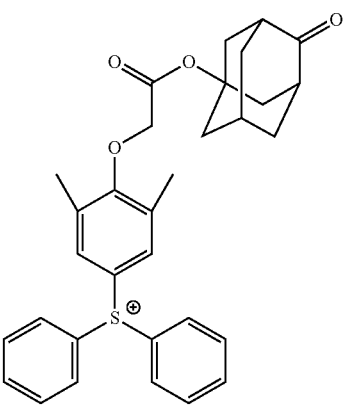
(ca-1-22)
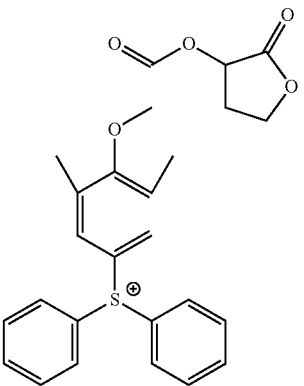

(ca-1-23)
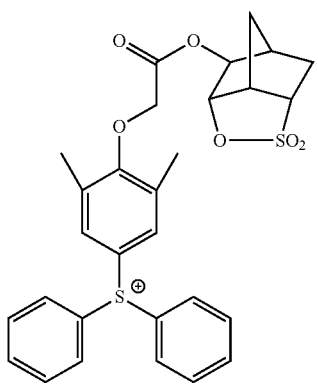
(ca-1-24)
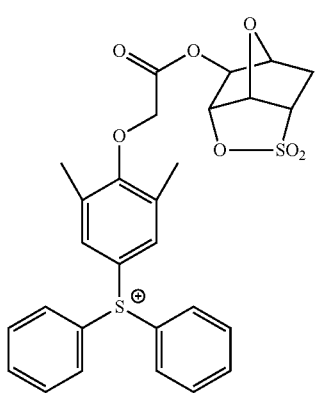
(ca-1-25)
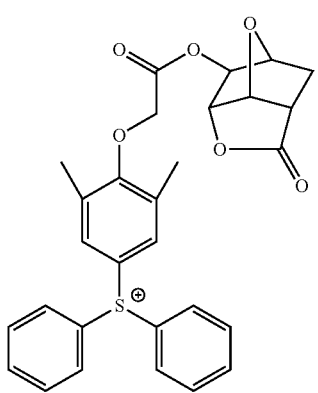
(ca-1-26)
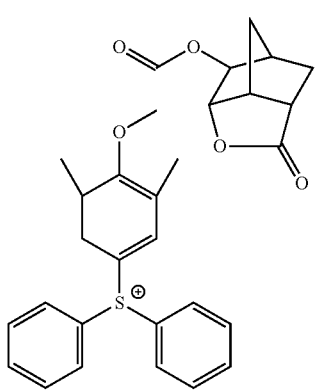
(ca-1-27)
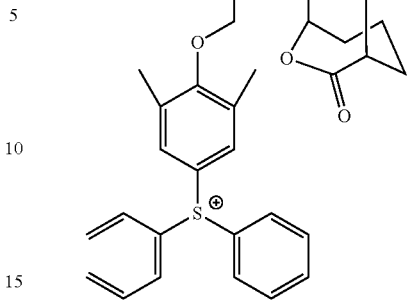
(ca-1-28)
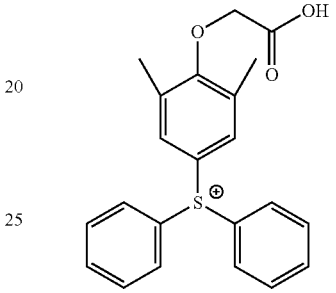
(ca-1-29)
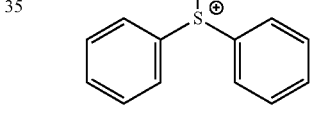
(ca-1-30)
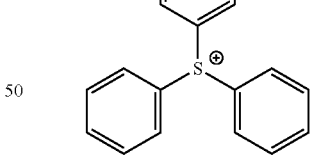
(ca-1-31)
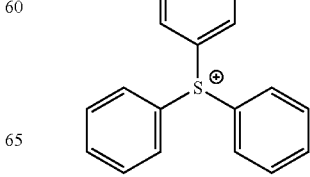

(ca-1-32) 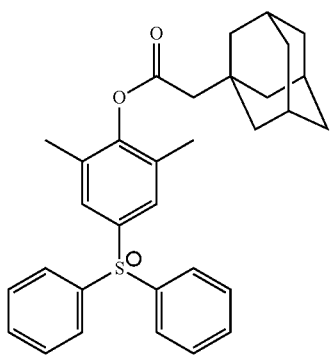
(ca-1-33) 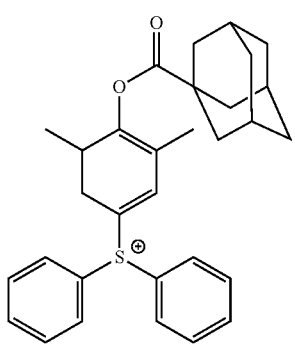
[Chemical formula 10]
(ca-1-34) 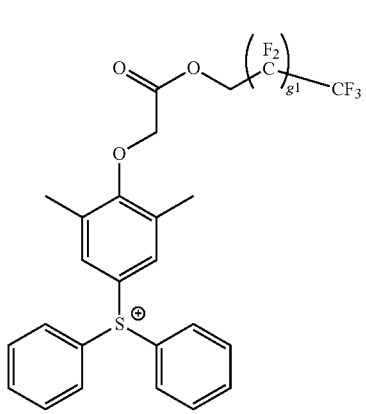
(ca-1-35) 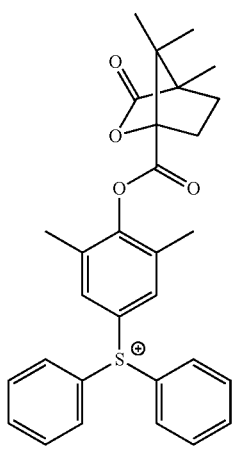
(ca-1-36) 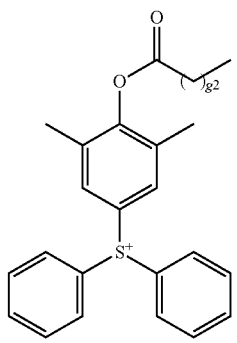
(ca-1-37) 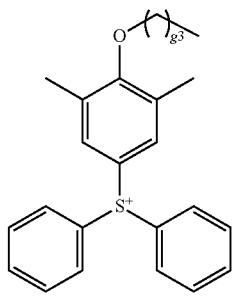
(ca-1-38) 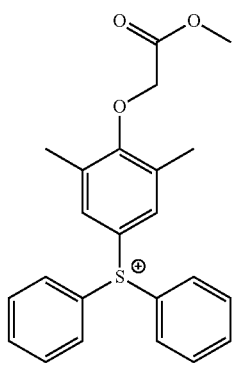
(ca-1-39) 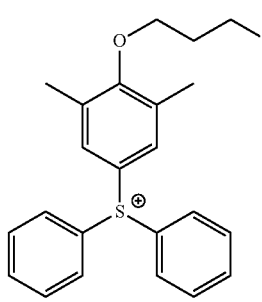

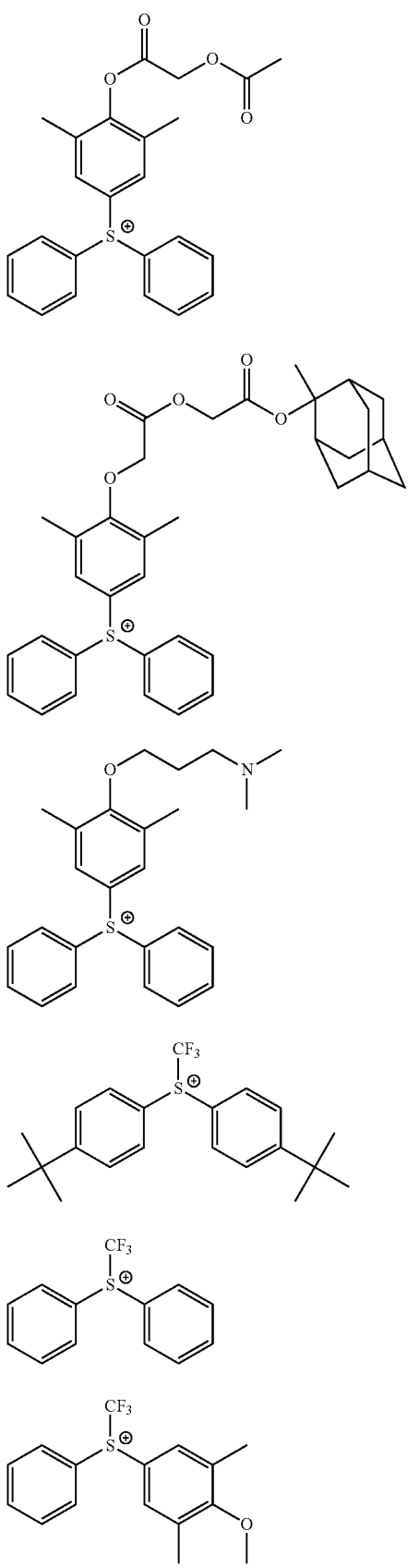
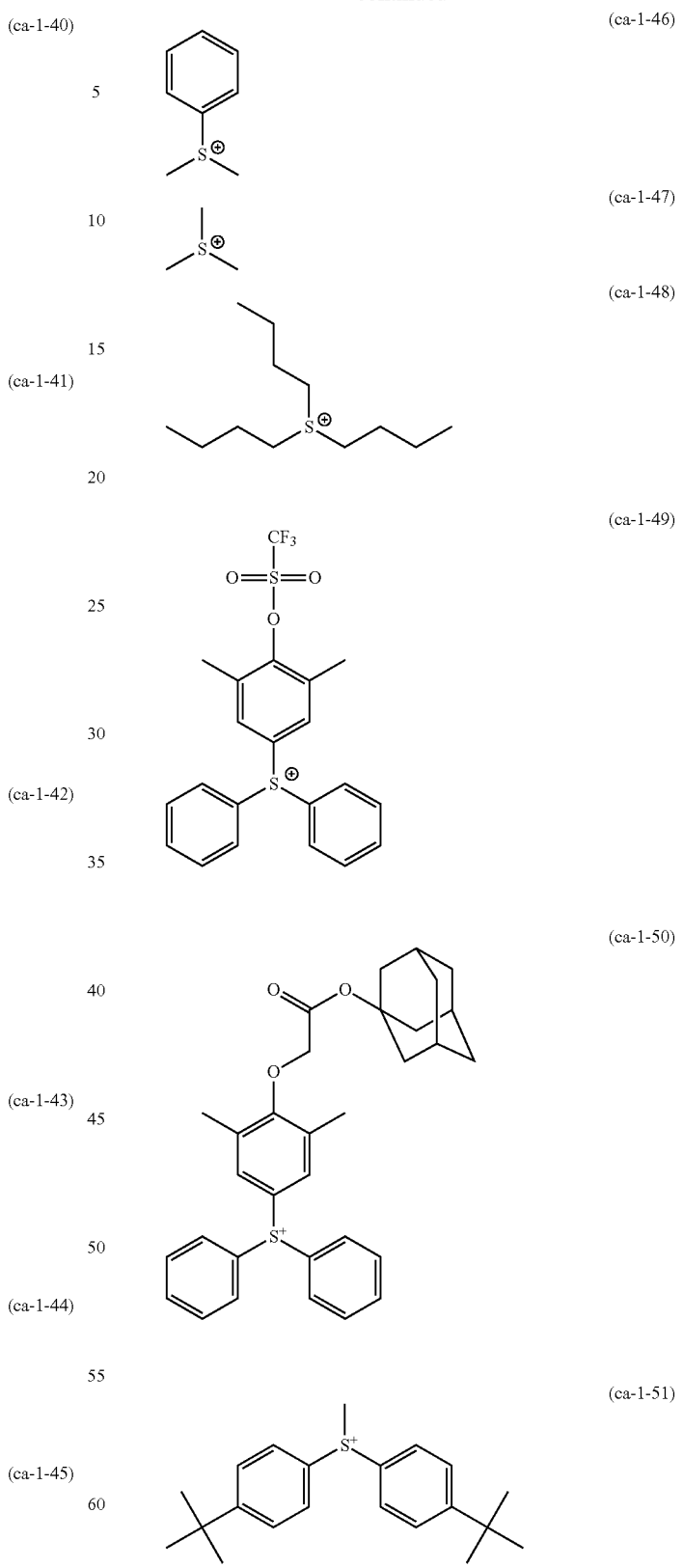
In the formulae, each of g1, g2, and g3 represents a repeating number; g1 represents an integer of 1 to 5; g2 represents an integer of 0 to 20; and g3 represents an integer of 0 to 20.

[Chemical formula 11]
(ca-1-52)
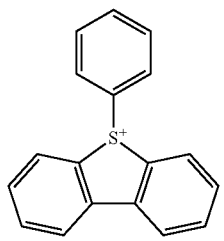
(ca-1-53)
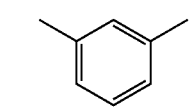
(ca-1-54)
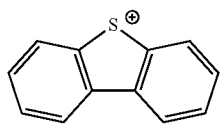
(ca-1-55)
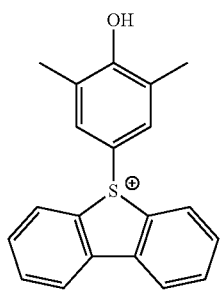
(ca-1-56)
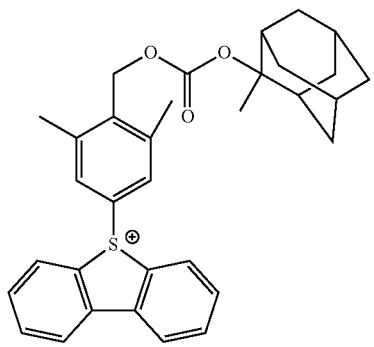
(ca-1-57)
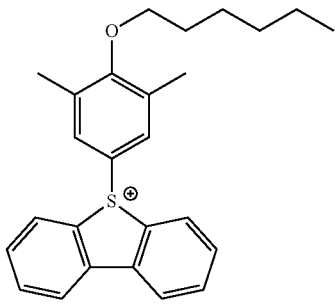
(ca-1-58)
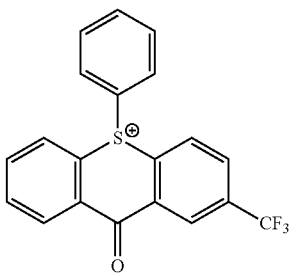
(ca-1-59)
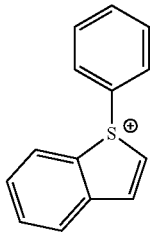
(ca-1-60)
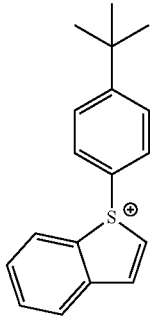
(ca-1-61)

(ca-1-62)
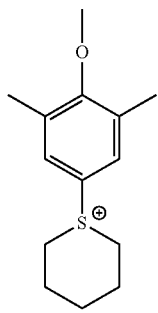

(ca-1-63)
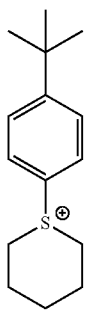

(ca-1-64)
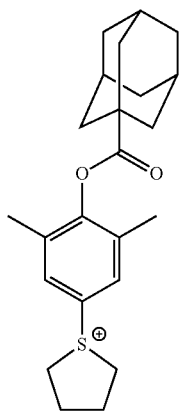

(ca-1-65)
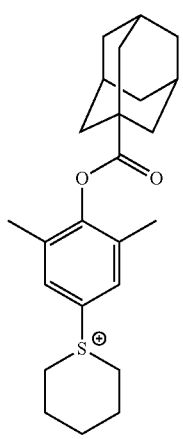

(ca-1-66)
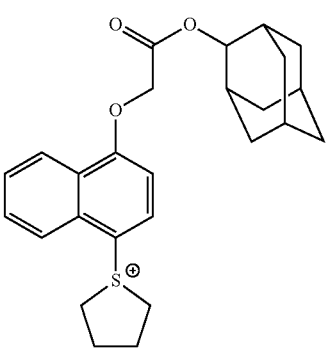

(ca-1-67)
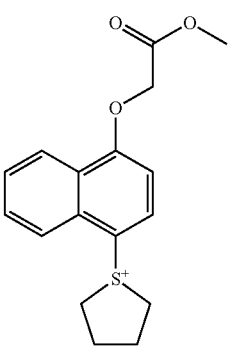

In the formulae, $R''^{201}$ represents a hydrogen atom or a substituent, and examples of the substituent include the same substituents as those exemplified above for the substituent which each of $R^{201}$ to $R^{207}$ and $R^{210}$ to $R^{212}$ may have.

Specifically, preferred examples of the cation represented by the formula (ca-2) include a diphenyl iodonium cation and a bis(4-tert-butylphenyl)iodonium cation.

Specifically, preferred examples of the cation represented by the formula (ca-3) include cations represented by the following formulae (ca-3-1) to (ca-3-6), respectively.

[Chemical formula 12]

(ca-3-1)
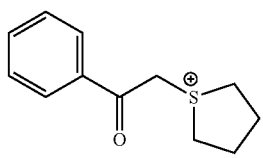

(ca-3-2)
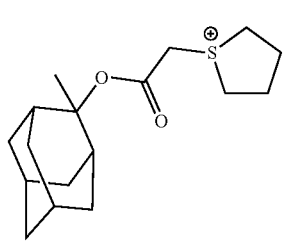

(ca-3-3)
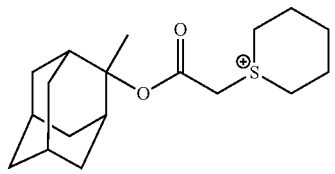

-continued

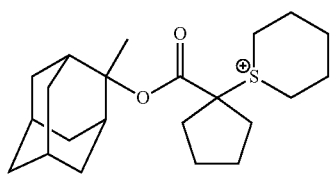
(ca-3-4)

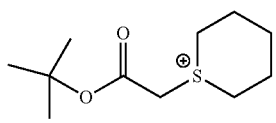
(ca-3-5)

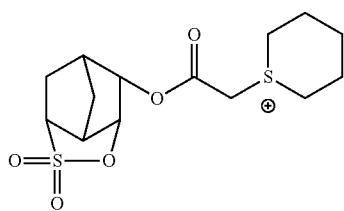
(ca-3-6)

Specifically, preferred examples of the cation represented by the formula (ca-4) include cations represented by the following formulae (ca-4-1) and (ca-4-2), respectively.

[Chemical formula 13]

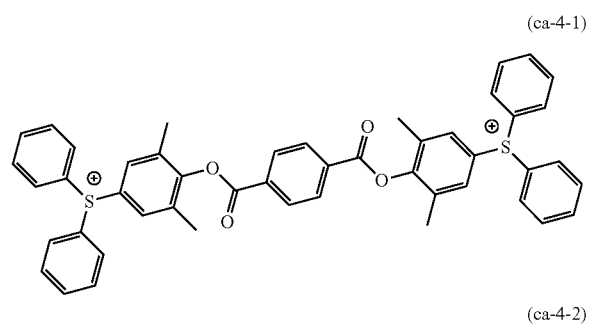
(ca-4-1)

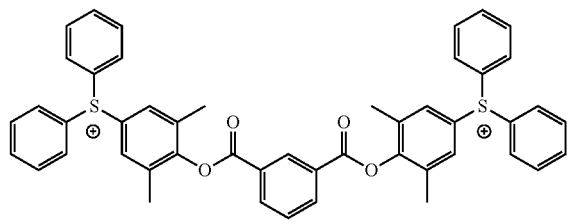
(ca-4-2)

Component A: Base Material Component

The component (A) is a base material component which exhibits changed solubility in a developing solution by the action of an acid.

In the invention, the term "base material component" refers to an organic compound having film-forming ability and an organic compound preferably having a molecular weight of 500 or more is used. When the molecular weight of the organic compound is 500 or more, the film-forming ability is improved and a nano-level resist pattern is easily formed.

The organic compound which is used as the base material component is roughly classified into a non-polymerized material and a polymer.

In general, the non-polymerized material has a molecular weight of 500 to less than 4,000. Hereinafter, the term "low-molecular weight compound" refers to a non-polymerized material having a molecular weight of 500 to less than 4,000.

In general, the polymer has a molecular weight of 1,000 or more. Hereinafter, the term "resin" or "high-molecular weight compound" refers to a polymer having a molecular weight of 1,000 or more.

A mass average molecular weight as converted into polystyrene by means of gel permeation chromatography (GPC) is employed for the molecular weight of the polymer.

When the resist composition of this aspect is a "negative type resist composition for use in an alkali development process" which is used to form a negative type resist pattern in the alkali development process, or a "positive type resist composition for use in a solvent development process" which is used to form a positive type resist pattern in the solvent development process, a base material component (A-2) (hereinafter, referred to as "component (A-2)") which is soluble in an alkali developing solution is preferably used as the component (A), and a crosslinking agent component is blended therewith. In such a resist composition, when an acid is generated from the component (B) upon exposure, crosslinking occurs between the component (A-2) and the crosslinking agent component by the action of the acid, and as a result, the solubility in the alkali developing solution decreases (the solubility in an organic developing solution increases). Therefore, in the formation of a resist pattern, when a resist film obtained by applying the resist composition to a support is selectively exposed, the exposed areas change to have sparingly soluble properties in the alkali developing solution (to have soluble properties in the organic developing solution), whereas the unexposed areas do not change in the state where they are still soluble in the alkali developing solution (sparingly soluble in the organic developing solution). Thus, a negative type resist pattern is formed by developing with the alkali developing solution. In addition, at this time, a positive type resist pattern is formed by developing with the organic developing solution.

As the component (A-2), a resin which is soluble in an alkali developing solution (hereinafter, referred to as "alkali-soluble resin") is used.

Examples of the alkali-soluble resin include a resin having a unit derived from at least one of α-(hydroxyalkyl)acrylic acid and an alkyl ester of α-(hydroxyalkyl)acrylic acid (preferably an alkyl ester having 1 to 5 carbon atoms), as disclosed in JP-A-2000-206694; an acrylic resin or a polycycloolefin resin which has a sulfonamide group and may have a hydrogen atom bonded to a carbon atom at the α-position substituted with a substituent, as disclosed in U.S. Pat. No. 6,949,325; an acrylic resin which contains a fluorinated alcohol and may have a hydrogen atom bonded to a carbon atom at the α-position substituted with a substituent, as disclosed in U.S. Pat. No. 6,949,325, JP-A-2005-336452, and JP-A-2006-317803; and a polycycloolefin resin having a fluorinated alcohol, as disclosed in JP-A-2006-259582. These resins are preferable in that a good resist pattern having little swelling can be formed.

The α-(hydroxyalkyl)acrylic acid represents one or both of acrylic acid in which a hydrogen atom is bonded to a carbon atom at the α-position having a carboxyl group bonded thereto, and α-hydroxyalkylacrylic acid in which a hydroxyalkyl group (preferably a hydroxyalkyl group having 1 to 5 carbon atoms) is bonded to the carbon atom at the α-position among acrylic acids which may have a hydrogen atom bonded to a carbon atom at the α-position substituted with a substituent.

As the crosslinking agent component, for example, an amino-based crosslinking agent such as glycoluril having a methylol group or an alkoxymethyl group, or a melamine-based crosslinking agent is preferable, in general, as it enables formation of a good resist pattern having little swelling. The blending amount of the crosslinking agent is preferably 1 part by mass to 50 parts by weight, relative to 100 parts by mass of the alkali-soluble resin.

When the resist composition of this aspect is a "positive type resist composition for use in an alkali development process" which is used to form a positive type resist pattern in the alkali development process, or a "negative type resist composition for use in a solvent development process" which is used to form a negative type resist pattern in the solvent development process, a base material component (A-1) (hereinafter, referred to as "component (A-1)") whose polarity increases by the action of an acid is preferably used as the component (A). Using the component (A-1), the polarity of the base material component changes before and after exposure, and thus a satisfactory development contrast can be obtained not only in the alkali development process, but also in the solvent development process.

In the case of applying an alkali development process, the component (A-1) is sparingly soluble in an alkali developing solution before exposure, but when an acid is generated upon exposure, the action of the acid causes an increase in polarity, thereby increasing the solubility in the alkali developing solution. Therefore, in the formation of a resist pattern, by performing selective exposure of a resist film obtained by applying the resist composition to a support, the exposed areas change to have soluble properties from sparingly soluble properties in the alkali developing solution, whereas the unexposed areas do not change in the state where they are still sparingly alkali-soluble, and hence, a positive type resist pattern is formed by alkali developing.

Meanwhile, in the case of applying a solvent development process, the component (A-1) exhibits high solubility in an organic developing solution before exposure, and when an acid is generated upon exposure, the polarity increases by the action of the acid, thereby decreasing the solubility in the organic developing solution. Therefore, in the formation of a resist pattern, by performing selective exposure of a resist film obtained by applying the resist composition to a support, the exposed areas change to have sparingly soluble properties from soluble properties in the organic developing solution, whereas the unexposed areas do not change in the state where they are still soluble. Thus, a contrast can be made between the exposed areas and unexposed areas by performing developing with an organic developing solution, and thus a negative type resist pattern is formed.

The component (A) which is used in the resist composition of this aspect includes a high-molecular weight compound (hereinafter, this high-molecular weight compound will be referred to as "component (A1)") having a constituent unit (a0) represented by the general formula (a0-1).

At least the component (A1) is used as the component (A), and with the component (A1), other high-molecular weight compounds and/or low-molecular weight compounds may be used in combination.

In the resist composition of this aspect, the component (A) is preferably the component (A-1). That is, the resist composition of this aspect is preferably a "positive type resist composition for use in an alkali development process" which is used to form a positive type resist pattern in the alkali development process, or a "negative type resist composition for use in a solvent development process" which is used to form a negative type resist pattern in the solvent development process. In addition, the component (A-1) preferably includes the component (A1).

Constituent Unit (a0):

The constituent unit (a0) is a constituent unit which is represented by the following general formula (a0-1).

[Chemical formula 14]

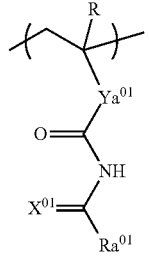

(a0-1)

In the formula, R represents a hydrogen atom, an alkyl group having 1 to 5 carbon atoms, or a halogenated alkyl group having 1 to 5 carbon atoms; $Ya^{01}$ represents a single bond or a divalent linking group; $X^{01}$ represents a sulfur atom or an oxygen atom; and $Ra^{01}$ represents an optionally substituted cyclic group, an optionally substituted chain alkyl group, or an optionally substituted chain alkenyl group.

In the formula (a0-1), the alkyl group having 1 to 5 carbon atoms in R is preferably a linear or branched alkyl group having 1 to 5 carbon atoms. Specifically, examples thereof include a methyl group, an ethyl group, a propyl group, an isopropyl group, an n-butyl group, an isobutyl group, a tert-butyl group, a pentyl group, an isopentyl group, and a neopentyl group.

The halogenated alkyl group having 1 to 5 carbon atoms is a group in which some or all the hydrogen atoms of the above-described "alkyl group having 1 to 5 carbon atoms in R" are substituted with halogen atoms. Examples of the halogen atom include a fluorine atom, a chlorine atom, a bromine atom, and an iodine atom, and a fluorine atom is especially preferable.

R is preferably a hydrogen atom, an alkyl group having 1 to 5 carbon atoms, or a fluorinated alkyl group having 1 to 5 carbon atoms, and is especially preferably a hydrogen atom or a methyl group in terms of easiness in industrial availability.

In the formula (a0-1), $Ya^{01}$ represents a single bond or a divalent linking group.

The divalent linking group in $Ya^{01}$ is not particularly limited, and preferred examples thereof include an optionally substituted divalent hydrocarbon group and a hetero atom-containing divalent linking group.

Optionally Substituted Divalent Hydrocarbon Group:

When $Ya^{01}$ represents an optionally substituted divalent hydrocarbon group, the hydrocarbon group may be an aliphatic hydrocarbon group or an aromatic hydrocarbon group.

Aliphatic hydrocarbon group in $Ya^{01}$ The aliphatic hydrocarbon group means a hydrocarbon group having no aromaticity. The aliphatic hydrocarbon group may be either saturated or unsaturated, and in general, it is preferably saturated.

Examples of the aliphatic hydrocarbon group include a linear or branched aliphatic hydrocarbon group, and an aliphatic hydrocarbon group containing a ring in a structure thereof.

Linear or Branched Aliphatic Hydrocarbon Group

The linear or branched aliphatic hydrocarbon group preferably has 1 to 10 carbon atoms, more preferably 1 to 6 carbon atoms, still more preferably 1 to 4 carbon atoms, and most preferably 1 to 3 carbon atoms.

The linear aliphatic hydrocarbon group is preferably a linear alkylene group, and specifically, examples thereof include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

The branched aliphatic hydrocarbon group is a branched alkylene group, and specifically, examples thereof include alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)$ $CH_2$—, —$CH(CH_3)CH(CH_3)$—, —$C(CH_3)_2CH_2$—, —$CH(CH_2CH_3)$ $CH_2$—, and —$C(CH_2CH_3)_2$—$CH_2$—; alkyltrimethylene groups such as —$CH(CH_3)$ $CH_2CH_2$— and —$CH_2CH(CH_3)$ $CH_2$—; and alkyltetramethylene groups such as —$CH(CH_3)$ $CH_2CH_2CH_2$— and —$CH_2CH(CH_3)$ $CH_2CH_2$—. As the alkyl group in the alkylalkylene group, a linear alkyl group having 1 to 5 carbon atoms is preferable.

The linear or branched aliphatic hydrocarbon group may or may not have a substituent. Examples of the substituent include a fluorine atom, a fluorinated alkyl group having 1 to 5 carbon atoms, which is substituted with a fluorine atom, and a carbonyl group.

Aliphatic Hydrocarbon Group Containing Ring in Structure Thereof

Examples of the aliphatic hydrocarbon group containing a ring in a structure thereof include an optionally substituted cyclic aliphatic hydrocarbon group containing a hetero atom in a ring structure thereof (a group in which two hydrogen atoms are eliminated from an aliphatic hydrocarbon ring), a group in which the cyclic aliphatic hydrocarbon group is bonded to the terminal of a linear or branched aliphatic hydrocarbon group, and a group in which the cyclic aliphatic hydrocarbon group intervenes on the way of a linear or branched aliphatic hydrocarbon group. Examples of the linear or branched aliphatic hydrocarbon group include the same groups as those described above.

The cyclic aliphatic hydrocarbon group has preferably 3 to 20 carbon atoms, and more preferably 3 to 12 carbon atoms.

The cyclic aliphatic hydrocarbon group may be either a polycyclic group or a monocyclic group. The monocyclic alicyclic hydrocarbon group is preferably a group in which two hydrogen atoms are eliminated from a monocycloalkane. The monocycloalkane is preferably one having 3 to 6 carbon atoms. Specifically, examples thereof include cyclopentane and cyclohexane. The polycyclic alicyclic hydrocarbon group is preferably a group in which two hydrogen atoms are eliminated from a polycycloalkane. The polycycloalkane is preferably one having 7 to 12 carbon atoms. Specifically, examples thereof include adamantane, norbornane, isobornane, tricyclodecane, and tetracyclododecane.

The cyclic aliphatic hydrocarbon group may or may not have a substituent. Examples of the substituent include an alkyl group, an alkoxy group, a halogen atom, a halogenated alkyl group, a hydroxyl group, and a carbonyl group.

The alkyl group as the substituent is preferably an alkyl group having 1 to 5 carbon atoms, and most preferably a methyl group, an ethyl group, a propyl group, an n-butyl group, or a tert-butyl group.

The alkoxy group as the substituent is preferably an alkoxy group having 1 to 5 carbon atoms, more preferably a methoxy group, an ethoxy group, an n-propoxy group, an isopropoxy group, an n-butoxy group, or a tert-butoxy group, and most preferably a methoxy group or an ethoxy group.

Examples of the halogen atom as the substituent include a fluorine atom, a chlorine atom, a bromine atom, and an iodine atom, with a fluorine atom being preferable.

Examples of the halogenated alkyl group as the substituent include a group in which some or all the hydrogen atoms of the above-described alkyl group are substituted with the above-described halogen atom.

In the cyclic aliphatic hydrocarbon group, some of the carbon atoms constituting the ring structure thereof may be substituted with a substituent containing a hetero atom. The substituent containing a hetero atom is preferably —O—, —C(=O)—O—, —S—, —S(=O)$_2$—, or —S(=O)$_2$—O—.

Aromatic Hydrocarbon Group in $Ya^{01}$

The aromatic hydrocarbon group is a hydrocarbon group having at least one aromatic ring.

This aromatic ring is not particularly limited so long as it is a cyclic conjugated system having (4n+2) π electrons, and it may be either monocyclic or polycyclic. The number of carbon atoms of the aromatic ring is preferably 5 to 30, more preferably 5 to 20, still more preferably 6 to 15, and especially preferably 6 to 12. However, the number of carbon atoms does not include the number of carbon atoms in the substituent. Specifically, examples of the aromatic ring include an aromatic hydrocarbon ring such as benzene, naphthalene, anthracene, and phenanthrene; and an aromatic heterocyclic ring in which some of the carbon atoms constituting the above-described aromatic hydrocarbon ring are substituted with a hetero atom. Examples of the hetero atom in the aromatic heterocyclic ring include an oxygen atom, a sulfur atom, and a nitrogen atom. Specifically, examples of the aromatic heterocyclic ring include a pyridine ring and a thiophene ring.

Specifically, examples of the aromatic hydrocarbon group include a group in which two hydrogen atoms are eliminated from the above-described aromatic hydrocarbon ring or aromatic heterocyclic ring (an arylene group or a heteroarylene group); a group in which two hydrogen atoms are eliminated from an aromatic compound containing two or more aromatic rings (for example, biphenyl or fluorene); and a group in which one hydrogen atom of a group in which one hydrogen atom is eliminated from the above-described aromatic hydrocarbon ring or aromatic heterocyclic ring (an aryl group or a heteroaryl group) is substituted with an alkylene group (for example, a group in which one hydrogen atom is further eliminated from an aryl group in an arylalkyl group such as a benzyl group, a phenethyl group, a 1-naphthylmethyl group, a 2-naphthylmethyl group, a 1-naphthylethyl group, and a 2-naphthylethyl group). The number of carbon atoms of the alkylene group bonded to the above-described aryl group or heteroaryl group is preferably 1 to 4, more preferably 1 to 2, and especially preferably 1.

In the above-described aromatic hydrocarbon group, the hydrogen atom(s) which the aromatic hydrocarbon group has may be substituted with a substituent. For example, the hydrogen atom(s) bonded to the aromatic ring in the aromatic hydrocarbon group may be substituted with a substituent. Examples of the substituent include an alkyl group, an alkoxy group, a halogen atom, a halogenated alkyl group, and a hydroxyl group.

The alkyl group as the substituent is preferably an alkyl group having 1 to 5 carbon atoms. The alkyl group is most preferably a methyl group, an ethyl group, a propyl group, an n-butyl group, or a tert-butyl group.

Examples of the alkoxy group, the halogen atom, and the halogenated alkyl group as the substituent include those exemplified above for the substituent with which the hydrogen atom(s) which the cyclic aliphatic hydrocarbon group has is substituted.

Hetero Atom-Containing Divalent Linking Group:

When $Ya^{01}$ represents a hetero atom-containing divalent linking group, preferred examples of the linking group include —O—, —C(=O)—O—, —C(=O)—, —O—C(=O)—O—, —C(=O)—NH—, —NH—, —NH—C(=NH)— (H may be substituted with a substituent such as an alkyl group and an acyl group), —S—, —S(=O)$_2$—, —S(=O)$_2$—O—, and a group represented by a general formula: —$Y^{21}$—O—$Y^{22}$—, —$Y^{21}$—O—, —$Y^{21}$—C(=O)—O—, —C(=O)—O—$Y^{21}$—, —[$Y^{21}$—C(=O)—O]$_{m''}$—$Y^{22}$—, —$Y^{21}$—O—C(=O)—$Y^{22}$—, or —$Y^{21}$—S(=O)$_2$—O—$Y^{22}$—. In the formulae, each of $Y^{21}$ and $Y^{22}$ independently represents an optionally substituted divalent hydrocarbon group, O represents an oxygen atom, and m" represents an integer of 0 to 3.

When the hetero atom-containing divalent linking group is —C(=O)—NH—, —C(=O)—NH—C(=O)—, —NH—, or —NH—C(=NH)—, H may be substituted with a substituent such as an alkyl group and an acyl group. The number of carbon atoms of the substituent (such as an alkyl group and an acyl group) is preferably 1 to 10, more preferably 1 to 8, and especially preferably 1 to 5.

In the general formula: —$Y^{21}$—O—$Y^{22}$—, —$Y^{21}$—O—, —$Y^{21}$—C(=O)—O—, —C(=O)O—$Y^{21}$—, —[$Y^{21}$—C(=O)—O]$_{m''}$—$Y^{22}$—, —$Y^{21}$—O—C(=O)—$Y^{22}$—, or —$Y^{21}$—S(=O)$_2$—O—$Y^{22}$—, each of $Y^{21}$ and $Y^{22}$ independently represents an optionally substituted divalent hydrocarbon group. Examples of the divalent hydrocarbon group include the same divalent hydrocarbon groups as those exemplified above for the divalent linking group (optionally substituted divalent hydrocarbon group).

$Y^{21}$ is preferably a linear aliphatic hydrocarbon group, more preferably a linear alkylene group, still more preferably a linear alkylene group having 1 to 5 carbon atoms, and especially preferably a methylene group or an ethylene group.

$Y^{22}$ is preferably a linear or branched aliphatic hydrocarbon group, and more preferably a methylene group, an ethylene group, or an alkylmethylene group. The alkyl group in the alkylmethylene group is preferably a linear alkyl group having 1 to 5 carbon atoms, more preferably a linear alkyl group having 1 to 3 carbon atoms, and most preferably a methyl group.

In the group represented by the formula: —[$Y^{21}$—C(=O)—O]$_{m''}$—$Y^{22}$—, m" represents an integer of 0 to 3, preferably an integer of 0 to 2, more preferably 0 or 1, and especially preferably 1. Namely, the group represented by the formula: —[$Y^{21}$—C(=O)—O]$_{m''}$—$Y^{22}$— is especially preferably a group represented by the formula: —$Y^{21}$—C(=O)—O—$Y^{22}$—. Above all, a group represented by the formula: —(CH$_2$)$_{a'}$—C(=O)—O—(CH$_2$)$_{b'}$— is preferable. In the foregoing formula, a' represents an integer of 1 to 10, preferably an integer of 1 to 8, more preferably an integer of 1 to 5, still more preferably 1 or 2, and most preferably 1. b' represents an integer of 1 to 10, preferably 1 to 8, more preferably 1 to 5, still more preferably 1 or 2, and most preferably 1.

$Ya^{01}$ is preferably a single bond, an ester bond [—C(=O)—O—], an ether bond (—O—), a linear or branched alkylene group, or a combination thereof. Of these, $Ya^{01}$ is more preferably a single bond.

In the formula (a0-1), $X^{01}$ is a sulfur atom or an oxygen atom, and an oxygen atom is preferable.

In the formula (a0-1), $Ra^{01}$ is an optionally substituted cyclic group, an optionally substituted chain alkyl group, or an optionally substituted chain alkenyl group.

Optionally Substituted Cyclic Group:

The cyclic group is preferably a cyclic hydrocarbon group. The cyclic hydrocarbon group may be an aromatic hydrocarbon group or a cyclic aliphatic hydrocarbon group. The aliphatic hydrocarbon group means a hydrocarbon group having no aromaticity. In addition, the aliphatic hydrocarbon group may be either saturated or unsaturated, and in general, it is preferably saturated.

The aromatic hydrocarbon group in $Ra^{01}$ is a hydrocarbon group having at least one aromatic ring.

This aromatic ring is not particularly limited so long as it is a cyclic conjugated system having (4n+2) π electrons, and it may be either monocyclic or polycyclic. The number of carbon atoms of the aromatic ring is preferably 5 to 30, more preferably 5 to 20, still more preferably 6 to 15, and especially preferably 6 to 12. However, the number of carbon atoms does not include the number of carbon atoms in the substituent. Specifically, examples of the aromatic ring include an aromatic hydrocarbon ring such as benzene, naphthalene, anthracene, and phenanthrene; and an aromatic heterocyclic ring in which some of the carbon atoms constituting the above-described aromatic hydrocarbon ring are substituted with a hetero atom. Examples of the hetero atom in the aromatic heterocyclic ring include an oxygen atom, a sulfur atom, and a nitrogen atom. Specifically, examples of the aromatic heterocyclic ring include a pyridine ring and a thiophene ring.

Specifically, examples of the aromatic hydrocarbon group in $Ra^{01}$ include a group in which one hydrogen atom is eliminated from the above-described aromatic hydrocarbon ring or aromatic heterocyclic ring (an aryl group or a heteroaryl group); a group in which one hydrogen atom is eliminated from an aromatic compound containing two or more aromatic rings (for example, biphenyl or fluorene); and a group in which one hydrogen atom of the above-described aromatic hydrocarbon ring or aromatic heterocyclic ring is substituted with an alkylene group (for example, an arylalkyl group such as a benzyl group, a phenethyl group, a 1-naphthylmethyl group, a 2-naphthylmethyl group, a 1-naphthylethyl group, and a 2-naphthylethyl group). The number of carbon atoms of the alkylene group bonded to the above-described aromatic hydrocarbon ring or aromatic heterocyclic ring is preferably 1 to 4, more preferably 1 to 2, and especially preferably 1.

Examples of the cyclic aliphatic hydrocarbon group in $Ra^{01}$ include an aliphatic hydrocarbon group containing a ring in a structure thereof.

Examples of the aliphatic hydrocarbon group containing a ring in a structure thereof include an alicyclic hydrocarbon group (a group in which one hydrogen atom is eliminated from an aliphatic hydrocarbon ring), a group in which an alicyclic hydrocarbon group is bonded to the terminal of a linear or branched aliphatic hydrocarbon group, and a group in which an alicyclic hydrocarbon group intervenes on the way of a linear or branched aliphatic hydrocarbon group.

The number of carbon atoms of the above-described alicyclic hydrocarbon group is preferably 3 to 20, and more preferably 3 to 12.

The above-described alicyclic hydrocarbon group may be either a polycyclic group or a monocyclic group. The monocyclic alicyclic hydrocarbon group is preferably a group in which one or more hydrogen atoms are eliminated from a monocycloalkane. The monocycloalkane is preferably one having 3 to 6 carbon atoms, and specifically, examples thereof include cyclopentane and cyclohexane. The polycyclic alicyclic hydrocarbon group is preferably a group in which one or more hydrogen atoms are eliminated from a polycycloalkane. The polycycloalkane is preferably one having 7 to 12 carbon atoms, and specifically, examples thereof include adamantane, norbornane, isobornane, tricyclodecane, and tetracyclododecane.

Above all, the alicyclic hydrocarbon group in $Ra^{01}$ is preferably a polycyclic group, more preferably a group in which one hydrogen atom is eliminated from a polycycloalkane, especially preferably an adamantyl group or a norbornyl group, and most preferably an adamantyl group.

The number of carbon atoms of the linear or branched aliphatic hydrocarbon group which may be bonded to an alicyclic hydrocarbon group is preferably 1 to 10, more preferably 1 to 6, still more preferably 1 to 4, and most preferably 1 to 3.

The linear aliphatic hydrocarbon group is preferably a linear alkylene group. Specifically, examples thereof include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

The branched aliphatic hydrocarbon group is preferably a branched alkylene group. Specifically, examples thereof include an alkylalkylene group such as an alkylmethylene group, for example, —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; an alkylethylene group, for example, —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; an alkyltrimethylene group, for example, —$CH(CH_3)CH_2CH_2$— and —$CH_2CH(CH_3)CH_2$—; and an alkyltetramethylene group, for example, —$CH(CH_3)CH_2CH_2CH_2$— and —$CH_2CH(CH_3)CH_2CH_2$—. The alkyl group in the alkylalkylene group is preferably a linear alkyl group having 1 to 5 carbon atoms.

In addition, the cyclic hydrocarbon group in $Ra^{01}$ may contain a hetero atom as in a heterocyclic ring or the like. Specifically, examples thereof include lactone-containing cyclic groups represented by general formulae (a2-r-1) to (a2-r-7) to be described later, respectively, and —$SO_2$—-containing cyclic groups represented by general formulae (a5-r-1) to (a5-r-4) to be described later, respectively, and besides, heterocyclic groups which will be exemplified below. Of these, lactone-containing cyclic groups represented by the general formulae (a2-r-1) to (a2-r-7), respectively, and —$SO_2$—-containing cyclic groups represented by the general formulae (a5-r-1) to (a5-r-4), respectively are especially preferable. In the formulae, * represents a bond (and has the same usage below).

[Chemical formula 15]

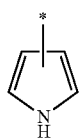

(r-hr-1)

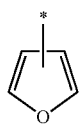

(r-hr-2)

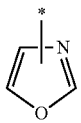

(r-hr-3)

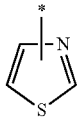

(r-hr-4)

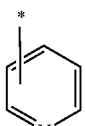

(r-hr-5)

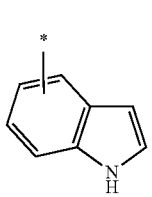

(r-hr-6)

(r-hr-7)

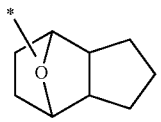

(r-hr-8)

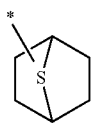

(r-hr-9)

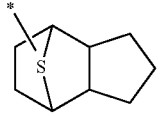

(r-hr-10)

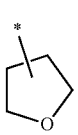

(r-hr-11)

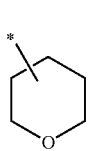

(r-hr-12)

(r-hr-13)

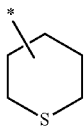
(r-hr-14)

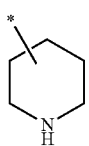
(r-hr-15)

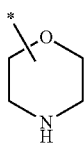
(r-hr-16)

Examples of the substituent which the cyclic group represented by $Ra^{01}$ may have include an alkyl group, an alkoxy group, a halogen atom, a halogenated alkyl group, a hydroxyl group, a carbonyl group (—C(=O)—), an ether bond (—O—), an ester bond (—C(=O)—O—), and a nitro group.

The alkyl group as the substituent is preferably an alkyl group having 1 to 5 carbon atoms, and most preferably a methyl group, an ethyl group, a propyl group, an n-butyl group, or a tert-butyl group.

The alkoxy group as the substituent is preferably an alkoxy group having 1 to 5 carbon atoms, more preferably a methoxy group, an ethoxy group, an n-propoxy group, an isopropoxy group, an n-butoxy group, or a tert-butoxy group, and most preferably a methoxy group or an ethoxy group.

Examples of the halogen atom as the substituent include a fluorine atom, a chlorine atom, a bromine atom, and an iodine atom, with a fluorine atom being preferable.

Examples of the halogenated alkyl group as the substituent include a group in which some or all the hydrogen atoms of an alkyl group having 1 to 5 carbon atoms, for example, a methyl group, an ethyl group, a propyl group, an n-butyl group, or a tert-butyl group, are substituted with the above-described halogen atom.

The carbonyl group (—C(=O)—), the ether bond (—O—), and the ester bond (—C(=O)—O—) as the substituent are groups with which a methylene group (—CH$_2$—) constituting the cyclic group is substituted.

Optionally Substituted Chain Alkyl Group:

The chain alkyl group in $Ra^{01}$ may be either linear or branched.

The number of carbon atoms of the linear alkyl group is preferably 1 to 20, more preferably 1 to 15, still more preferably 1 to 10, and especially preferably 1 to 5. Specifically, examples thereof include a methyl group, an ethyl group, a propyl group, a butyl group, a pentyl group, a hexyl group, a heptyl group, an octyl group, a nonyl group, a decanyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an eicosyl group, a heneicosyl group, and a docosyl group.

The number of carbon atoms of the branched alkyl group is preferably 3 to 20, more preferably 3 to 15, and still more preferably 3 to 10. Specifically, examples thereof include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, and a 4-methylpentyl group.

Optionally Substituted Chain Alkenyl Group

The chain alkenyl group in $Ra^{01}$ may be either linear or branched. The number of carbon atoms of the chain alkenyl group is preferably 2 to 10, more preferably 2 to 5, still more preferably 2 to 4, and especially preferably 3. Examples of the linear alkenyl group include a vinyl group, a propenyl group (allyl group), and a butynyl group. Examples of the branched alkenyl group include a 1-methylvinyl group, a 2-methylvinyl group, a 1-methylpropenyl group, and a 2-methylpropenyl group.

Above all, the chain alkenyl group is more preferably a vinyl group or a propenyl group, and especially preferably a vinyl group.

Examples of the substituent which the chain alkyl group or chain alkenyl group in $Ra^{01}$ may have include an alkoxy group, a halogen atom, a halogenated alkyl group, a hydroxyl group, a carbonyl group (—C(=O)—), an ether bond (—O—), an ester bond (—C(=O)—O—), a nitro group, an amino group, and the cyclic groups in the above-described $Ra^{01}$.

The alkoxy group as the substituent is preferably an alkoxy group having 1 to 5 carbon atoms, more preferably a methoxy group, an ethoxy group, an n-propoxy group, an isopropoxy group, an n-butoxy group, or a tert-butoxy group, and most preferably a methoxy group or an ethoxy group.

Examples of the halogen atom as the substituent include a fluorine atom, a chlorine atom, a bromine atom, and an iodine atom, with a fluorine atom being preferable.

Examples of the halogenated alkyl group as the substituent include a group in which some or all the hydrogen atoms of an alkyl group having 1 to 5 carbon atoms, for example, a methyl group, an ethyl group, a propyl group, an n-butyl group, or a tert-butyl group, are substituted with the above-described halogen atom.

The carbonyl group (—C(=O)—), the ether bond (—O—), and the ester bond (—C(=O)—O—) as the substituent are groups with which a methylene group (—CH$_2$—) constituting the chain alkyl group or chain alkenyl group is substituted.

Of the foregoing, $Ra^{01}$ is preferably an optionally substituted cyclic group, and more preferably an optionally substituted cyclic hydrocarbon group in view of the fact that sensitivity further increases in the formation of a resist pattern. Above all, for an improvement of roughness and for excellent lithography properties such as an exposure margin, $Ra^{01}$ is especially preferably an aromatic hydrocarbon group or an aliphatic hydrocarbon group containing a polycyclic group in a structure thereof (a carbon atom or a hydrogen atom of the aromatic hydrocarbon group or the aliphatic hydrocarbon group may be substituted with a substituent), and most preferably an aliphatic hydrocarbon group containing a polycyclic group in a structure thereof (a carbon atom or a hydrogen atom of the aliphatic hydrocarbon group may be substituted with a substituent).

Preferred examples of the constituent unit (a0) include constituent units represented by the following general formula (a0-1-1), (a0-1-2), or (a0-1-3) in view of the fact that sensitivity, resolution, and lithography properties are further enhanced.

[Chemical formula 16]

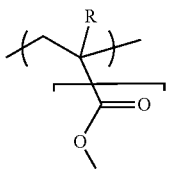
(a0-1-1)

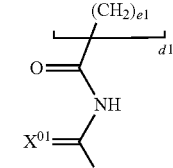
(a0-1-2)

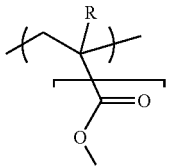
(a0-1-3)

In the formula, R represents a hydrogen atom, an alkyl group having 1 to 5 carbon atoms or a halogenated alkyl group having 1 to 5 carbon atoms; $X^{01}$ represents a sulfur atom or an oxygen atom; $Ra^{o11}$ represents an aromatic hydrocarbon group (a carbon atom or a hydrogen atom of the aromatic hydrocarbon group may be substituted with a substituent); $Ra^{o12}$ represents an aliphatic hydrocarbon group containing a polycyclic group (a carbon atom or a hydrogen atom of the aliphatic hydrocarbon group may be substituted with a substituent); $Ra^{o13}$ represents an aliphatic hydrocarbon group other than the group represented by $Ra^{o12}$ (a carbon atom or a hydrogen atom of the aliphatic hydrocarbon group may be substituted with a substituent); each of d1, d2, and d3 represents 0 or 1; and each of e1, e2, and e3 represents an integer of 1 to 5.

In the formula (a0-r-1), (a0-1-2), or (a0-1-3), R is the same as R in the formula (a0-1).

$X^{01}$ is a sulfur atom or an oxygen atom, and is preferably an oxygen atom.

In the formula (a0-r-1), the aromatic hydrocarbon group in $Ra^{o11}$ is the same as the aromatic hydrocarbon group in $Ra^{o1}$ in the formula (a0-1). $Ra^{o11}$ is preferably a group in which one hydrogen atom is eliminated from an aromatic ring (aromatic hydrocarbon ring), and especially preferably a phenyl group or a naphthyl group. The substituent with which the aromatic hydrocarbon group in $Ra^{o11}$ is substituted is the same as that in the description of the substituent which the above-described cyclic group represented by $Ra^{o1}$ may have.

The hydrogen atom of the aromatic hydrocarbon group in $Ra^{o11}$ is preferably substituted with a substituent, and is more preferably substituted with a halogen atom. The halogen atom is preferably a fluorine atom or a bromine atom.

In the formula (a0-r-2), the aliphatic hydrocarbon group containing a polycyclic group in $Ra^{o12}$ is the same as the aliphatic hydrocarbon group containing a polycyclic group in the description of the cyclic aliphatic hydrocarbon group in $Ra^{o1}$ in the formula (a0-1). $Ra^{o12}$ is preferably an alicyclic hydrocarbon group which is a polycyclic group or a heterocyclic group which is a polycyclic group, and more preferably a group in which one hydrogen atom is eliminated from a polycycloalkane or a lactone-containing cyclic group.

The substituent with which the aliphatic hydrocarbon group containing a polycyclic group in $Ra^{o12}$ is substituted is the same as that in the description of the substituent which the above-described cyclic group in $Ra^{o1}$ may have.

In the formula (a0-r-3), $Ra^{o13}$ is the same as the group other than the aliphatic hydrocarbon group containing a polycyclic group (an aliphatic hydrocarbon group containing a monocyclic group), the optionally substituted chain alkyl group, and the optionally substituted chain alkenyl group in the description of the cyclic aliphatic hydrocarbon group in $Ra^{o1}$ in the formula (a0-1)

Specific examples of the constituent unit (a0) are given below. In the following formulae, $R^{\alpha}$ represents a hydrogen atom, a methyl group, or a trifluoromethyl group.

[Chemical formula 17]

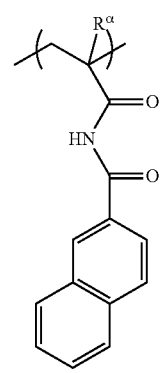
(a0-1-111)

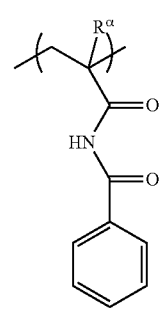
(a0-1-112)

(a0-1-113) 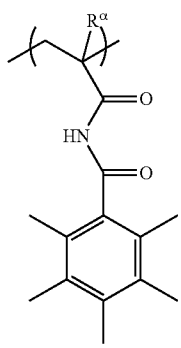
(a0-1-114) 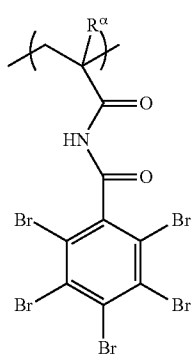
(a0-1-115) 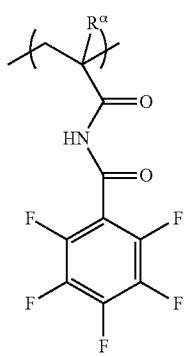
(a0-1-116) 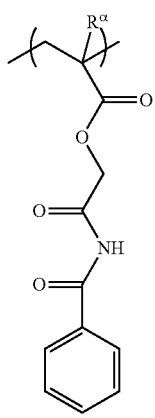
(a0-1-117) 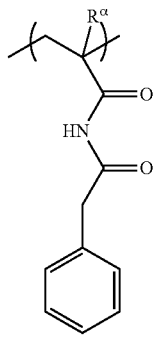
(a0-1-118) 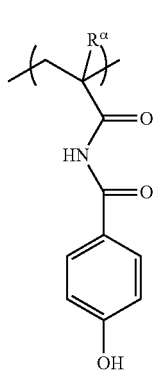
(a0-1-119) 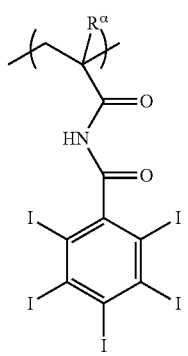
(a0-1-120) 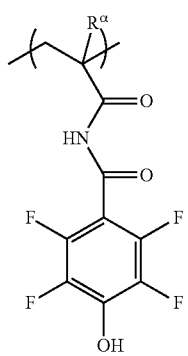

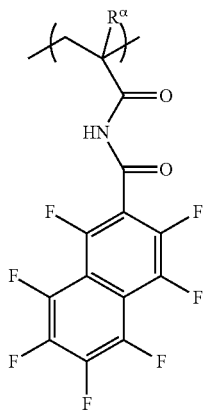 (a0-1-121)
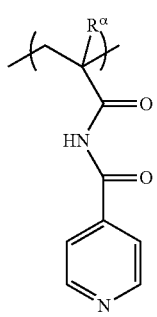 (a0-1-122)
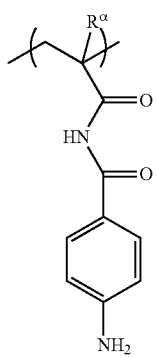 (a0-1-123)
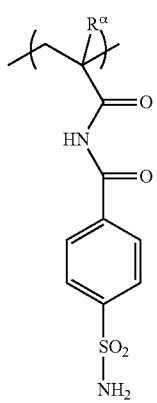 (a0-1-124)
[Chemical formula 18]
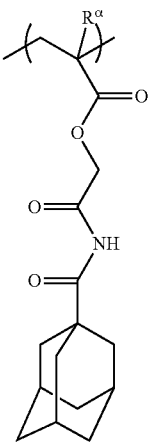 (a0-1-211)
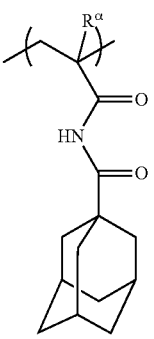 (a0-1-212)
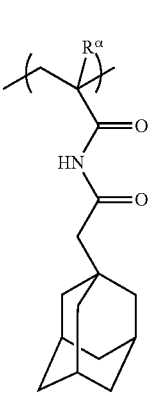 (a0-1-213)
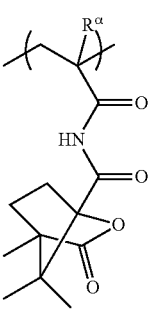 (a0-1-214)

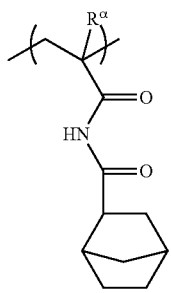 (a0-1-215)
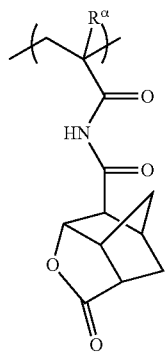 (a0-1-219)
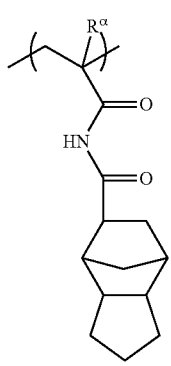 (a0-1-216)
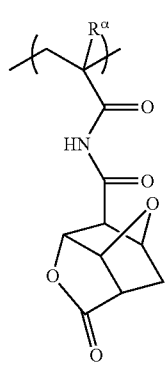 (a0-1-220)
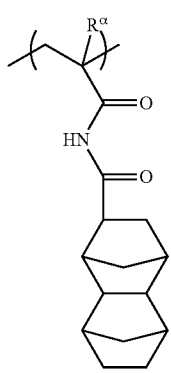 (a0-1-217)
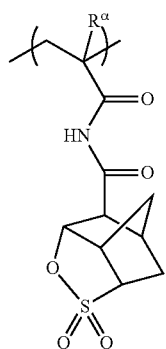 (a0-1-221)
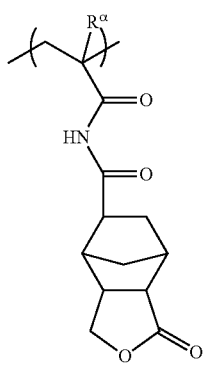 (a0-1-218)
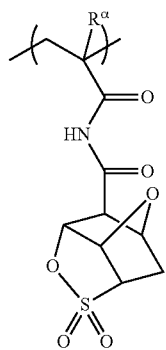 (a0-1-222)

-continued

[Chemical formula 19]

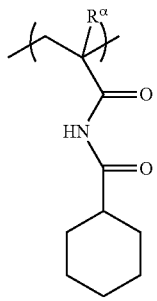
(a0-1-311)

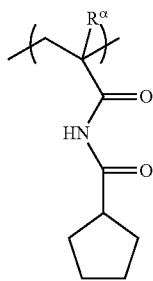
(a0-1-312)

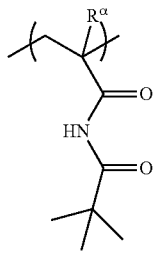
(a0-1-313)

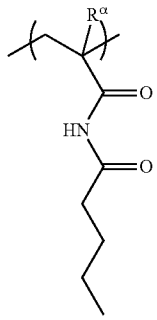
(a0-1-314)

Preferred examples of the resist composition of this aspect include the following embodiments.

First Embodiment

A resist composition which generates an acid upon exposure and exhibits changed solubility in a developing solution by the action of the acid, including: a base material component (A) which exhibits changed solubility in a developing solution by the action of an acid, an acid generator component (B) which generates an acid upon exposure, and a compound (D1) which includes a partial structure represented by the general formula (a0-r-1), in which the base material component (A) contains a high-molecular weight compound having a constituent unit (a0) represented by the general formula (a0-1).

Second Embodiment

A resist composition including: a base material component which generates an acid upon exposure and exhibits changed solubility in a developing solution by the action of the acid, and an acid generator component (B) which generates an acid upon exposure, in which the base material component contains a high-molecular weight compound having a constituent unit (a0) represented by the general formula (a0-1) and a constituent unit (a15) including a partial structure represented by the general formula (a0-r-1).

First Embodiment of Resist Composition

A resist composition of the first embodiment (hereinafter, this resist composition will also be referred to as "resist composition (1)") is a resist composition which generates an acid upon exposure and exhibits changed solubility in a developing solution by the action of the acid, and contains a base material component (A) which exhibits changed solubility in a developing solution by the action of an acid, an acid generator component (B) which generates an acid upon exposure, and a compound (D1) which includes a partial structure represented by the general formula (a0-r-1).

Base Material Component (A): Component (A)

In the resist composition (1), the component (A) contains a high-molecular weight compound (component (A1)) having a constituent unit (a0) represented by the general formula (a0-1).

Component (A1):

The component (A1) is a high-molecular weight compound having a constituent unit (a0) represented by the general formula (a0-1).

Constituent Unit (a0)

The constituent unit (a0) is the same as the above-described constituent unit (a0).

The constituent unit (a0) is preferably at least one kind selected from the group consisting of constituent units represented by the general formulae (a0-1-1), (a0-1-2), and (a0-1-3), respectively. It is more preferably at least one kind selected from the group consisting of constituent units represented by the general formulae (a0-1-1) and (a0-1-2), respectively, and especially preferably a constituent unit represented by the general formula (a0-1-2), since both a roughness decreasing effect and an exposure margin improving effect are easily obtained.

Specifically, constituent units represented by the formulae (a0-1-212), (a0-1-214), (a0-1-219), (a0-1-220), and (a0-1-221), respectively, are preferable. Of these, constituent units represented by the formulae (a0-1-212) and (a0-1-214), respectively, are especially preferable.

The constituent unit (a0) which the component (A1) has may be either one kind or two or more kinds.

A proportion of the constituent unit (a0) in the component (A1) is preferably 1 mol % to 35 mol %, more preferably 5 mol % to 30 mol %, still more preferably 5 mol % to 20 mol %, and especially preferably 10 mol % to 20 mol % relative to a total sum of all of the constituent units constituting the component (A1).

When the proportion of the constituent unit (a0) is not more than the preferred upper limit value, high sensitivity is maintained and a resist pattern having a good shape is easily obtained. On the other hand, when the proportion of the constituent unit (a0) is the preferred lower limit value or more, sensitivity increases and lithography properties such as resolution and an exposure margin (EL margin) are also enhanced.

Other Constituent Units

The component (A1) may further have, in addition to the constituent unit (a0), other constituent units.

The foregoing other constituent units are not particularly limited so long as they are a constituent unit which is not classified into the above-described constituent units (a0). A large number of constituent units which have been conventionally known to be used for resins for resist such as those for ArF excimer lasers and KrF excimer lasers (preferably those for ArF excimer lasers), and the like can be used. Examples thereof include constituent units (a1) to (a4) as described below and constituent units which generate an acid upon exposure.

Constituent Unit (a1)

In the resist composition (1), it is preferable that the component (A1) further has, in addition to the constituent unit (a0), a constituent unit (a1) which contains an acid decomposable group whose polarity increases by the action of an acid.

In the case where the resist composition (1) contains a high-molecular weight compound having the constituent unit (a0) and the constituent unit (a1), when a resist film formed using the resist composition (1) is exposed, at least a part of the bond in the structure of the constituent unit (a1) is cleaved by the action of an acid in the resist film and the polarity increases. Since the component (A1) varies in polarity before and after exposure, a satisfactory development contrast can be obtained using the component (A1) not only in the alkali development process, but also in the solvent development process. In addition, the resist composition (1) becomes a positive type in an alkali development process, and becomes a negative type in a solvent development process.

The term "acid decomposable group" refers to a group having acid decomposability, in which at least a part of the bond in the structure of the acid decomposable group may be cleaved by the action of an acid.

Examples of the acid decomposable group whose polarity increases by the action of an acid include a group which is decomposed by the action of an acid to form a polar group.

Examples of the polar group include a carboxy group, a hydroxyl group, an amino group, and a sulfo group (—SO$_3$H). Of these, a polar group containing —OH in a structure thereof (hereinafter, sometimes referred to as "OH-containing polar group") is preferable, a carboxy group or a hydroxyl group is more preferable, and a carboxy group is especially preferable.

More specifically, examples of the acid decomposable group include a group in which the above-described polar group is protected by an acid dissociable group (for example, a group in which the hydrogen atom of the OH-containing polar group is protected by an acid dissociable group).

Here, the term "acid dissociable group" refers to either one or both of the following groups: (i) a group having such acid dissociation properties that the bond between the acid dissociable group and the atom adjacent to the acid dissociable group may be cleaved by the action of an acid, and (ii) a group in which after a part of the bond is cleaved by the action of an acid, a decarboxylation reaction is further caused, whereby the bond between the acid dissociable group and the atom adjacent to the acid dissociable group may be cleaved.

It is necessary that the acid dissociable group constituting the acid decomposable group is a group with lower polarity than a polar group formed upon dissociation of the acid dissociable group. According to this, on the occasion of dissociation of the acid dissociable group by the action of an acid, a polar group having higher polarity than the acid dissociable group is formed, whereby the polarity increases. As a result, the polarity of the whole of the component (A1) increases. When the polarity increases, the solubility in a developing solution relatively changes. In the case where the developing solution is an alkali developing solution, the solubility increases, and in the case where the developing solution is an organic developing solution, the solubility decreases.

Examples of the acid dissociable group include those which have been so far proposed as an acid dissociable group of a base resin for a chemically amplified resist.

Specific examples of those proposed as an acid dissociable group of a base resin for a chemically amplified resist include an "acetal type acid dissociable group" a "tertiary alkyl ester type acid dissociable group", and a "tertiary alkyloxycarbonyl acid dissociable group" to be described as follows.

Acetal-Type Acid Dissociable Group:

Among the above-described polar groups, examples of the acid dissociable group which protects a carboxy group or a hydroxyl group include an acid dissociable group represented by the following general formula (a1-r-1) (hereinafter, sometimes referred to as "acetal type acid dissociable group").

[Chemical formula 20]

(a1-r-1)

In the formula, each of $Ra'^1$ and $Ra'^2$ represents a hydrogen atom or an alkyl group; $Ra'^3$ represents a hydrocarbon group; and $Ra'^3$ may be bonded to either $Ra'^1$ or $Ra'^2$ to form a ring.

In the formula (a1-r-1), it is preferable that at least one of $Ra'^1$ and $Ra'^2$ is a hydrogen atom, and it is more preferable that both of $Ra'^1$ and $Ra'^2$ are a hydrogen atom.

In the case where $Ra'^1$ or $Ra'^2$ is an alkyl group, examples of the alkyl group include the same alkyl groups as those exemplified as the substituent which may be bonded to the carbon atom at the α-position in the description of the α-substituted acrylic ester, and an alkyl group having 1 to 5 carbon atoms is preferable. Specifically, there is preferably exemplified a linear or branched alkyl group. More specifically, examples thereof include a methyl group, an ethyl group, a propyl group, an isopropyl group, an n-butyl group, an isobutyl group, a tert-butyl group, a pentyl group, an isopentyl group, and a neopentyl group. A methyl group or an ethyl group is more preferable, and a methyl group is especially preferable.

In the formula (a1-r-1), examples of the hydrocarbon group represented by $Ra'^3$ include a linear or branched alkyl group and a cyclic hydrocarbon group.

The number of carbon atoms of the linear alkyl group is preferably 1 to 5, more preferably 1 to 4, and still more preferably 1 or 2. Specifically, examples thereof include a methyl group, an ethyl group, an n-propyl group, an n-butyl group, and an n-pentyl group. Of these, a methyl group, an ethyl group, or an n-butyl group is preferable, and a methyl group or an ethyl group is more preferable.

The number of carbon atoms of the branched alkyl group is preferably 3 to 10, and more preferably 3 to 5. Specifically, examples thereof include an isopropyl group, an isobutyl group, a tert-butyl group, an isopentyl group, a neopentyl group, a 1,1-diethylpropyl group, and a 2,2-dimethylbutyl group, with an isopropyl group being preferable.

In the case where $Ra'^3$ is a cyclic hydrocarbon group, the hydrocarbon group may be either aliphatic or aromatic, and it may be either a polycyclic group or a monocyclic group.

The monocyclic aliphatic hydrocarbon group is preferably a group in which one hydrogen atom is eliminated from a monocycloalkane. The monocycloalkane is preferably one having 3 to 6 carbon atoms, and specifically, examples thereof include cyclopentane and cyclohexane.

The polycyclic aliphatic hydrocarbon group is preferably a group in which one hydrogen atom is eliminated from a polycycloalkane. The polycycloalkane is preferably one having 7 to 12 carbon atoms, and specifically, examples thereof include adamantane, norbornane, isobornane, tricyclodecane, and tetracyclododecane.

In the case where the cyclic hydrocarbon group represented by $Ra'^3$ is an aromatic hydrocarbon group, the aromatic hydrocarbon group is a hydrocarbon group having at least one aromatic ring.

This aromatic ring is not particularly limited so long as it is a cyclic conjugated system having (4n+2) π electrons, and it may be either monocyclic or polycyclic. The number of carbon atoms of the aromatic ring is preferably 5 to 30, more preferably 5 to 20, still more preferably 6 to 15, and especially preferably 6 to 12. Specifically, examples of the aromatic ring include an aromatic hydrocarbon ring such as benzene, naphthalene, anthracene, and phenanthrene; and an aromatic heterocyclic ring in which some of the carbon atoms constituting the above-described aromatic hydrocarbon ring are substituted with a hetero atom. Examples of the hetero atom in the aromatic heterocyclic ring include an oxygen atom, a sulfur atom, and a nitrogen atom. Specifically, examples of the aromatic heterocyclic ring include a pyridine ring and a thiophene ring.

Specifically, examples of the aromatic hydrocarbon group in $Ra'^3$ include a group in which one hydrogen atom is eliminated from the above-described aromatic hydrocarbon ring or aromatic heterocyclic ring (an aryl group or a heteroaryl group); a group in which one hydrogen atom is eliminated from an aromatic compound containing two or more aromatic rings (for example, biphenyl or fluorene); and a group in which one hydrogen atom of the above-described aromatic hydrocarbon ring or aromatic heterocyclic ring is substituted with an alkylene group (for example, an arylalkyl group such as a benzyl group, a phenethyl group, a 1-naphthylmethyl group, a 2-naphthylmethyl group, a 1-naphthylethyl group, and a 2-naphthylethyl group). The number of carbon atoms of the alkylene group bonded to the above-described aromatic hydrocarbon ring or aromatic heterocyclic ring is preferably 1 to 4, more preferably 1 to 2, and especially preferably 1.

In the case where $Ra'^3$ is bonded to either $Ra'^1$ or $Ra'^2$ to form a ring, the cyclic group is preferably a 4-membered to 7-membered ring, and more preferably a 4-membered to 6-membered ring. Specific examples of the cyclic group include a tetrahydropyranyl group and a tetrahydrofuranyl group.

Tertiary Alkyl Ester Type Acid Dissociable Group:

Among the above-described polar groups, examples of the acid dissociable group which protects a carboxy group include an acid dissociable group represented by the following general formula (a1-r-2). It is to be noted that among the acid dissociable groups represented by the following formula (a1-r-2), a group constituted of an alkyl group is hereinafter sometimes referred to as "tertiary alkyl ester type acid dissociable group" for the sake of convenience.

[Chemical formula 21]

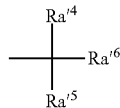

(a1-r-2)

In the formula, each of $Ra'^4$ to $Ra'^6$ represents a hydrocarbon group, and $Ra'^5$ and $Ra'^6$ may be bonded to each other to form a ring.

Examples of the hydrocarbon group represented by $Ra'^4$ to $Ra'^6$ include the same hydrocarbon groups as those exemplified above for $Ra'^3$.

$Ra'^4$ is preferably an alkyl group having 1 to 5 carbon atoms. In the case where $Ra'^5$ and $Ra'^6$ are bonded to each other to form a ring, a group represented by the following general formula (a1-r2-1) is exemplified. On the other hand, in the case where $Ra'^4$ to $Ra'^6$ are not bonded to each other and are each an independent hydrocarbon group, a group represented by the following general formula (a1-r2-2) is exemplified.

[Chemical formula 22]

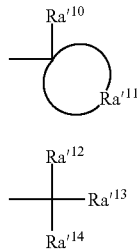

(a1-r2-1)

(a1-r2-2)

In the formulae, $Ra'^{10}$ represents an alkyl group having 1 to 10 carbon atoms; $Ra'^{11}$ represents a group for forming an aliphatic cyclic group together with the carbon atom to which $Ra'^{10}$ is bonded; and each of $Ra'^{12}$ to $Ra'^{14}$ independently represents a hydrocarbon group.

In the formula (a1-r2-1), the alkyl group having 1 to 10 carbon atoms represented by $Ra'^{10}$ is preferably the group exemplified as the linear or branched alkyl group represented by $Ra'^3$ in the formula (a1-r-1). In the formula (a1-r-1), as the aliphatic cyclic group which $Ra'^{11}$ forms together with the carbon atom to which $Ra'^{10}$ is bonded, the groups exemplified as the aliphatic hydrocarbon group represented by $Ra'^3$ in the formula (a1-r-1), which is either a monocyclic group or a polycyclic group, are preferable.

In the formula (a0-r-2), each of $Ra'^{12}$ and $Ra'^{14}$ is preferably independently an alkyl group having 1 to 10 carbon atoms. The alkyl group is more preferably the group exemplified as the linear or branched alkyl group represented by $Ra'^3$ in the formula (a1-r-1), still more preferably a linear alkyl group having 1 to 5 carbon atoms, and especially preferably a methyl group or an ethyl group.

In the formula (a0-r-2), $Ra'^{13}$ is preferably the linear or branched alkyl group exemplified as the hydrocarbon group represented by $Ra'^3$ in the formula (a1-r-1), or an aliphatic hydrocarbon group which is either a monocyclic group or a polycyclic group. Of these, $Ra'^{13}$ is more preferably the group exemplified as the aliphatic hydrocarbon group represented by $Ra'^3$, which is either a monocyclic group or a polycyclic group.

Specific examples of the group represented by the formula (a1-r2-1) are given below.
[Chemical formula 23]
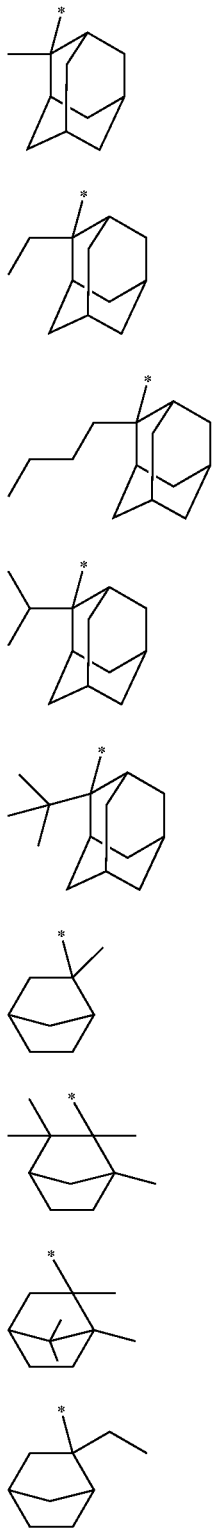
(r-pr-m1)
(r-pr-m2)
(r-pr-m3)
(r-pr-m4)
(r-pr-m5)
(r-pr-m6)
(r-pr-m7)
(r-pr-m8)
(r-pr-m9)
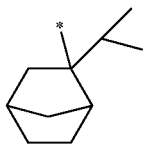
(r-pr-m10)
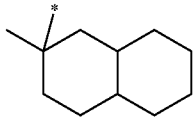
(r-pr-m11)
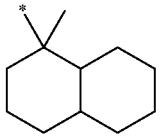
(r-pr-m12)
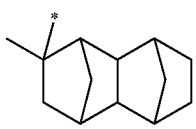
(r-pr-m13)
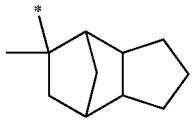
(r-pr-m14)
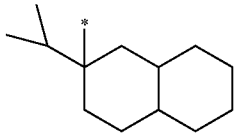
(r-pr-m15)
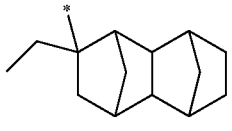
(r-pr-m16)
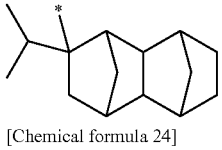
(r-pr-m17)
[Chemical formula 24]
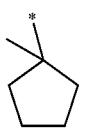
(r-pr-s1)
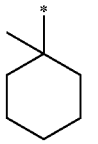
(r-pr-s2)
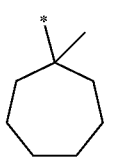
(r-pr-s3)

(r-pr-s4) 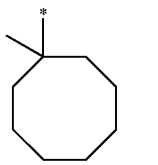
(r-pr-s5) 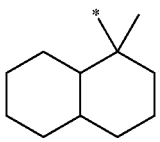
(r-pr-s6) 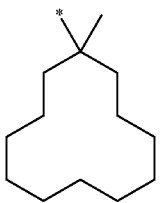
(r-pr-s7) 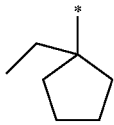
(r-pr-s8) 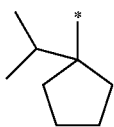
(r-pr-s9) 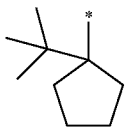
(r-pr-s10) 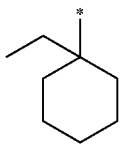
(r-pr-s11) 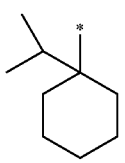
(r-pr-s12) 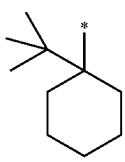
(r-pr-s13) 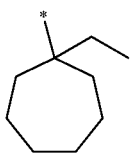
(r-pr-s14) 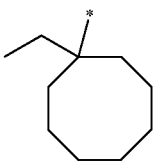
(r-pr-s15) 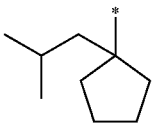
(r-pr-s16) 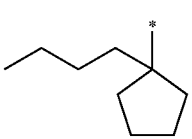
(r-pr-s17) 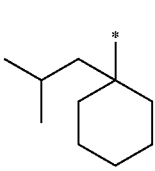
(r-pr-s18) 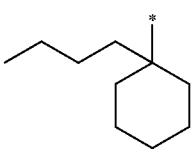
Specific examples of each of the groups represented by the formula (a1-r2-2) are given below.
[Chemical formula 25]
(r-pr-cm1) 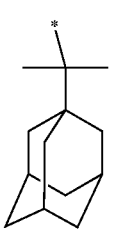
(r-pr-cm2) 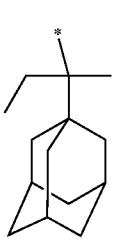
(r-pr-cm3) 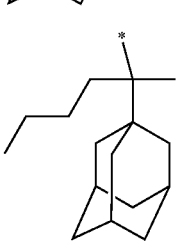

-continued

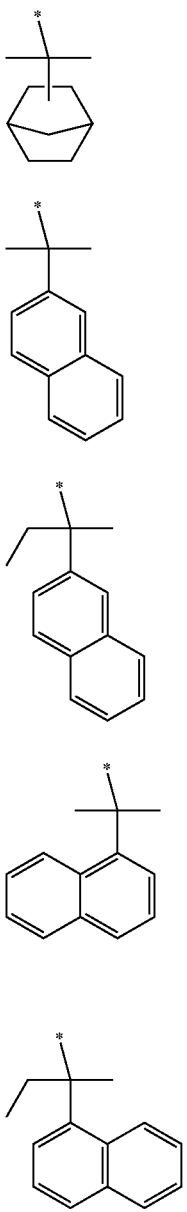

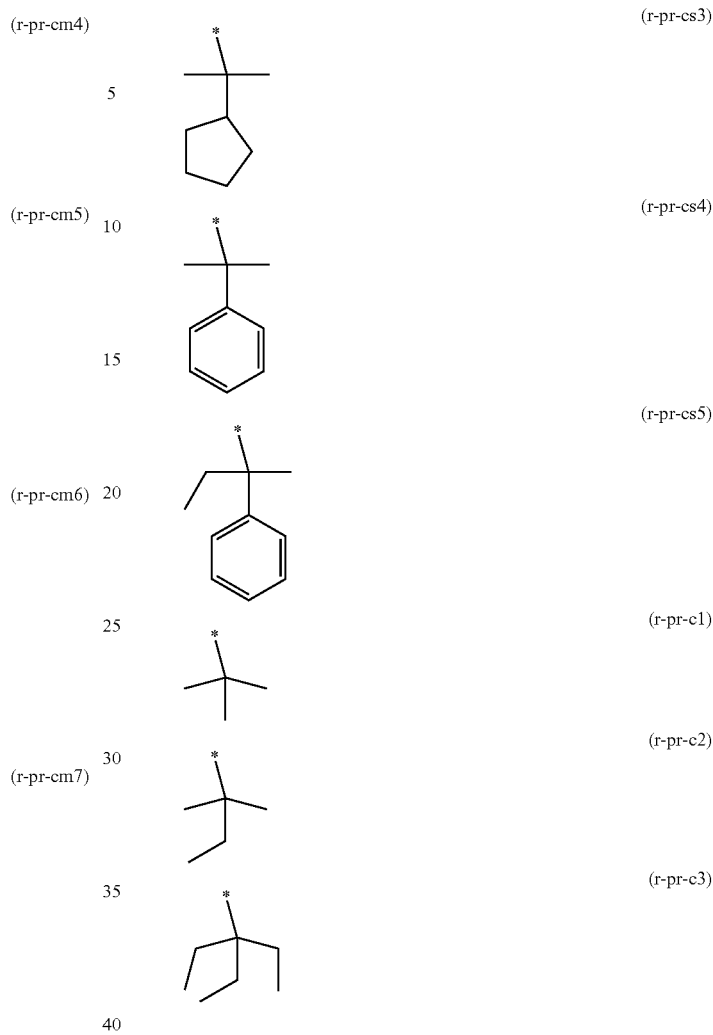

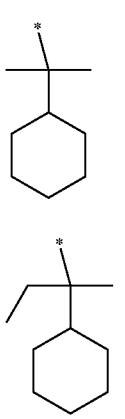

Tertiary Alkyloxycarbonyl Acid Dissociable Group:

Of the above-described polar groups, examples of the acid dissociable group which protects a hydroxyl group include an acid dissociable group represented by the following general formula (a1-r-3) (hereinafter, sometimes referred to as "tertiary alkyloxycarbonyl acid dissociable group" for the sake of convenience).

[Chemical formula 26]

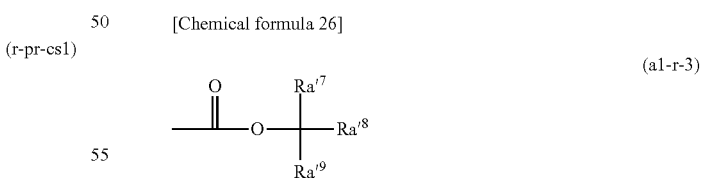

(a1-r-3)

In the formula, each of $Ra'^7$ to $Ra'^9$ represents an alkyl group.

In the formula (a1-r-3), each of $Ra'^7$ to $Ra'^9$ is preferably an alkyl group having 1 to 5 carbon atoms, and more preferably an alkyl group having 1 to 3 carbon atoms.

In addition, the total number of carbon atoms of the respective alkyl groups is preferably 3 to 7, more preferably 3 to 5, and most preferably 3 to 4.

Examples of the constituent unit (a1) include a constituent unit derived from an acrylic ester in which the hydrogen atom bonded to the carbon atom at the α-position may be substituted with a substituent, a constituent unit derived from acrylamide, a constituent unit in which at least some of the hydrogen atoms of the hydroxyl group of a constituent unit derived from hydroxystyrene or a hydroxystyrene derivative are protected by a substituent containing the above-described acid decomposable group, and a constituent unit in which at least some of the hydrogen atoms in —C(=O)—OH of a constituent unit derived from vinylbenzoic acid or a vinylbenzoic acid derivative are protected by a substituent containing the above-described acid decomposable group.

Of the foregoing, the constituent unit (a1) is preferably a constituent unit derived from an acrylic ester in which the hydrogen atom bonded to the carbon atom at the α-position may be substituted with a substituent.

Preferred specific examples of the constituent unit (a1) include a constituent unit represented by the following general formula (a1-1) or (a1-2).

[Chemical formula 27]

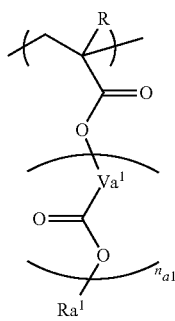

(a1-1)

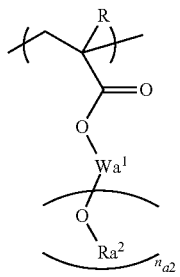

(a1-2)

In the formulae, R represents a hydrogen atom, an alkyl group having 1 to 5 carbon atoms, or a halogenated alkyl group having 1 to 5 carbon atoms; $Va^1$ represents a divalent hydrocarbon group which may have an ether bond; $n_{a1}$ is 0 to 2; $Ra^1$ represents an acid dissociable group represented by the formula (a1-r-1) or (a1-r-2); $Wa^1$ represents an $(n_{a2}+1)$-valent hydrocarbon group; $n_{a2}$ is 1 to 3; and $Ra^2$ represents an acid dissociable group represented by the formula (a0-r-1) or (a1-r-3).

In the formula (a1-1), the alkyl group having 1 to 5 carbon atoms represented by R is preferably a linear or branched alkyl group having 1 to 5 carbon atoms. Specifically, examples thereof include a methyl group, an ethyl group, a propyl group, an isopropyl group, an n-butyl group, an isobutyl group, a tert-butyl group, a pentyl group, an isopentyl group, and a neopentyl group. The halogenated alkyl group having 1 to 5 carbon atoms is a group in which some or all hydrogen atoms of the alkyl group having 1 to 5 carbon atoms are substituted with a halogen atom. Examples of the halogen atom include a fluorine atom, a chlorine atom, a bromine atom, and an iodine atom, with a fluorine atom being especially preferable.

R is preferably a hydrogen atom, an alkyl group having 1 to 5 carbon atoms, or a fluorinated alkyl group having 1 to 5 carbon atoms, and is most preferably a hydrogen atom or a methyl group in terms of easiness in industrial availability.

The hydrocarbon group represented by $Va^1$ may be an aliphatic hydrocarbon group or an aromatic hydrocarbon group. The aliphatic hydrocarbon group means a hydrocarbon group having no aromaticity. The aliphatic hydrocarbon group as a divalent hydrocarbon group in $Va^1$ may be either saturated or unsaturated, and in general, it is preferably saturated.

More specifically, examples of the aliphatic hydrocarbon group in $Va^1$ include a linear or branched aliphatic hydrocarbon group, and an aliphatic hydrocarbon group containing a ring in a structure thereof.

In addition, $Va^1$ may have an ether bond (—O—) between carbon atoms of the divalent hydrocarbon group. One or two or more ether bonds may be present in $Va^1$.

The number of carbon atoms of the linear or branched aliphatic hydrocarbon group is preferably 1 to 10, more preferably 1 to 6, still more preferably 1 to 4, and most preferably 1 to 3.

The linear aliphatic hydrocarbon group is preferably a linear alkylene group. Specifically, examples thereof include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

The branched aliphatic hydrocarbon group is preferably a branched alkylene group. Specifically, examples thereof include an alkylalkylene group such as an alkylmethylene group, for example, —CH($CH_3$)—, —CH($CH_2CH_3$)—, —C($CH_3$)$_2$—, —C($CH_3$)($CH_2CH_3$)—, —C($CH_3$)($CH_2CH_2CH_3$)—, and —C($CH_2CH_3$)$_2$—; an alkylethylene group, for example, —CH($CH_3$)$CH_2$—, —CH($CH_3$)CH($CH_3$)—, —C($CH_3$)$_2CH_2$—, —CH($CH_2CH_3$)$CH_2$—, and —C($CH_2CH_3$)$_2$—$CH_2$—; an alkyltrimethylene group, for example, —CH($CH_3$)$CH_2CH_2$— and —$CH_2$CH($CH_3$)$CH_2$—; and an alkyltetramethylene group, for example, —CH($CH_3$)$CH_2CH_2CH_2$— and —$CH_2$CH($CH_3$)$CH_2CH_2$—. The alkyl group in the alkylalkylene group is preferably a linear alkyl group having 1 to 5 carbon atoms.

Examples of the aliphatic hydrocarbon group containing a ring in a structure thereof include an alicyclic hydrocarbon group (a group in which two hydrogen atoms are eliminated from an aliphatic hydrocarbon ring), a group in which an alicyclic hydrocarbon group is bonded to the terminal of a linear or branched aliphatic hydrocarbon group, and a group in which an alicyclic hydrocarbon group intervenes on the way of a linear or branched aliphatic hydrocarbon group. Examples of the linear or branched aliphatic hydrocarbon group include the same groups as those described above.

The alicyclic hydrocarbon group has preferably 3 to 20 carbon atoms, and more preferably 3 to 12 carbon atoms.

The alicyclic hydrocarbon group may be either a polycyclic group or a monocyclic group. The monocyclic alicyclic hydrocarbon group is preferably a group in which two hydrogen atoms are eliminated from a monocycloalkane. The monocycloalkane is preferably one having 3 to 6 carbon atoms. Specifically, examples thereof include cyclopentane and cyclohexane.

The polycyclic alicyclic hydrocarbon group is preferably a group in which two hydrogen atoms are eliminated from a polycycloalkane. The polycycloalkane is preferably one having 7 to 12 carbon atoms. Specifically, examples thereof include adamantane, norbornane, isobornane, tricyclodecane, and tetracyclododecane.

The aromatic hydrocarbon group in $Va^1$ is a hydrocarbon group having at least one aromatic ring. This aromatic ring is not particularly limited so long as it is a cyclic conjugated system having $(4n+2)\pi$ electrons, and it may be either monocyclic or polycyclic. The number of carbon atoms of the aromatic ring is preferably 5 to 30, more preferably 5 to 20, still more preferably 6 to 15, and especially preferably 6 to 12. Specifically, examples of the aromatic ring include an aromatic hydrocarbon ring such as benzene, naphthalene, anthracene, and phenanthrene; and an aromatic heterocyclic ring in which some of the carbon atoms constituting the above-described aromatic hydrocarbon ring are substituted with a hetero atom. Examples of the hetero atom in the aromatic heterocyclic ring include an oxygen atom, a sulfur atom, and a nitrogen atom. Specifically, examples of the aromatic heterocyclic ring include a pyridine ring and a thiophene ring.

Specifically, examples of the aromatic hydrocarbon group include a group in which two hydrogen atoms are eliminated from the above-described aromatic hydrocarbon ring or aromatic heterocyclic ring (an arylene group or a heteroarylene group); a group in which two hydrogen atoms are eliminated from an aromatic compound containing two or more aromatic rings (for example, biphenyl or fluorene); and a group in which one hydrogen atom of a group in which one hydrogen atom is eliminated from the above-described aromatic hydrocarbon ring or aromatic heterocyclic ring (an aryl group or a heteroaryl group) is substituted with an alkylene group (for example, a group in which one hydrogen atom is further eliminated from an aryl group in an arylalkyl group such as a benzyl group, a phenethyl group, a 1-naphthylmethyl group, a 2-naphthylmethyl group, a 1-naphthylethyl group, and a 2-naphthylethyl group). The number of carbon atoms of the alkylene group bonded to the above-described aryl group or heteroaryl group is preferably 1 to 4, more preferably 1 to 2, and especially preferably 1.

In the formula (a1-2), the $(n_{a2}+1)$-valent hydrocarbon group in $Wa^1$ may be an aliphatic hydrocarbon group or an aromatic hydrocarbon group. The aliphatic hydrocarbon group means a hydrocarbon group having no aromaticity. The aliphatic hydrocarbon group may be either saturated or unsaturated, and in general, it is preferably saturated. Examples of the aliphatic hydrocarbon group include a linear or branched aliphatic hydrocarbon group, an aliphatic hydrocarbon group containing a ring in a structure thereof, and a group in which a linear or branched aliphatic hydrocarbon group and an aliphatic hydrocarbon group containing a ring in a structure thereof are combined.

The valence of $(n_{a2}+1)$ is preferably divalent to tetravalent, and more preferably divalent or trivalent.

Specific examples of the constituent unit represented by the formula (a1-1) are given below. In each of the following formulae, $R^\alpha$ represents a hydrogen atom, a methyl group, or a trifluoromethyl group.

[Chemical formula 28]

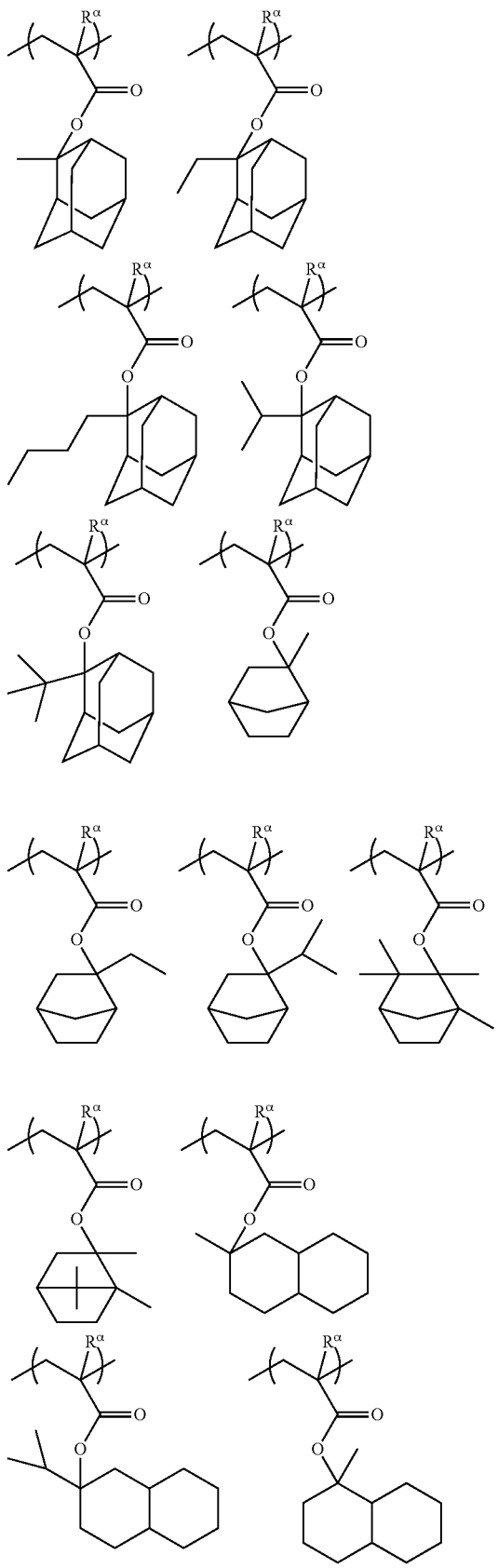

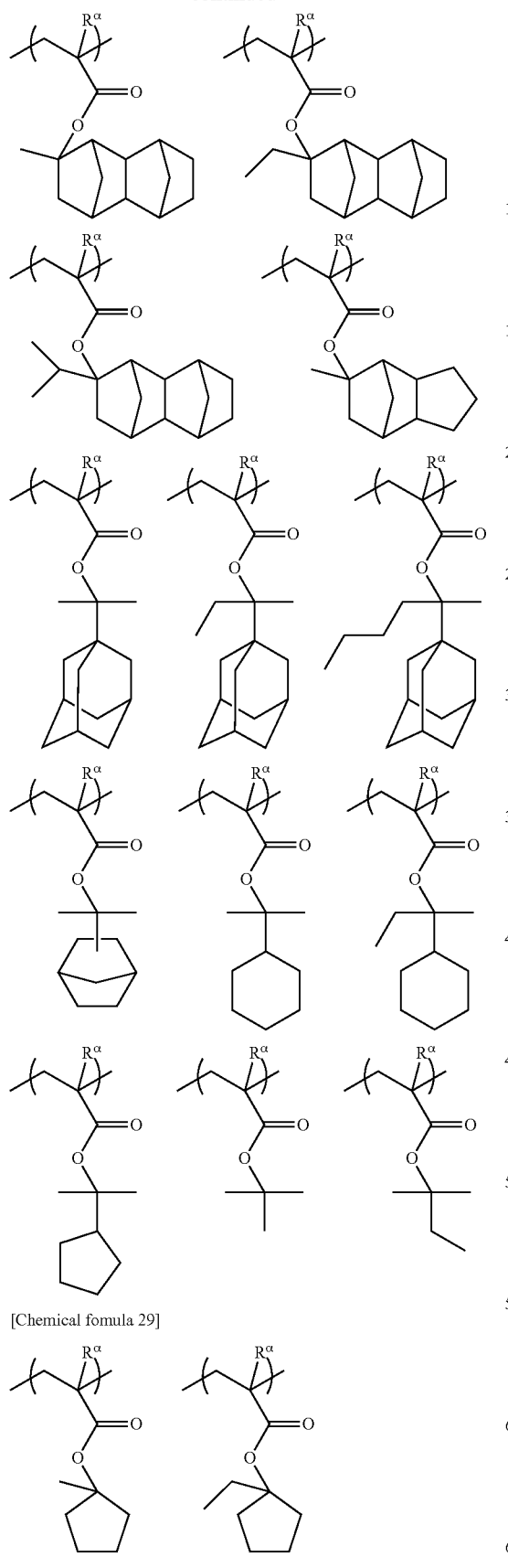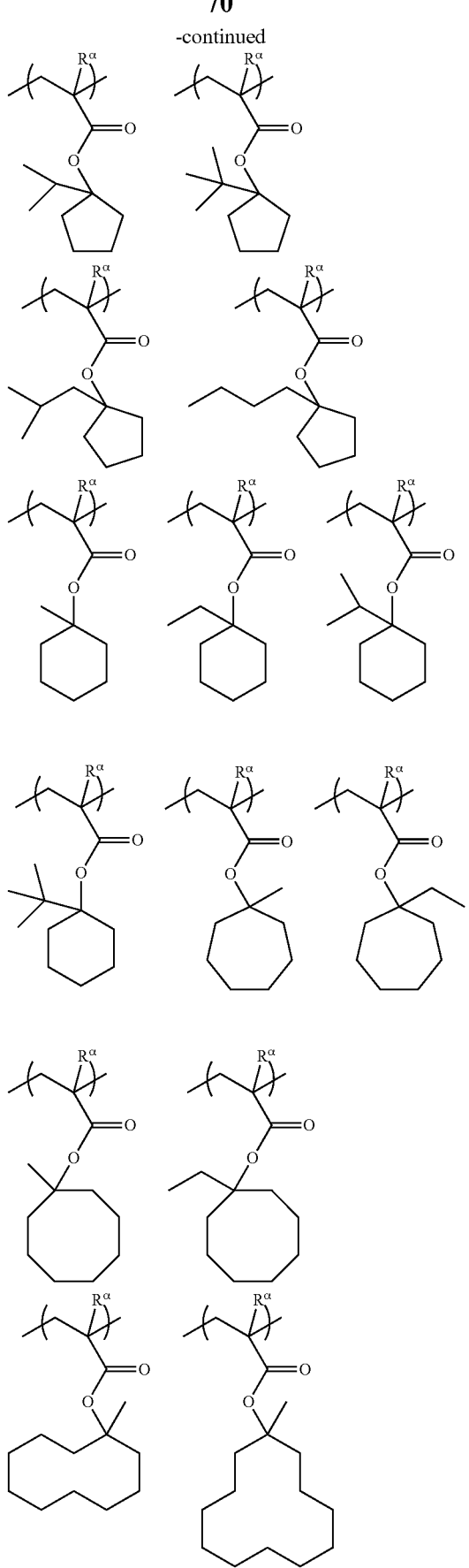

[Chemical formula 30]
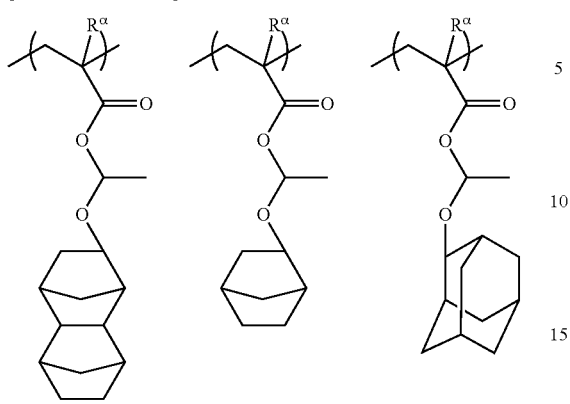
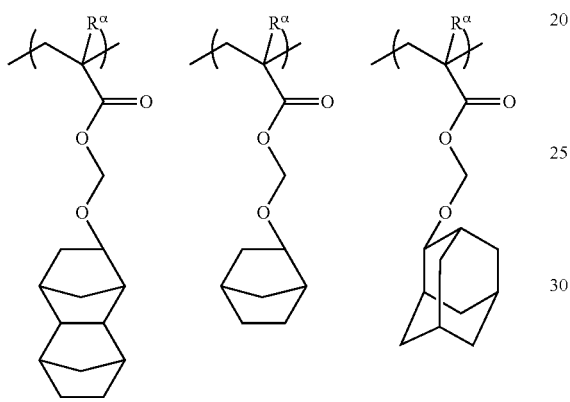
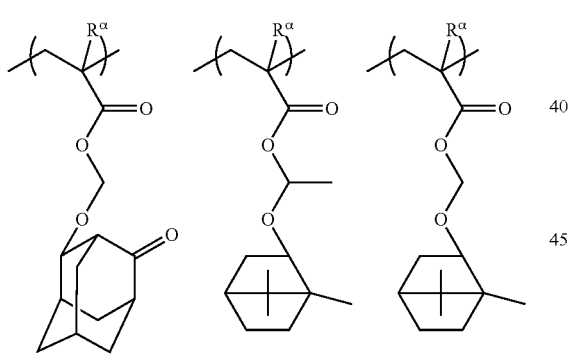
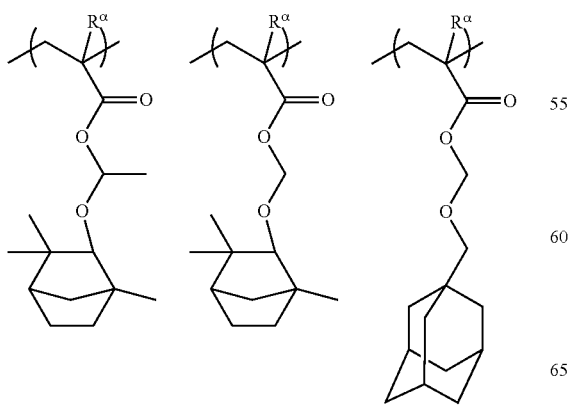
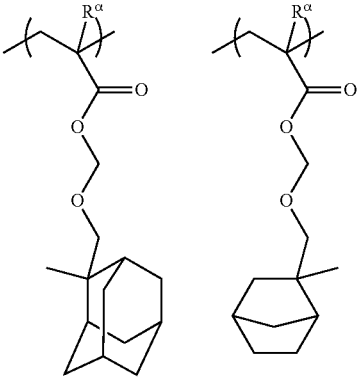
[Chemical formula 31]
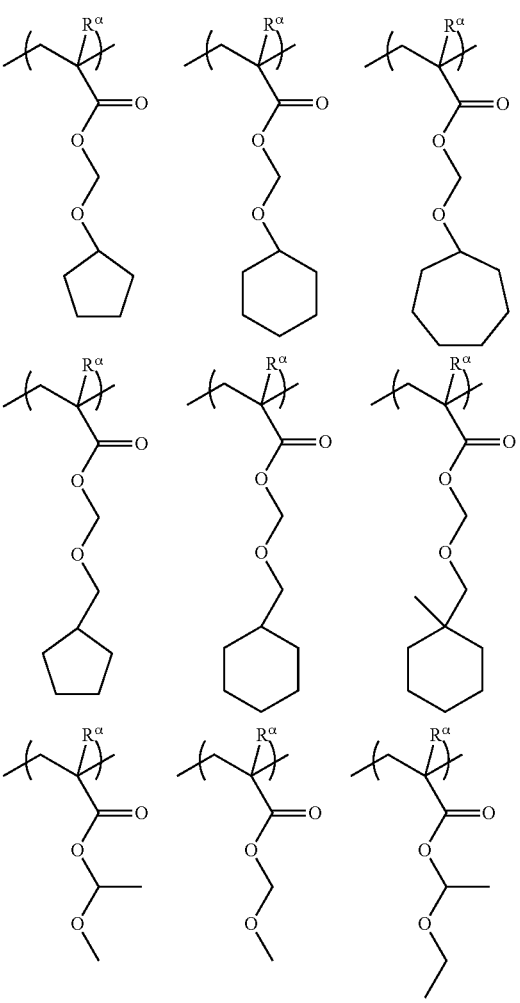
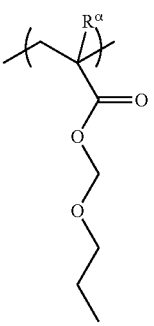

-continued
[Chemical formula 32]
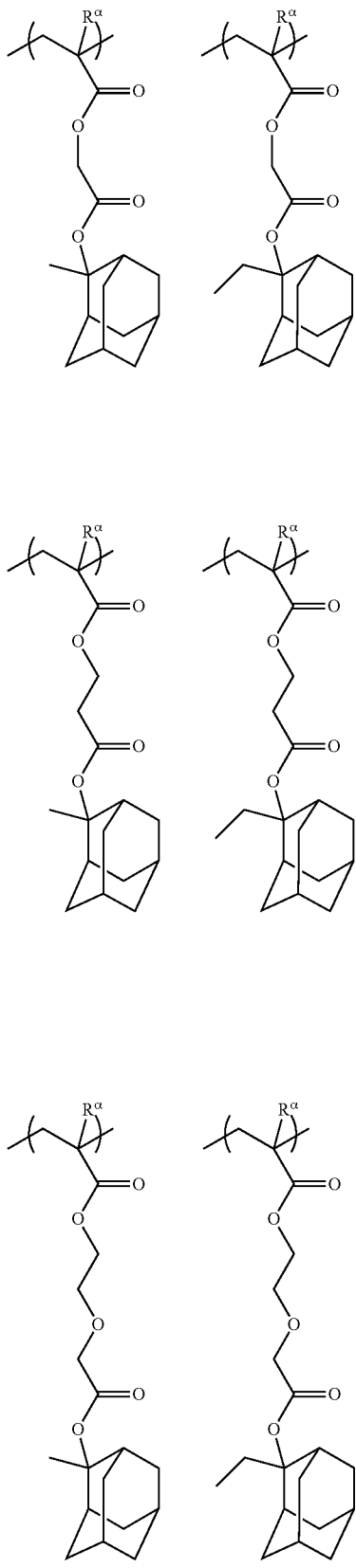
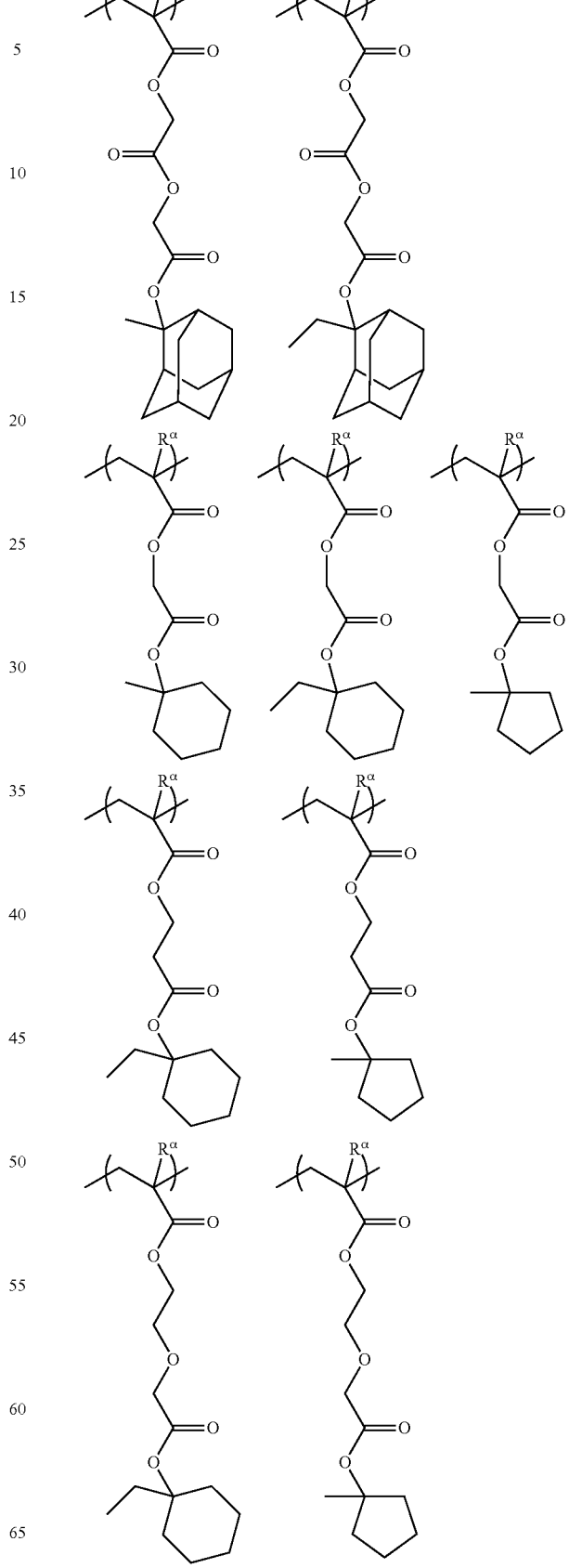

-continued

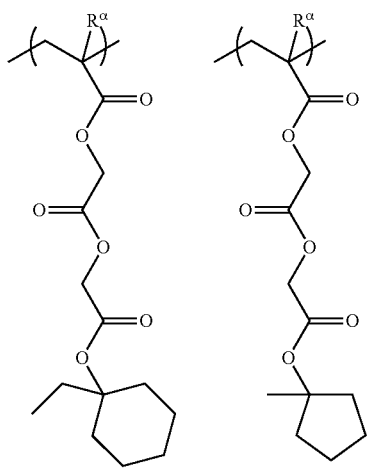

Specific examples of the constituent unit represented by the formula (a1-2) are given below.

[Chemical formula 33]

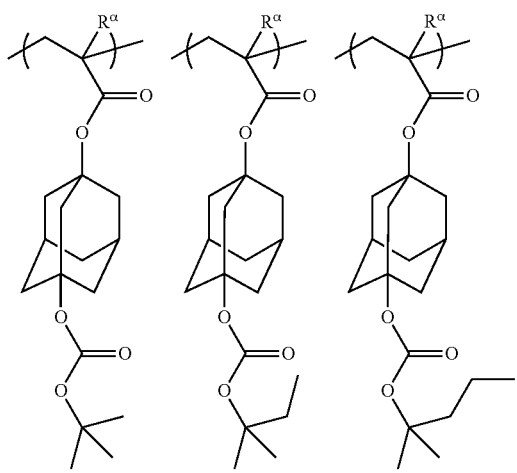

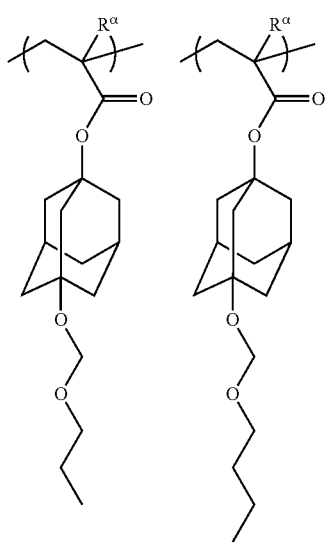

-continued

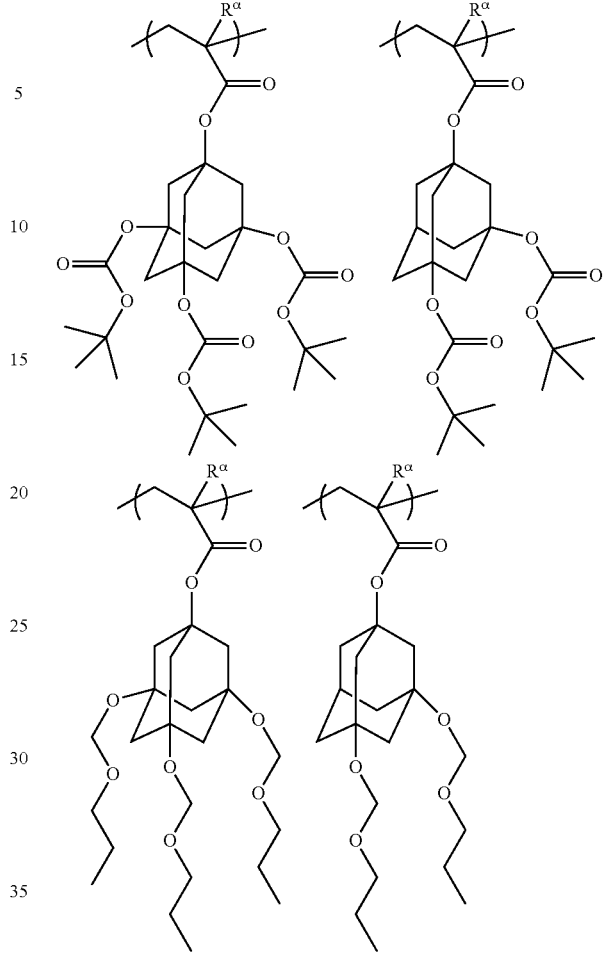

The constituent unit (a1) which the component (A1) has may be either one kind or two or more kinds.

When the component (A1) has the constituent unit (a1), a proportion of the constituent unit (a1) in the component (A1) is preferably 1 mol % to 50 mol %, more preferably 5 mol % to 45 mol %, and still more preferably 5 mol % to 40 mol % relative to a total sum of all of the constituent units constituting the component (A1)

When the proportion of the constituent unit (a1) is the preferred lower limit value or more, a resist pattern can be easily obtained, and thus lithography properties such as sensitivity, resolution, an improvement of roughness, and an EL margin are also enhanced. When the proportion of the constituent unit (a1) is not more than the preferred upper limit value, a balance with other constituent units can be taken.

Constituent Unit (a2)

In the resist composition (1), the component (A1) preferably further has a constituent unit (a2) containing a lactone-containing cyclic group, an —$SO_2$—-containing cyclic group, or a carbonate-containing cyclic group, in addition to the constituent unit (a0) and the constituent unit (a1).

In the case of using the component (A1) for the formation of a resist film, the lactone-containing cyclic group, the —$SO_2$—-containing cyclic group, or the carbonate-containing cyclic group of the constituent unit (a2) is effective for increasing the adhesiveness of the resist film to a substrate.

The term "lactone-containing cyclic group" refers to a cyclic group containing a ring (lactone ring) containing —O—C(=O)— in a ring skeleton thereof. When the lactone ring is counted as the first ring, a lactone-containing cyclic group in which the only ring structure is the lactone ring is called a monocyclic group, whereas a lactone-containing cyclic group containing other ring structure is called a polycyclic group regardless of the structure of the other rings. The lactone-containing cyclic group may be either a monocyclic group or a polycyclic group.

The lactone-containing cyclic group in the constituent unit (a2) is not particularly limited, and any optional lactone-containing cyclic group can be used. Specifically, examples thereof include groups represented by the following general formulae (a2-r-1) to (a2-r-7), respectively.

[Chemical formula 34]

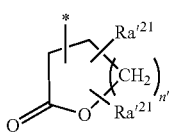
(a2-r-1)

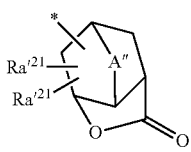
(a2-r-2)

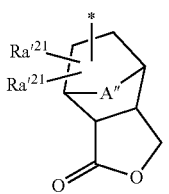
(a2-r-3)

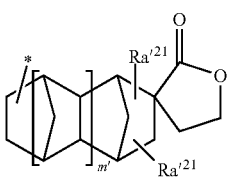
(a2-r-4)

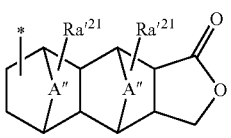
(a2-r-5)

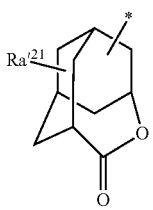
(a2-r-6)

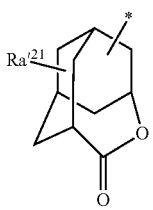
(a2-r-7)

In the formulae, each $Ra'^{21}$ independently represents a hydrogen atom, an alkyl group, an alkoxy group, a halogen atom, a halogenated alkyl group, a hydroxyl group, —COOR", —OC(=O)R", a hydroxyalkyl group, or a cyano group; R" represents a hydrogen atom, an alkyl group, a lactone-containing cyclic group, a carbonate-containing cyclic group, or a —SO$_2$—-containing cyclic group; A" represents an alkylene group having 1 to 5 carbon atoms, which may contain an oxygen atom (—O—) or a sulfur atom (—S—), an oxygen atom, or a sulfur atom; n' represents an integer of 0 to 2; and m' represents 0 or 1.

In the general formulae (a2-r-1) to (a2-r-7), the alkyl group in $Ra'^{21}$ is preferably an alkyl group having 1 to 6 carbon atoms. The alkyl group is preferably linear or branched. Specifically, examples thereof include a methyl group, an ethyl group, a propyl group, an isopropyl group, an n-butyl group, an isobutyl group, a tert-butyl group, a pentyl group, an isopentyl group, a neopentyl group, and a hexyl group. Of these, a methyl group or an ethyl group is preferable, with a methyl group being especially preferable.

The alkoxy group in $Ra'^{21}$ is preferably an alkoxy group having 1 to 6 carbon atoms. The alkoxy group is preferably linear or branched. Specifically, examples thereof include a group in which the alkyl group exemplified above as the alkyl group in $Ra'^{21}$ and an oxygen atom (—O—) are connected to each other.

Examples of the halogen atom in $Ra'^{21}$ include a fluorine atom, a chlorine atom, a bromine atom, and an iodine atom, with a fluorine atom being preferable.

Examples of the halogenated alkyl group in $Ra'^{21}$ include a group in which some or all hydrogen atoms of the alkyl group in $Ra'^{21}$ are substituted with a halogen atom. The halogenated alkyl group is preferably a fluorinated alkyl group, and especially preferably a perfluoroalkyl group.

In —COOR" and —OC(=O)R" in $Ra'^{21}$, each R" is a hydrogen atom, an alkyl group, a lactone-containing cyclic group, a carbonate-containing cyclic group, or a —SO$_2$—-containing cyclic group.

The alkyl group in R" may be linear, branched, or cyclic, and the number of carbon atoms thereof is preferably 1 to 15.

In the case where R" is a linear or branched alkyl group, the number of carbon atoms thereof is preferably 1 to 10, and more preferably 1 to 5. Above all, R" is especially preferably a methyl group or an ethyl group.

In the case where R" is a cyclic alkyl group, the number of carbon atoms thereof is preferably 3 to 15, more preferably 4 to 12, and most preferably 5 to 10. Specifically, examples thereof include a group in which one or more hydrogen atoms are eliminated from a monocycloalkane, which may or may not be substituted with a fluorine atom or a fluorinated alkyl group; and a group in which one or more hydrogen atoms are eliminated from a polycycloalkane such as a bicycloalkane, a tricycloalkane, and a tetracycloalkane. More specifically, examples thereof include a group in which one or more hydrogen atoms are eliminated from a monocycloalkane such as cyclopentane and cyclohexane; and a group in which one or more hydrogen atoms are eliminated from a polycycloalkane such as adamantane, norbornane, isobornane, tricyclodecane, and tetracyclododecane.

Examples of the lactone-containing cyclic group in R" include the same groups as those represented by the general formulae (a2-r-1) to (a2-r-7), respectively.

The carbonate-containing cyclic group in R" is the same as a carbonate-containing cyclic group to be described later. Specifically, examples thereof include groups represented by general formulae (ax3-r-1) to (ax3-r-3), respectively.

The —SO$_2$—-containing cyclic group in R" is the same as a —SO$_2$—-containing cyclic group to be described later.

Specifically, examples thereof include groups represented by general formulae (a5-r-1) to (a5-r-4), respectively.

The hydroxyalkyl group in Ra'$^{21}$ is preferably one having 1 to 6 carbon atoms. Specifically, examples thereof include a group in which at least one hydrogen atom of the alkyl group in Ra'$^{21}$ is substituted with a hydroxyl group.

In the formulae (a2-r-2), (a2-r-3), and (a2-r-5), the alkylene group having 1 to 5 carbon atoms in A" is preferably a linear or branched alkylene group, and examples thereof include a methylene group, an ethylene group, an n-propylene group, and an isopropylene group. In the case where the alkylene group contains an oxygen atom or a sulfur atom, specific examples thereof include a group in which —O— or —S— intervenes at the terminal or between the carbon atoms of the above-described alkylene group. Examples thereof include —O—CH$_2$—, —CH$_2$—O—CH$_2$—, —S—CH$_2$—, and —CH$_2$—S—CH$_2$—. A" is preferably an alkylene group having 1 to 5 carbon atoms or —O—, more preferably an alkylene group having 1 to 5 carbon atoms, and most preferably a methylene group.

Specific examples of each of the groups represented by the general formulae (a2-r-1) to (a2-r-7) are given below.

[Chemical formula 35]

(r-lc-1-1)

(r-lc-1-2)

(r-lc-1-3)

(r-lc-1-4)

(r-lc-1-5)

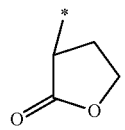

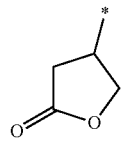

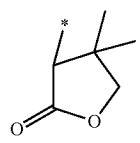

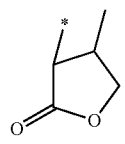

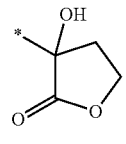

(r-lc-1-6)

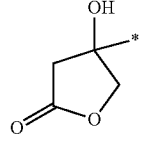

-continued (r-lc-1-7)

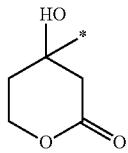

(r-lc-2-1)

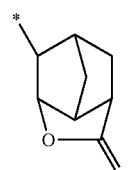

(r-lc-2-2)

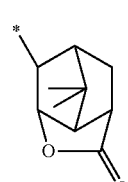

(r-lc-2-3)

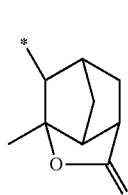

(r-lc-2-4)

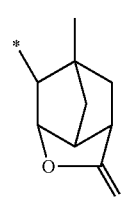

(r-lc-2-5)

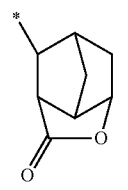

(r-lc-2-6)

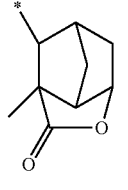

(r-lc-2-7)

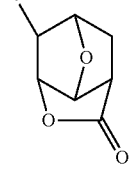

(r-lc-2-8)
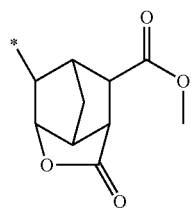
(r-lc-2-9)
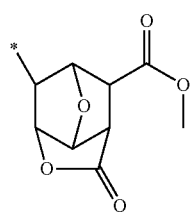
(r-lc-2-10)
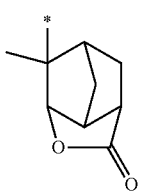
(r-lc-2-11)
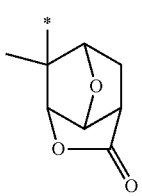
(r-lc-2-12)
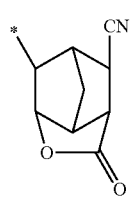
(r-lc-2-13)
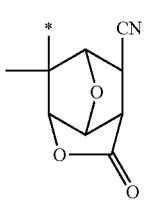
(r-lc-2-14)
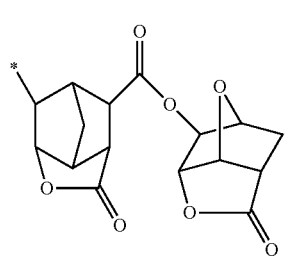
(r-lc-2-15)
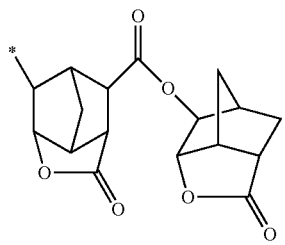
(r-lc-2-16)
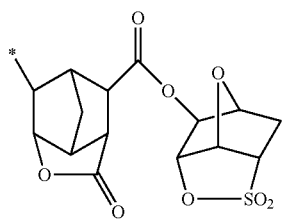
(r-lc-2-17)
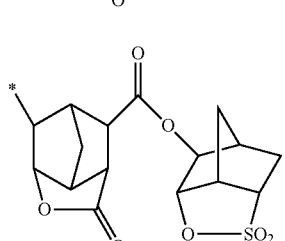
(r-lc-2-18)
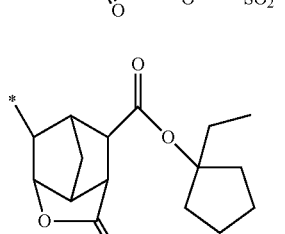
(r-lc-3-1)
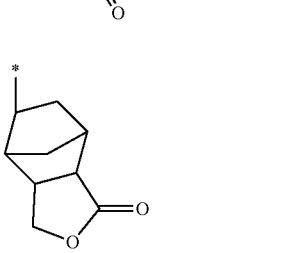
(r-lc-3-2)
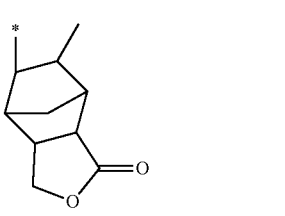
(r-lc-3-3)
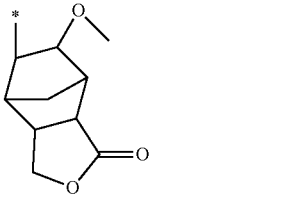

(r-lc-3-4)
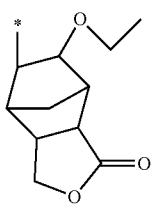
(r-lc-3-5)
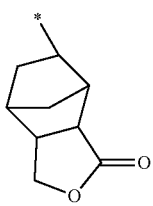
[Chemical formula 36]
(r-lc-4-1)
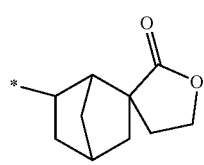
(r-lc-4-2)
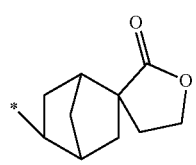
(r-lc-4-3)
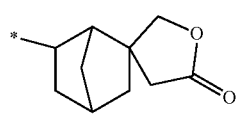
(r-lc-4-4)
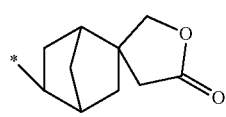
(r-lc-4-5)
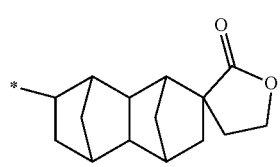
(r-lc-4-6)
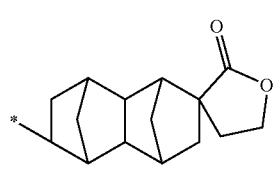
(r-lc-4-7)
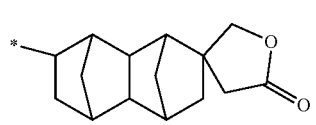
(r-lc-4-8)
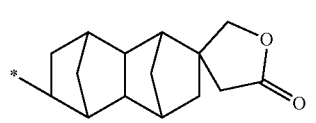
(r-lc-4-9)
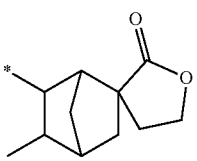
(r-lc-5-1)
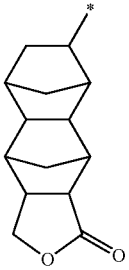
(r-lc-5-2)
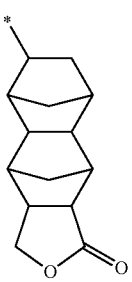
(r-lc-5-3)
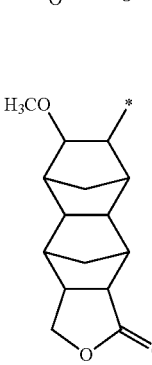
(r-lc-5-4)
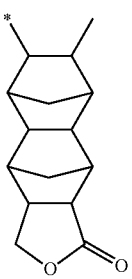
(r-lc-6-1)
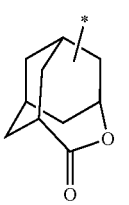

-continued (r-lc-7-1)

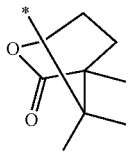

The term "—SO$_2$—-containing cyclic group" refers to a cyclic group containing a ring containing —SO$_2$— in a ring skeleton thereof, and specifically, it is a cyclic group in which the sulfur atom (S) in —SO$_2$— forms a part of the ring skeleton of the cyclic group. When the ring containing —SO$_2$— in the ring skeleton thereof is counted as the first ring, an —SO$_2$—-containing cyclic group in which the only ring structure is the —SO$_2$—-containing ring is called a monocyclic group, whereas an —SO$_2$—-containing cyclic group containing other ring structure is called a polycyclic group regardless of the structure of the other rings. The —SO$_2$—-containing cyclic group may be either a monocyclic group or a polycyclic group.

The —SO$_2$—-containing cyclic group is especially preferably a cyclic group containing —O—SO$_2$— in a ring skeleton thereof, namely a cyclic group containing a sultone ring in which —O—S— in —O—SO$_2$— forms a part of the ring skeleton.

More specifically, examples of the —SO$_2$—-containing cyclic group include groups represented by the following general formulae (a5-r-1) to (a5-r-4), respectively.

[Chemical formula 37]

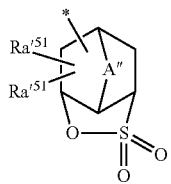
(a5-r-1)

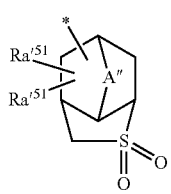
(a5-r-2)

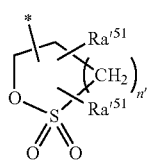
(a5-r-3)

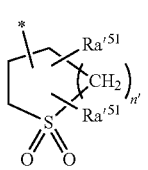
(a5-r-4)

In the formulae, each Ra'$^{15}$ independently represents a hydrogen atom, an alkyl group, an alkoxy group, a halogen atom, a halogenated alkyl group, a hydroxyl group, —COOR", —OC(=O)R", a hydroxyalkyl group, or a cyano group; R" represents a hydrogen atom, an alkyl group, a lactone-containing cyclic group, a carbonate-containing cyclic group, or a —SO$_2$—-containing cyclic group; A" represents an alkylene group having 1 to 5 carbon atoms, which may contain an oxygen atom or a sulfur atom, an oxygen atom, or a sulfur atom; and n' represents an integer of 0 to 2.

In the general formulae (a5-r-1) to (a5-r-4), A" is the same as A" in the general formulae (a2-r-2), (a2-r-3), and (a2-r-5).

The alkyl group, the alkoxy group, the halogen atom, the halogenated alkyl group, —COOR", —OC(=O)R", and the hydroxyalkyl group in Ra'$^{51}$ are the same as those exemplified in the description of Ra'$^{21}$ in the general formulae (a2-r-1) to (a2-r-7).

Specific examples of each of the groups represented by the general formulae (a5-r-1) to (a5-r-4) are given below. In the following formulae, "Ac" represents an acetyl group.

[Chemical formula 38]

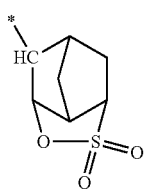
(r-sl-1-1)

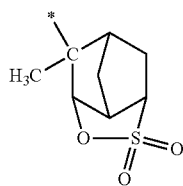
(r-sl-1-2)

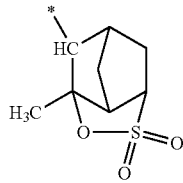
(r-sl-1-3)

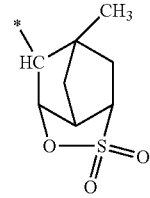
(r-sl-1-4)

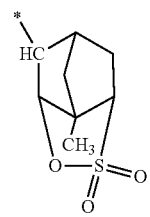
(r-sl-1-5)

(r-sl-1-6)
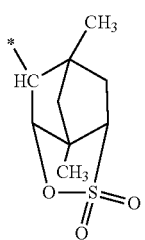
(r-sl-1-7)
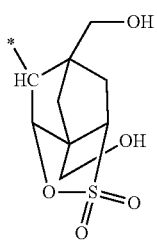
(r-sl-1-8)
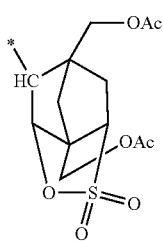
(r-sl-1-9)
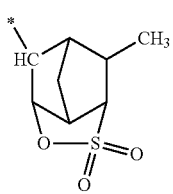
(r-sl-1-10)
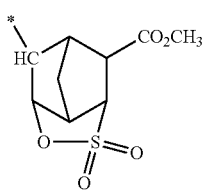
(r-sl-1-11)
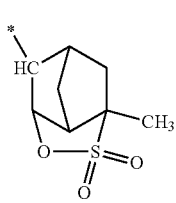
(r-sl-1-12)
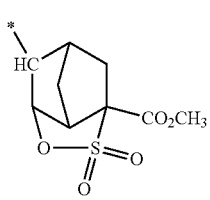
(r-sl-1-13)
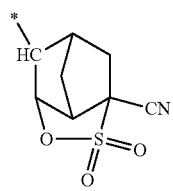
(r-sl-1-14)
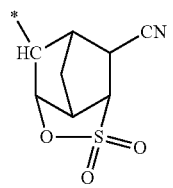
(r-sl-1-15)
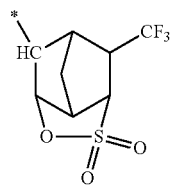
(r-sl-1-16)
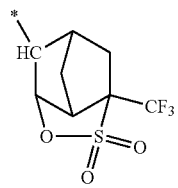
(r-sl-1-17)
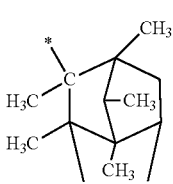
(r-sl-1-18)
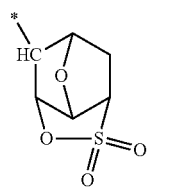
(r-sl-1-19)
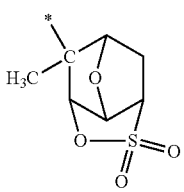
(r-sl-1-20)
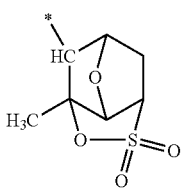

(r-sl-1-21)
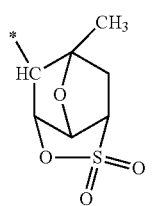
[Chemical formula 39]
(r-sl-1-22)
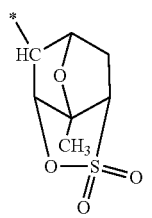
(r-sl-1-23)
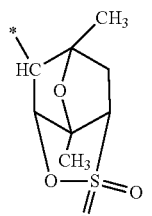
(r-sl-1-24)
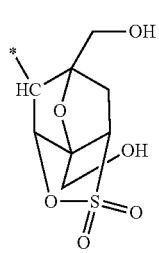
(r-sl-1-25)
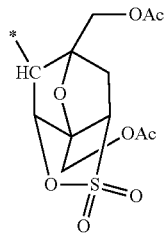
(r-sl-1-26)
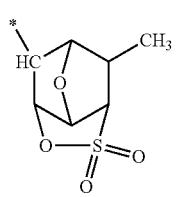
(r-sl-1-27)
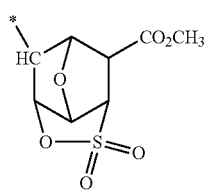
(r-sl-1-28)
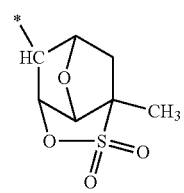
(r-sl-1-29)
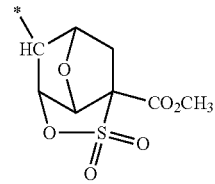
(r-sl-1-30)
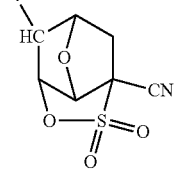
(r-sl-1-31)
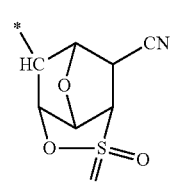
(r-sl-1-32)
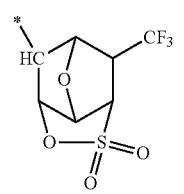
(r-sl-1-33)
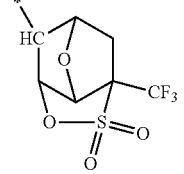
[Chemical formula 40]
(r-sl-2-1)
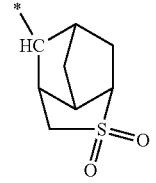
(r-sl-2-2)
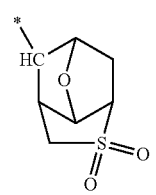

-continued (r-sl-3-1)

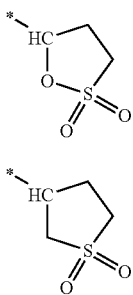

(r-sl-4-1)

The term "carbonate-containing cyclic group" refers to a cyclic group containing a ring containing —O—C(=O)—O— in a ring skeleton thereof (carbonate ring). When the carbonate ring is counted as the first ring, a carbonate-containing cyclic group in which the only ring structure is the carbonate ring is called a monocyclic group, whereas a carbonate-containing cyclic group containing other ring structure is called a polycyclic group regardless of the structure of the other rings. The carbonate-containing cyclic group may be either a monocyclic group or a polycyclic group.

The carbonate ring-containing cyclic group is not particularly limited, and any optional carbonate ring-containing cyclic group can be used. Specifically, examples thereof include groups represented by the following general formulae (ax3-r-1) to (ax3-r-3), respectively.

[Chemical formula 41]

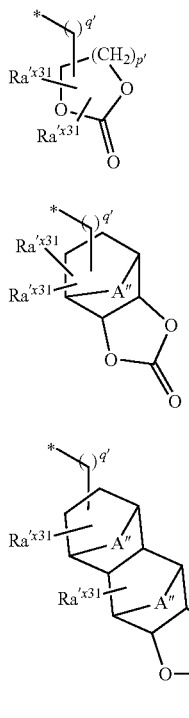

(ax3-r-1)

(r-sl-3-2)

(r-sl-3-3)

In the formulae, each $Ra'^{x31}$ independently represents a hydrogen atom, an alkyl group, an alkoxy group, a halogen atom, a halogenated alkyl group, a hydroxyl group, —COOR", —OC(=O)R", a hydroxyalkyl group, or a cyano group; R" represents a hydrogen atom, an alkyl group, a lactone-containing cyclic group, a carbonate-containing cyclic group, or a —SO$_2$—-containing cyclic group; A" represents an alkylene group having 1 to 5 carbon atoms, which may contain an oxygen atom or a sulfur atom, an oxygen atom, or a sulfur atom; p' represents an integer of 0 to 3; and q' represents 0 or 1.

A" in the general formulae (ax3-r-1) to (ax3-r-3) is the same as A" in the general formulae (a2-r-2), (a2-r-3), and (a2-r-5).

The alkyl group, the alkoxy group, the halogen atom, the halogenated alkyl group, —COOR", —OC(=O)R", and the hydroxyalkyl group in $Ra'^{x31}$ are the same as those exemplified in the description of $Ra'^{21}$ in the general formulae (a2-r-1) to (a2-r-7), respectively.

Specific examples of each of the groups represented by the general formulae (ax3-r-1) to (ax3-r-3) are given below.

[Chemical formula 42]

(r-cr-1-1)

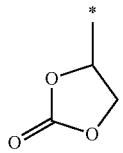

(r-cr-1-2)

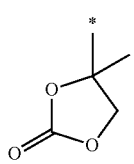

(r-cr-1-3)

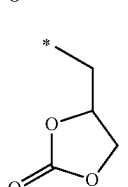

(r-cr-1-4)

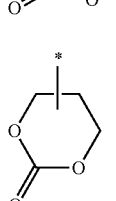

(r-cr-1-5)

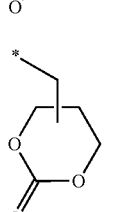

(r-cr-1-6)

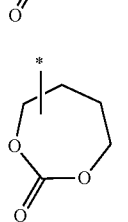

(r-cr-1-7)
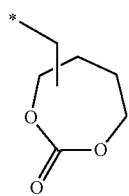
(r-cr-2-1)
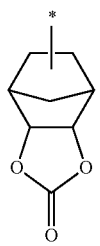
(r-cr-2-2)
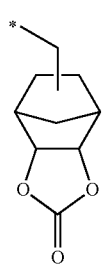
(r-cr-2-3)
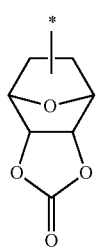
(r-cr-2-4)
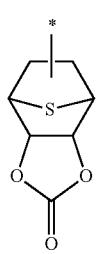
(r-cr-3-1)
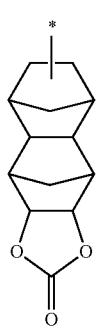
(r-cr-3-2)
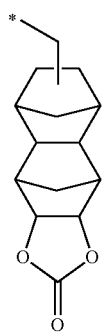
(r-cr-3-3)
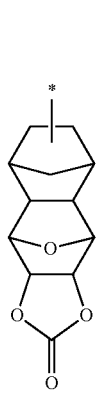
(r-cr-3-4)
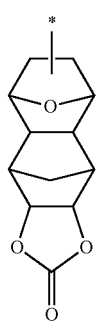
(r-cr-3-5)
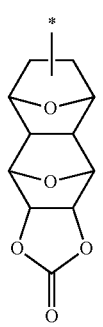
Of the foregoing, the constituent unit (a2) is preferably a constituent unit derived from an acrylic ester in which the hydrogen atom bonded to the carbon atom at the α-position may be substituted with a substituent.
Such a constituent unit (a2) is preferably a constituent unit represented by the following general formula (a2-1).

[Chemical formula 43]

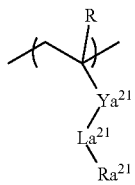

(a2-1)

In the formula, R represents a hydrogen atom, an alkyl group having 1 to 5 carbon atoms, or a halogenated alkyl group having 1 to 5 carbon atoms; $Ya^{21}$ represents a single bond or a divalent linking group; $La^{21}$ represents —O—, —COO—, —CON(R')—, —OCO—, —CONHCO—, or —CONHCS—; R' represents a hydrogen atom or a methyl group, provided that in the case where $La^{21}$ is —O—, $Ya^{21}$ is not —CO—; and $Ra^{21}$ represents a lactone-containing cyclic group, a carbonate-containing cyclic group, or an —$SO_2$—-containing cyclic group.

In the formula (a2-1), R is the same as that described above.

Though the divalent linking group represented by $Ya^{21}$ is not particularly limited, preferred examples thereof include an optionally substituted divalent hydrocarbon group and a divalent linking group containing a hetero atom.

Examples of the optionally substituted divalent hydrocarbon group in $Ya^{21}$ include the same optionally substituted divalent hydrocarbon group as that in $Ya^{01}$ in the formula (a0-1).

Examples of the divalent linking group containing a hetero atom in $Ya^{21}$ include the same divalent linking group containing a hetero atom as that in $Ya^{01}$ in the formula (a0-1).

$Ya^{21}$ is preferably a single bond, an ester bond [—C(=O)—O—], an ether bond (—O—), a linear or branched alkylene group, or a combination thereof.

In the formula (a2-1), $Ra^{21}$ is a lactone-containing cyclic group, a —$SO_2$—-containing cyclic group, or a carbonate-containing cyclic group.

Preferred examples of the lactone-containing cyclic group, the —$SO_2$—-containing cyclic group, and the carbonate-containing cyclic group in $Ra^{21}$ include the groups represented by the general formulae (a2-r-1) to (a2-r-7), the groups represented by the general formulae (a5-r-1) to (a5-r-4), and the groups represented by the general formulae (ax3-r-1) to (ax3-r-3), respectively.

Above all, the lactone-containing cyclic group or the —$SO_2$—-containing cyclic group is preferable, and the groups represented by each of the general formulae (a2-r-1), (a2-r-2) and (a5-r-1), respectively, are more preferable. Specifically, any one of the groups represented by the chemical formulae (r-lc-1-1) to (r-lc-1-7), (r-lc-2-1) to (r-lc-2-18), (r-sl-1-1), and (r-sl-1-18) is more preferable.

The constituent unit (a2) which the component (A1) has may be either one kind or two or more kinds.

When the component (A1) has the constituent unit (a2), a proportion of the constituent unit (a2) is preferably 1 mol % to 80 mol %, more preferably 10 mol % to 70 mol %, still more preferably 10 mol % to 65 mol %, and especially preferably 10 mol % to 60 mol % relative to a total sum of all of the constituent units constituting the component (A1).

When the proportion of the constituent unit (a2) is the preferred lower limit value or more, the effects due to the fact that the constituent unit (a2) is contained are sufficiently obtained. When the proportion of the constituent unit (a2) is not more than the preferred upper limit value, a balance with other constituent units can be taken, and various lithography properties and the pattern shape are enhanced.

Constituent Unit (a3)

The constituent unit (a3) is a constituent unit containing a polar group-containing aliphatic hydrocarbon group (exclusive of those which fall within the definition of the constituent unit (a0), (a1), or (a2)).

In view of the fact that the component (A1) has the constituent unit (a3), the hydrophilicity of the component (A) increases, resulting in contribution to an enhancement of resolution.

Examples of the polar group include a hydroxyl group, a cyano group, a carboxy group, and a hydroxyalkyl group in which some of hydrogen atoms of an alkyl group are substituted with a fluorine atom, with a hydroxyl group being especially preferable.

Examples of the aliphatic hydrocarbon group include a linear or branched hydrocarbon group having 1 to 10 carbon atoms (preferably an alkylene group) and a cyclic aliphatic hydrocarbon group (cyclic group). The cyclic group may be either a monocyclic group or a polycyclic group, and for example, it can be properly selected and used among a large number of groups proposed in resins of resist compositions for ArF excimer lasers. The cyclic group is preferably a polycyclic group, and more preferably a polycyclic group having 7 to 30 carbon atoms.

Above all, a constituent unit derived from an acrylic ester containing an aliphatic polycyclic group containing a hydroxyl group, a cyano group, a carboxy group, or a hydroxyalkyl group in which some of hydrogen atoms of an alkyl group are substituted with a fluorine atom is more preferable. Examples of the polycyclic group include a group in which two or more hydrogen atoms are eliminated from a bicycloalkane, a tricycloalkane, a tetracycloalkane, or the like. Specifically, examples thereof include a group in which two or more hydrogen atoms are eliminated from a polycycloalkane such as adamantane, norbornane, isobornane, tricyclodecane, and tetracyclododecane. Among these polycyclic groups, a group in which two or more hydrogen atoms are eliminated from adamantane, a group in which two or more hydrogen atoms are eliminated from norbornane, or a group in which two or more hydrogen atoms are eliminated from tetracyclododecane is preferable from the industrial standpoint.

As the constituent unit (a3), an arbitrary constituent unit can be used without particular limitations so long as it contains a polar group-containing aliphatic hydrocarbon group.

The constituent unit (a3) is preferably a constituent unit derived from an acrylic ester in which the hydrogen atom bonded to the carbon atom at the α-position may be substituted with a substituent, the constituent unit containing a polar group-containing aliphatic hydrocarbon group.

When the hydrocarbon group in the polar group-containing aliphatic hydrocarbon group is a linear or branched hydrocarbon group having 1 to 10 carbon atoms, the constituent unit (a3) is preferably a constituent unit derived from a hydroxyethyl ester of acrylic acid, and when the hydrocarbon group is a polycyclic group, the constituent unit (a3) is preferably a constituent unit represented by the following formula (a3-1), a constituent unit represented by the following formula (a3-2), or a constituent unit represented by the following formula (a3-3).

[Chemical formula 44]

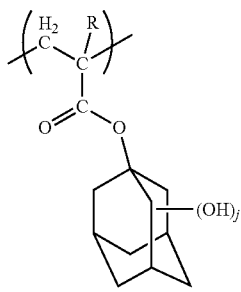
(a3-1)

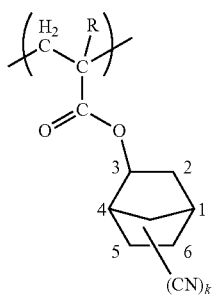
(a3-2)

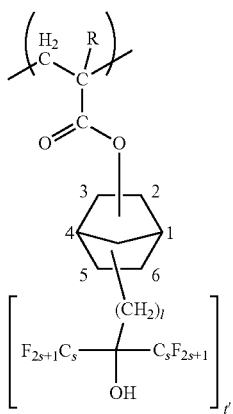
(a3-3)

In the formulae, R is the same as that described above; j represents an integer of 1 to 3; k represents an integer of 1 to 3; t' represents an integer of 1 to 3; l represents an integer of 1 to 5; and s represents an integer of 1 to 3.

In the formula (a3-1), j is preferably 1 or 2, and more preferably 1. In the case where j is 2, a constituent unit in which the hydroxyl group is bonded to the 3-position and 5-position of the adamantyl group is preferable. In the case where j is 1, a constituent unit in which the hydroxyl group is bonded to the 3-position of the adamantyl group is preferable.

j is preferably 1, and a constituent unit in which the hydroxyl group is bonded to the 3-position of the adamantyl group is especially preferable.

In the formula (a3-2), k is preferably 1. The cyano group is preferably bonded to the 5-position or 6-position of the norbornyl group.

In the formula (a3-3), t' is preferably 1. l is preferably 1. s is preferably 1. In these, it is preferable that the 2-norbornyl group or the 3-norbornyl group is bonded to the terminal of the carboxy group of acrylic acid. The fluorinated alkyl alcohol is preferably bonded to the 5- or 6-position of the norbornyl group.

The constituent unit (a3) which the component (A1) has may be either one kind or two or more kinds.

In the case where the component (A1) has the constituent unit (a3), a proportion of the constituent unit (a3) is preferably 5 mol % to 50 mol %, more preferably 5 mol % to 40 mol %, and still more preferably 5 mol % to 35 mol % relative to a total sum of all of the constituent units constituting the component (A1).

When the proportion of the constituent unit (a3) is the preferred lower limit value or more, the effects due to the fact that the constituent unit (a3) is contained are sufficiently obtained. When the proportion of the constituent unit (a3) is not more than the preferred upper limit value, a balance with other constituent units is easily taken.

Constituent Unit (a4):

The constituent unit (a4) is a constituent unit containing an acid nondissociable aliphatic cyclic group.

In view of the fact that the component (A1) has the constituent unit (a4), dry etching resistance of the formed resist pattern is enhanced. In addition, hydrophobicity of the component (A) increases. In particular, in the case of a solvent development process, it is thought that the enhancement of hydrophobicity contributes to enhancements in resolution, resist pattern shape, and the like.

The "acid nondissociable cyclic group" in the constituent unit (a4) is a cyclic group which on the occasion of generation of an acid in the resist composition upon exposure (for example, on the occasion of generation of an acid from the component (B) to be described later), even when the acid acts, remains in the constituent unit as it is without being dissociated.

The constituent unit (a4) is, for example, preferably a constituent unit derived from an acrylic ester containing an acid nondissociable aliphatic cyclic group, or the like. As the cyclic group, a large number of constituent units which have been conventionally known to be used in resin components of resist compositions such as those for ArF excimer lasers and KrF excimer lasers (preferably those for ArF excimer lasers), and the like can be used.

In particular, from the standpoint of easiness in industrial availability or the like, the constituent unit (a4) is preferably at least one kind selected from a tricyclodecyl group, an adamantyl group, a tetracyclododecyl group, an isobornyl group, and a norbornyl group. Such a polycyclic group may have a linear or branched alkyl group having 1 to 5 carbon atoms as a substituent.

Specifically, examples of the constituent unit (a4) include constituent units represented by the following general formulae (a4-r-1) to (a4-7), respectively.

[Chemical formula 45]

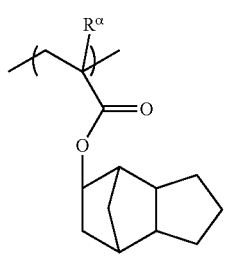
(a4-1)

(a4-2)

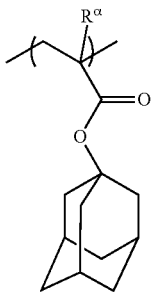

(a4-3)

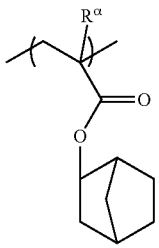

(a4-4)

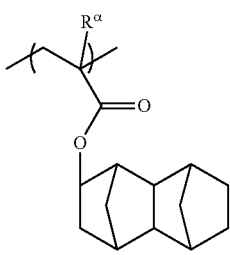

(a4-5)

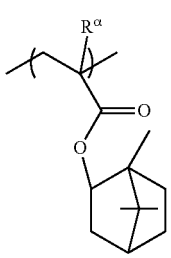

(a4-6)

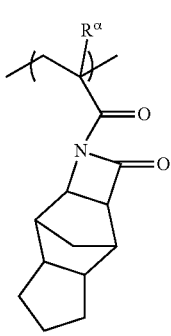

(a4-7)

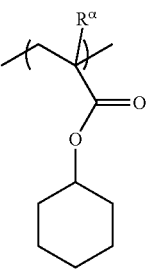

In the formula, $R^\alpha$ is the same as that described above.

The constituent unit (a4) which the component (A1) has may be either one kind or two or more kinds.

In the case where the component (A1) has the constituent unit (a4), a proportion of the constituent unit (a4) is preferably 1 mol % to 30 mol %, and more preferably 3 mol % to 20 mol % relative to a total sum of all of the constituent units constituting the component (A1).

When the proportion of the constituent unit (a4) is the preferred lower limit value or more, the effects due to the fact that the constituent unit (a4) is contained are sufficiently obtained, and when the proportion of the constituent unit (a4) is not more than the preferred upper limit value, a balance with other constituent units is easily taken.

In the resist composition (1), the component (A) contains the high-molecular weight compound (A1) having the constituent unit (a0), and specific examples of the component (A1) include a high-molecular weight compound composed of a repeating structure of the constituent unit (a0), the constituent unit (a1), and the constituent unit (a2).

A mass average molecular weight (Mw) (as converted into polystyrene by means of gel permeation chromatography (GPC)) of the component (A1) is not particularly limited, but it is preferably 1,000 to 50,000, more preferably 1,500 to 30,000, and most preferably 2,000 to 20,000.

When the Mw of the component (A1) is not more than the preferred upper limit value of the foregoing range, sufficient solubility in a resist solvent for the use as a resist is exhibited, and when it is the preferred lower limit value of the foregoing range or more, good dry etching resistance is obtained and the resist pattern has a good cross-sectional shape.

A degree of dispersion (Mw/Mn) of the component (A1) is not particularly limited, and is preferably 1.0 to 5.0, more preferably 1.0 to 4.0, and most preferably 1.0 to 3.0. It is to be noted that Mn represents a number average molecular weight.

The component (A1) may be used alone, or in combination of two or more kinds thereof.

A proportion of the component (A1) in the component (A) is preferably 25 mass % or more, more preferably 50 mass % or more, and still more preferably 75 mass % or more relative to a total mass of the component (A), and it may even be 100 mass %. When the proportion is 25 mass % or more, a resist pattern which is excellent in various lithography properties such as an increase of sensitivity and an improvement of roughness is easily formed.

In the resist composition (1), regarding the component (A), a base material component (hereinafter, referred to as "component (A3)") which does not fall under the definition of the component (A1) and exhibits changed solubility in a developing solution by the action of an acid may be used in combination.

The component (A3) is not particularly limited, and may be arbitrarily selected and used among a large number of components which have been conventionally known as a base material component for a chemically amplified resist composition (for example, base resins such as those for ArF excimer lasers and KrF excimer lasers (preferably those for ArF excimer lasers)). The component (A3) may be used alone, or in combination of two or more kinds thereof.

In the resist composition (1), the component (A) may be used alone, or in combination of two or more kinds thereof.

In the resist composition (1), the content of the component (A) may be adjusted in conformity with the thickness of the resist film to be formed, or the like.

Acid Generator Component (B): Component (B)

In the resist composition (1), the component (B) is an acid generator component which generates an acid upon exposure.

An acid dissociation constant (pKa) of the acid generated from the component (B) upon exposure is preferably not more than 0, more preferably not more than −1, still more preferably −15 to −1, and especially preferably −12 to −1.

When the pKa of the acid generated from the component (B) upon exposure is preferably not more than 0, the acid is generated upon exposure which has a relatively strong acid strength, and a pattern is sufficiently easily formed by the action of the acid and the component (A).

The term "acid dissociation constant (pKa) of the acid" mentioned herein means a value which is calculated by performing the following calculation method on the assumption that a compound having lower molecular orbital energy in the structure in an anion state of the acid has a stronger acid strength (the value of pKa is small).

Calculation Method:

(1) The structure in an anion state of an acid is optimized through a CAChe PM3 method.

(2) Highest occupied molecular orbital (HOMO) energy (eV) is obtained through molecular orbital calculation.

(3) An expression of the linear relation which is established between the substance whose pKa (measured value) in the aqueous solution is known and HOMO energy of the substance obtained through (1) and (2) is derived.

(4) With regard to the target acid, HOMO energy is obtained through (1) and (2) and is substituted in the expression of the linear relation derived in (3) to calculate a pKa (calculated value).

According to the above (1) to (4), with regard to a new acid, the pKa (calculated value) can be calculated by obtaining HOMO energy.

The reason for obtaining the HOMO energy only in an anion state of the acid is that the acid strength mainly depends on the structure in an anion state of the acid (which does not depend on a cation structure).

The expression of the linear relation in the calculation method (3) can be derived in accordance with the following procedures (i) to (iii).

(i) Actual acid dissociation constants (pKa) of the following eight kinds of compounds at 25° C. are measured.

The acid dissociation constant (pKa) can be measured in dimethyl sulfoxide (DMSO) using a pKa measuring apparatus pKa Analyzer PRO (Advanced Analytical Technologies, Inc.).

Compounds (Measured Value of pKa):

Chloroacetic acid (pKa: 2.68), acetic acid (pKa: 4.56), trichloroacetic acid (pKa: 0.66), phenol (pKa: 9.82), dichloroacetic acid (pKa: 1.3), fluoroacetic acid (pKa: 2.59), hexanoic acid (pKa 4.63), O-fluorophenol (pKa 8.49).

(ii) With regard to the compounds, HOMO energy is obtained through the calculation methods (1) and (2).

Chloroacetic acid (−4.395), acetic acid (−3.925), trichloroacetic acid (−5.073), phenol (−2.691), dichloroacetic acid (−4.763), fluoroacetic acid (−4.31), hexanoic acid (−4.076), O-fluorophenol (−2.929).

(iii) With regard to the compounds, a horizontal axis and a vertical axis are set to represent the pKa value measured in (i) and the HOMO energy (eV) obtained in (ii), respectively, to perform plotting, and a linear regression line is drawn, whereby an expression of the linear relation is derived ($R^2$=0.9868).

(HOMO energy)=0.2511×(pKa value)−5.1103

As the component (B), those which have been so far proposed as the acid generator for a chemically amplified resist can be used.

Examples of such an acid generator include a variety of acid generators such as an onium salt-based acid generator, for example, an iodonium salt and a sulfonium salt; an oxime sulfonate-based acid generator; a diazomethane-based acid generator, for example, a bisalkyl or bisaryl sulfonyl diazomethane and a poly(bissulfonyl)diazomethane; a nitrobenzylsulfonate-based acid generator; an iminosulfonate-based acid generator; and a disulfone-based acid generator. Above all, it is preferable to use an onium salt-based acid generator.

As the onium salt-based acid generator, for example, a compound represented by the following general formula (b-1) (hereinafter, also referred to as "component (b-1)"), a compound represented by a general formula (b-2) (hereinafter, also referred to as "component (b-2)"), or a compound represented by a general formula (b-3) (hereinafter, also referred to as "component (b-3)") can be used.

[Chemical formula 46]

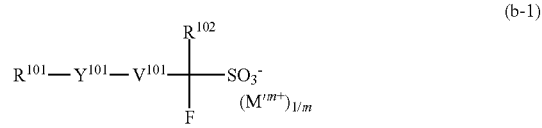

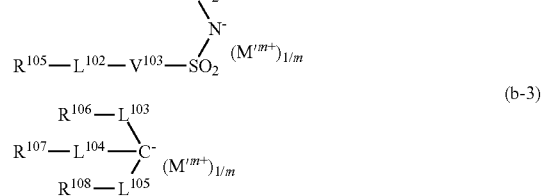

In the formulae, each of $R^{101}$ and $R^{104}$ to $R^{108}$ independently represents an optionally substituted cyclic group, an optionally substituted chain alkyl group, or an optionally substituted chain alkenyl group; $R^{104}$ and $R^{105}$ may be bonded to each other to form a ring; $R^{102}$ represents a fluorine atom or a fluorinated alkyl group having 1 to 5 carbon atoms; $Y^{101}$ represents a single bond or a divalent linking group containing an oxygen atom; each of $V^{101}$ to $V^{103}$ independently represents a single bond, an alkylene group, or a fluorinated alkylene group; each of $L^{101}$ and $L^{102}$ independently represents a single bond or an oxygen atom; each of $L^{103}$ to $L^{105}$ independently represents a single bond, —CO—, or —SO$_2$—; m represents an integer of 1 or more; and $M^{m+}$ represents an m-valent onium cation.

Anion Moiety

Anion Moiety of the Component (b-1)

In the formula (b-1), $R^{101}$ represents an optionally substituted cyclic group, an optionally substituted chain alkyl group, or an optionally substituted chain alkenyl group.

Examples of $R^{101}$ include the same groups as the optionally substituted cyclic group, the optionally substituted chain alkyl group, or the optionally substituted chain alkenyl group in $Ra^{01}$ in the formula (a0-1).

Above all, $R^{101}$ is preferably an optionally substituted cyclic group, and more preferably an optionally substituted cyclic hydrocarbon group. More specifically, a group in which one or more hydrogen atoms are eliminated from a phenyl group, a naphthyl group, or a polycycloalkane, the lactone-containing cyclic groups represented by the formulae (a2-r-1) to (a2-r-7), respectively, and the —SO$_2$—-containing cyclic groups represented by the general formulae (a5-r-1) to (a5-r-4), respectively are preferable.

In the formula (b-1), $Y^{101}$ represents a single bond or an oxygen atom-containing divalent linking group.

In the case where $Y^{101}$ is an oxygen atom-containing divalent linking group, $Y^{101}$ may contain an atom other than an oxygen atom. Examples of the atom other than an oxygen atom include a carbon atom, a hydrogen atom, a sulfur atom, and a nitrogen atom.

Examples of the oxygen atom-containing divalent linking group include a non-hydrocarbon-based oxygen atom-containing linking group such as an oxygen atom (ether bond: —O—), an ester bond (—C(=O)—O—), an oxycarbonyl group (—O—C(=O)—), an amide bond (—C(=O)—NH—), a carbonyl group (—C(=O)—), and a carbonate bond (—O—C(=O)—O—); and a combination of the non-hydrocarbon-based oxygen atom-containing linking group with an alkylene group. A sulfonyl group (—SO$_2$—) may be further connected to the combination. Examples of the combination include linking groups represented by the following formulae (y-al-1) to (y-al-7), respectively.

[Chemical formula 47]

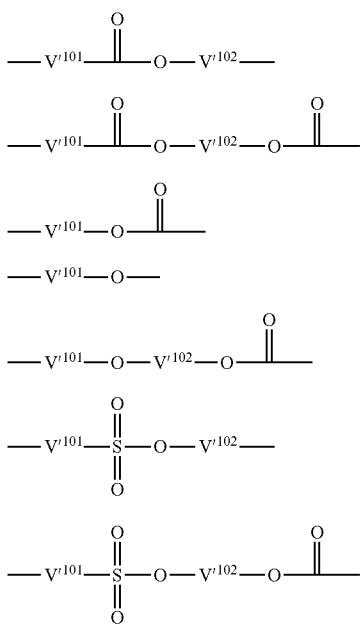

In the formulae, $V'^{101}$ represents a single bond or an alkylene group having 1 to 5 carbon atoms; and $V'^{102}$ represents a divalent saturated hydrocarbon group having 1 to 30 carbon atoms.

The divalent saturated hydrocarbon group in $V'^{102}$ is preferably an alkylene group having 1 to 30 carbon atoms.

The alkylene group in $V'^{101}$ and $V'^{102}$ may be a linear alkylene group, or may be a branched alkylene group, and it is preferably a linear alkylene group.

Specifically, examples of the alkylene group in $V'^{101}$ and $V'^{102}$ include a methylene group [—CH$_2$—]; an alkylmethylene group such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; an ethylene group [—CH$_2$CH$_2$—]; an alkylethylene group such as —CH(CH$_3$)CH$_2$—, —CH(CH$_3$)CH(CH$_3$)—, —C(CH$_3$)$_2$CH$_2$—, and —CH(CH$_2$CH$_3$)CH$_2$—; a trimethylene group (n-propylene group) [—CH$_2$CH$_2$CH$_2$—]; an alkyltrimethylene group such as —CH(CH$_3$)CH$_2$CH$_2$— and —CH$_2$CH(CH$_3$)CH$_2$—; a tetramethylene group [—CH$_2$CH$_2$CH$_2$CH$_2$—]; an alkyltetramethylene group such as —CH(CH$_3$)CH$_2$CH$_2$CH$_2$— and —CH$_2$CH(CH$_3$)CH$_2$CH$_2$—; and a pentamethylene group [—CH$_2$CH$_2$CH$_2$CH$_2$CH$_2$—].

In addition, some of the methylene groups in the above-described alkylene group in $V'^{101}$ or $V'^{102}$ may be substituted with a divalent aliphatic cyclic group having 5 to 10 carbon atoms. The aliphatic cyclic group is preferably a divalent group in which one hydrogen atom is further eliminated from the monocyclic or polycyclic aliphatic hydrocarbon group in $Ra^{t3}$ in the formula (a1-r-1), and more preferably a cyclohexylene group, a 1,5-adamantylene group, or a 2,6-adamantylene group.

$Y^{101}$ is preferably a divalent linking group containing an ester bond or an ether bond, and the linking groups represented by the formulae (y-al-1) to (y-al-5), respectively are preferable.

In the formula (b-1), $V^{101}$ represents a single bond, an alkylene group, or a fluorinated alkylene group. The number of carbon atoms of each of the alkylene group and the fluorinated alkylene group in $V^{101}$ is preferably 1 to 4. Examples of the fluorinated alkylene group in $V^{101}$ include a group in which some or all the hydrogen atoms of the alkylene group in $V^{101}$ are substituted with a fluorine atom. Above all, $V^{101}$ is preferably a single bond or a fluorinated alkylene group having 1 to 4 carbon atoms.

In the formula (b-1), $R^{102}$ represents a fluorine atom or a fluorinated alkyl group having 1 to 5 carbon atoms. $R^{102}$ is preferably a fluorine atom or a perfluoroalkyl group having 1 to 5 carbon atoms, and more preferably a fluorine atom.

An acid dissociation constant (pKa) of the acid which is generated from the component (b-1) upon exposure is approximately −12 to −1, and preferably approximately −7 to −1.

As for specific examples of the anion moiety of the component (b-1), in the case where $Y^{101}$ is a single bond, examples thereof include a fluorinated alkyl sulfonate anion such as a trifluoromethane sulfonate anion and a perfluorobutane sulfonate anion; and in the case where $Y^{101}$ is an oxygen atom-containing divalent linking group, examples thereof include any of anions represented by the following formulae (an-1) to (an-3).

[Chemical formula 48]

(an-1)

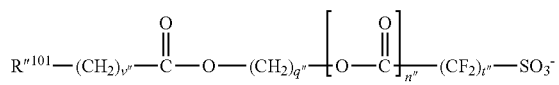

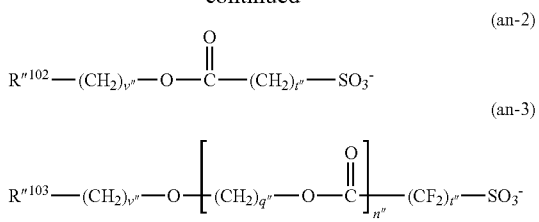

In the formulae, $R''^{101}$ represents an optionally substituted aliphatic cyclic group, a group represented by each of the formulae (r-hr-1) to (r-hr-6), or an optionally substituted chain alkyl group; $R''^{102}$ represents an optionally substituted aliphatic cyclic group, a lactone-containing cyclic group represented by each of the formulae (a2-r-1) to (a2-r-7), or an $-SO_2-$-containing cyclic group represented by each of the formulae (a5-r-1) to (a5-r-4); $R''^{103}$ represents an optionally substituted aromatic cyclic group, an optionally substituted aliphatic cyclic group, or an optionally substituted chain alkenyl group; each v'' independently represents an integer of 0 to 3; each q'' independently represents an integer of 1 to 20; t'' represents an integer of 1 to 3; and n'' represents 0 or 1.

The optionally substituted aliphatic cyclic group represented by each of $R''^{101}$, $R''^{102}$, and $R''^{103}$ is preferably the group exemplified above for the cyclic aliphatic hydrocarbon group in $Ra^{01}$. Examples of the substituent include the same substituents as those with which the cyclic aliphatic hydrocarbon group in $Ra^{01}$ may be substituted.

The optionally substituted aromatic cyclic group in $R''^{103}$ is preferably the group exemplified above for the aromatic hydrocarbon group in the cyclic hydrocarbon group in $Ra^{01}$. Examples of the substituent include the same substituents as those with which the aromatic hydrocarbon group in $Ra^{01}$ may be substituted.

The optionally substituted chain alkyl group in $R''^{101}$ is preferably the group exemplified above for the chain alkyl group in $Ra^{01}$. The optionally substituted chain alkenyl group in $R''^{103}$ is preferably the group exemplified above for the chain alkenyl group in $Ra^{01}$.

Anion Moiety of Component (b-2)

In the formula (b-2), each of $R^{104}$ and $R^{105}$ independently represents an optionally substituted cyclic group, an optionally substituted chain alkyl group, or an optionally substituted chain alkenyl group, and examples thereof include the same groups as those in $R^{101}$ in the formula (b-1). However, $R^{104}$ and $R^{105}$ may be bonded to each other to form a ring.

Each of $R^{104}$ and $R^{105}$ is preferably an optionally substituted chain alkyl group, and more preferably a linear or branched alkyl group or a linear or branched fluorinated alkyl group.

The number of carbon atoms of the chain alkyl group is preferably 1 to 10, more preferably 1 to 7, and still more preferably 1 to 3. The number of carbon atoms of the chain alkyl group represented by each of $R^{104}$ and $R^{105}$ is preferably smaller within the above-described range of the number of carbon atoms for reasons such as good solubility in a resist solvent. In addition, in the chain alkyl group represented by each of $R^{104}$ and $R^{105}$, the number of the hydrogen atoms substituted with a fluorine atom is preferably larger because the strength of the acid increases, and the transparency to a high energy light or electron beams of not more than 200 nm is enhanced. A proportion of the fluorine atom in the chain alkyl group, namely a fluorination rate, is preferably 70% to 100%, and more preferably 90% to 100%. A perfluoroalkyl group in which all of the hydrogen atoms are substituted with a fluorine atom is the most preferable.

In the formula (b-2), each of $V^{102}$ and $V^{103}$ independently represents a single bond, an alkylene group, or a fluorinated alkylene group, and examples thereof include the same groups as those in $V^{101}$ in the formula (b-1).

In the formula (b-2), each of $L^{101}$ and $L^{102}$ independently represents a single bond or an oxygen atom.

An acid dissociation constant (pKa) of the acid which is generated from the component (b-2) upon exposure is approximately −12 to −1, and preferably approximately −12 to −4.

Anion Moiety of Component (b-3)

In the formula (b-3), each of $R^{106}$ to $R^{108}$ independently represents an optionally substituted cyclic group, an optionally substituted chain alkyl group, or an optionally substituted chain alkenyl group, and examples thereof include the same groups as those in $R^{101}$ in the formula (b-1).

Each of $L^{103}$ to $L^{105}$ independently represents a single bond, $-CO-$, or $-SO_2-$.

An acid dissociation constant (pKa) of the acid which is generated from the component (b-3) upon exposure is approximately −15 to −1, and preferably approximately −14 to −4.

Cation Moiety

In the formulae (b-1), (b-2), and (b-3), $M'^{m+}$ represents an m-valent onium cation, and preferred examples thereof include a sulfonium cation and an iodonium cation.

Specifically, preferred examples of $[(M'^{m+})_{1/m}]$ include the same organic cations as those represented by the general formulae (ca-1) to (ca-4), respectively. Specific examples thereof include cations represented by the formulae (a0-r-1) to (ca-1-67), respectively.

Among the foregoing, the cation moiety $[(M'^{m+})_{1/m}]$ is preferably the organic cation represented by the general formula (ca-1), and more preferably the cation represented by each of the formulae (ca-1-1) to (ca-1-67).

As the component (B), the above-described acid generator may be used alone, or in combination of two or more kinds thereof.

Among the foregoing, as the component (B), an acid generator composed of a compound represented by the following general formula (b-1-1) is especially preferably used.

[Chemical formula 49]

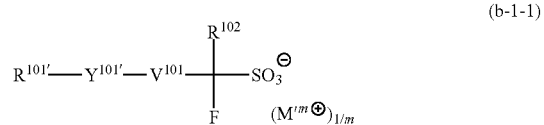

(b-1-1)

In the formula, $R^{101'}$ represents an optionally substituted cyclic group; $R^{102}$ represents a fluorine atom or a fluorinated alkyl group having 1 to 5 carbon atoms; $Y^{101'}$ represents a divalent linking group containing an oxygen atom; $V^{101}$ represents a single bond, an alkylene group, or a fluorinated alkylene group; m represents an integer of 1 or more; and $M'^{m+}$ represents an m-valent onium cation.

In the formula (b-1-1), examples of $R^{101'}$ include the same one as the "optionally substituted cyclic group" in $R^{101}$, and a cyclic aliphatic hydrocarbon group or a heterocyclic group is preferable. Specifically, examples of the heterocyclic group include the lactone-containing cyclic groups represented by the general formulae (a2-r-1) to (a2-r-7), respectively, the $-SO_2-$-containing cyclic groups represented by the general formulae (a5-r-1) to (a5-r-4), respectively, and the heterocyclic groups represented by the chemical formulae (r-hr-1) to (r-hr-16), respectively.

Examples of $Y^{101'}$ in the formula (b-1-1) include the same one as the "oxygen atom-containing divalent linking group" in $Y^{101}$ in the formula (b-1).

In the formula (b-1-1), $R^{102}$, $V^{101}$, m, and $M^{m+}$ are the same as $R^{102}$, $V^{101}$, m, and $M^{m+}$ in the formula (b-1).

In the resist composition (1), the content of the component (B) is preferably 0.5 part by mass to 60 parts by mass, more preferably 1 part by mass to 50 parts by mass, and still more preferably 1 part by mass to 40 parts by mass based on 100 parts by mass of the component (A).

The content of the component (B) is preferably within the foregoing preferred range, because the pattern formation is sufficiently conducted, and on the occasion of dissolving the respective components of the resist composition (1) in an organic solvent, a uniform solution is obtained and the storage stability is improved.

Compound (D1): Component (D1)

In the resist composition (1), the component (D1) is a compound including a partial structure represented by the general formula (a0-r-1).

The component (D1) is not particularly limited so long as it is a compound including the partial structure, and preferred examples thereof include a compound represented by the following general formula (d1-1).

[Chemical formula 50]

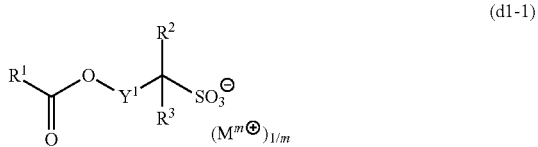

(d1-1)

In the formula, $R^1$ represents an optionally substituted hydrocarbon group having 4 to 20 carbon atoms; $Y^1$ represents a divalent linking group; each of $R^2$ and $R^3$ independently represents a group having 0 to 20 carbon atoms, which is not a fluorine atom, and either $R^2$ or $R^3$ may form a ring with $Y^1$; m represents an integer of 1 or more; and $M^{m+}$ represents an m-valent organic cation.

Anion Moiety of Component (D1):

In the formula (d1-1), $R^1$ represents an optionally substituted hydrocarbon group having 4 to 20 carbon atoms. The hydrocarbon group represented by $R^1$ may be either an aliphatic hydrocarbon group or an aromatic hydrocarbon group. The aliphatic hydrocarbon group means a hydrocarbon group having no aromaticity. The aliphatic hydrocarbon group may be either saturated or unsaturated, and in general, it is preferably saturated.

Examples of the hydrocarbon group represented by $R^1$ include a linear or branched alkyl group and a cyclic hydrocarbon group.

In the hydrocarbon group represented by $R^1$, the linear or branched alkyl group preferably has 4 to 20 carbon atoms. Specifically, examples thereof include an n-butyl group, an isobutyl group, a tert-butyl group, a pentyl group, an isopentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, a 1,1-dimethylethyl group, a 1,1-diethylpropyl group, a 2,2-dimethylpropyl group, and a 2,2-dimethylbutyl group.

The cyclic hydrocarbon group in the hydrocarbon group represented by $R^1$ may be either an aliphatic group or an aromatic group. In addition, it may be either a polycyclic group or a monocyclic group.

The monocyclic alicyclic hydrocarbon group is preferably a group in which one hydrogen atom is eliminated from a monocycloalkane. The monocycloalkane is preferably one having 4 to 8 carbon atoms. Specifically, examples thereof include cyclopentane, cyclohexane, and cyclooctane. The polycyclic alicyclic hydrocarbon group is preferably a group in which one hydrogen atom is eliminated from a polycycloalkane. The polycycloalkane preferably has 7 to 12 carbon atoms. Specifically, examples thereof include adamantane, norbornane, isobornane, tricyclodecane, and tetracyclododecane.

In addition, the alicyclic hydrocarbon group in $R^1$ may contain a hetero atom in a ring structure thereof. Examples of the substituent containing the hetero atom include —O—, —C(=O)—O—, —S—, —S(=O)$_2$—, and —S(=O)$_2$—O—.

Specific examples of such an alicyclic group containing a hetero atom in a ring structure thereof include groups represented by the general formulae (a2-r-1) to (a2-r-7), (a5-r-1) to (a5-r-4), and (ax3-r-1) to (ax3-r-3), respectively, and specific examples thereof, and preferred examples thereof include groups represented by the formulae (r-lc-1-1), (r-lc-1-2), (r-lc-2-1), (r-lc-2-7), (r-lc-6-1), (r-lc-7-1), (r-sl-1-1), and (r-sl-1-18), respectively.

When $R^1$ is an aromatic hydrocarbon group, specific examples of the aromatic ring included therein include an aromatic hydrocarbon ring such as benzene, biphenyl, fluorene, naphthalene, anthracene, and phenanthrene; and an aromatic heterocyclic ring in which some of the carbon atoms constituting the above-described aromatic hydrocarbon ring are substituted with a hetero atom. Examples of the hetero atom in the aromatic heterocyclic ring include an oxygen atom, a sulfur atom, and a nitrogen atom.

Specifically, examples of the aromatic hydrocarbon group include a group in which one hydrogen atom is eliminated from the aromatic hydrocarbon ring (aryl group); and a group in which one hydrogen atom of the aryl group is substituted with an alkylene group (for example, an arylalkyl group such as a benzyl group, a phenethyl group, a 1-naphthylmethyl group, a 2-naphthylmethyl group, a 1-naphthylethyl group, and a 2-naphthylethyl group). The number of carbon atoms of the alkylene group (the alkyl chain in the arylalkyl group) is preferably 1 to 4, more preferably 1 to 2, and especially preferably 1.

Examples of the substituent which $R^1$ may have include an amino group, a —C(=O)—$R'''^1$ group, a —O—C(=O)—$R'''^1$ group ($R'''^1$ represents an alkyl group having 1 to 5 carbon atoms), an alkyl group, an alkoxy group, a halogen atom, a halogenated alkyl group, a hydroxyl group, and an oxo group (=O). The substituent is preferably a polar group such as an amino group, a —O—C(=O)—$R'''^1$ group, a hydroxyl group, and an oxo group, since lithography properties are enhanced.

The alkyl group as the substituent is preferably an alkyl group having 1 to 5 carbon atoms, and most preferably a methyl group, an ethyl group, a propyl group, an n-butyl group, or a tert-butyl group.

The alkoxy group as the substituent is preferably an alkoxy group having 1 to 5 carbon atoms, more preferably a methoxy group, an ethoxy group, an n-propoxy group, an isopropoxy group, an n-butoxy group, or a tert-butoxy group, and most preferably a methoxy group or an ethoxy group.

Examples of the halogen atom as the substituent include a fluorine atom, a chlorine atom, a bromine atom, and an iodine atom, with a fluorine atom being preferable.

Examples of the halogenated alkyl group as the substituent include a group in which some or all the hydrogen atoms of the alkyl group are substituted with the halogen atom.

$R^1$ is preferably an optionally substituted aliphatic hydrocarbon group having 4 to 20 carbon atoms since lithography properties such as sensitivity, EL margin, LWR and the like are enhanced. Above all, each of groups represented by the formulae (r-lc-1-1), (r-lc-1-2), (r-lc-2-1), (r-lc-2-7), (r-lc-6-1), (r-lc-7-1), (r-sl-1-1), and (r-sl-1-18), respectively, an aliphatic hydrocarbon group having the polar group as a substituent, or an optionally substituted monocyclic or polycyclic alicyclic hydrocarbon group is more preferable in terms of sensitivity and lithography properties.

In the formula (d1-1), $Y^1$, $R^2$, and $R^3$ are the same as $Y^1$, $R^2$, and $R^3$ in the formula (a0-r-1).

In the formula (d1-1), $Y^1$ is preferably an optionally substituted linear or branched aliphatic hydrocarbon group, and more preferably a linear or branched alkylene group having 1 to 5 carbon atoms.

In the formula (d1-1), each of $R^2$ and $R^3$ is preferably a hydrogen atom. Both $R^2$ and $R^3$ are especially preferably a hydrogen atom.

Hereinafter, specific preferred examples of the anion moiety of the component (D1) are given below. In addition, examples in which the structure of a part other than $R^1$ in the following specific examples corresponds to the structures of the specific examples of the anion moiety of the partial structure represented by the above-described general formula (a0-r-1) are also shown.

[Chemical formula 51]

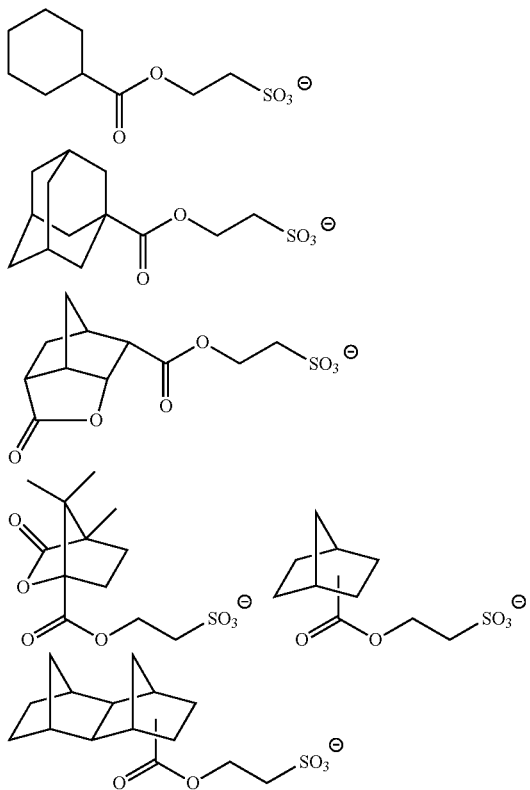

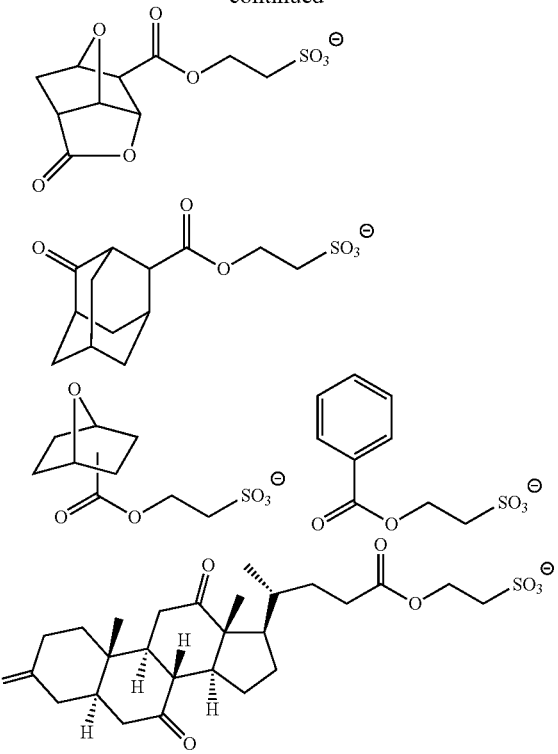

Cation Moiety of Component (D1):

In the formula (d1-1), $M^{m+}$ represents an m-valent organic cation and is the same as $M^{m+}$ in the formula (a0-r-1). Above all, a cation moiety $[(M^{m+})_{1/m}]$ is preferably an organic cation represented by the general formula (ca-1), and more preferably each of cations represented by the formulae (ca-1-1) to (ca-1-67), respectively.

The component (D1) may be used alone, or in combination of two or more kinds thereof.

The content of the component (D1) is preferably 0.5 part by mass to 20 parts by mass, more preferably 1 part by mass to 15 parts by mass, and still more preferably 2 parts by mass to 12 parts by mass based on 100 parts by mass of the component (A).

When the content of the component (D1) is the preferred lower limit value or more, good lithography properties such, in particular, as an improvement of roughness and a good resist pattern shape are obtained. On the other hand, when it is not more than the preferred upper limit value, the sensitivity can be maintained at a satisfactory level, and the throughput is also improved.

In the invention, the term "molar ratio represented by (D1)/(B)" refers to a mixing ratio of the component (D1) to the component (B) contained in the resist composition, that is, a proportion (molar ratio) of the content of the component (D1) to the content of the component (B).

In the resist composition (1), the mixing ratio of the compound (D1) to the acid generator component (B) is preferably 0.4 or more, more preferably 0.4 to 1.5, still more preferably 0.5 to 1.5, and especially preferably 0.6 to 1.2 in terms of a molar ratio represented by (D1)/(B) (hereinafter, also referred to as "ratio (D1)/(B)").

When the ratio (D1)/(B) is the preferred lower limit value or more, it is excellent in reducing roughness of the resist pattern. In addition, the exposure margin (EL margin) is more easily enhanced. When the ratio (D1)/(B) is not more than the preferred upper limit value, the sensitivity further increases.

Other Components

The resist composition (1) may further contain other components in addition to the component (A), the component (B), and the component (D1).

Component (D2)

The resist composition (1) may contain, as an optional component, a photodegradable base (hereinafter, referred to as "component (D2)") which is decomposed upon exposure to lose acid diffusion controlling properties.

When the resist composition contains the component (D2), a contrast between exposed areas and unexposed areas can be enhanced on the occasion of forming a resist pattern.

Though the component (D2) is not particularly limited so long as it is decomposed upon exposure to lose acid diffusion controlling properties, the component (D2) is preferably at least one kind of compound selected from the group consisting of a compound represented by the following general formula (d2-1) (hereinafter, referred to as "component (d2-1)"), a compound represented by the following general formula (d2-2) (hereinafter, referred to as "component (d2-2)"), and a compound represented by the following general formula (d2-3) (hereinafter, referred to as "component (d2-3)").

Each of the components (d2-1) to (d2-3) does not act as a quencher in exposed areas because it is decomposed to lose acid diffusion controlling properties (basicity), but acts as a quencher in unexposed areas.

[Chemical formula 52]

In the formulae, each of $Rd^1$ to $Rd^4$ represents an optionally substituted cyclic group, an optionally substituted chain alkyl group, or an optionally substituted chain alkenyl group, provided that a fluorine atom is not bonded to the carbon atom adjacent to the S atom in $R^{d2}$ in the formula (d2-2); $Yd^1$ represents a single bond or a divalent linking group; m represents an integer of 1 or more, and each $M^{m+}$ independently represents an m-valent organic cation.

Component (d2-1)

Anion Moiety of Component (d2-1):

In the formula (d2-1), $Rd^1$ represents an optionally substituted cyclic group, an optionally substituted chain alkyl group, or an optionally substituted chain alkenyl group, and examples thereof include the same groups as those in $R^{101}$ in the formula (b-1).

Above all, $Rd^1$ is preferably an optionally substituted aromatic hydrocarbon group, an optionally substituted aliphatic cyclic group, or an optionally substituted chain alkyl group. The substituent which each of these groups may have is preferably a hydroxyl group, a fluorine atom, or a fluorinated alkyl group.

The aromatic hydrocarbon group is more preferably a phenyl group or a naphthyl group.

The aliphatic cyclic group is more preferably a group in which one or more hydrogen atoms are eliminated from a polycycloalkane such as adamantane, norbornane, isobornane, tricyclodecane, and tetracyclododecane.

The chain alkyl group is preferably a chain alkyl group having 1 to 10 carbon atoms. Specifically, examples thereof include a linear alkyl group such as a methyl group, an ethyl group, a propyl group, a butyl group, a pentyl group, a hexyl group, a heptyl group, an octyl group, a nonyl group, and a decyl group; and a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, and a 4-methylpentyl group.

In the case where the chain alkyl group is a fluorinated alkyl group having, as a substituent, a fluorine atom, the number of carbon atoms of the fluorinated alkyl group is preferably 1 to 11, more preferably 1 to 8, and still more preferably 1 to 4. The fluorinated alkyl group may also contain an atom other than a fluorine atom. Examples of the atom other than a fluorine atom include an oxygen atom, a carbon atom, a hydrogen atom, a sulfur atom, and a nitrogen atom.

$Rd^1$ is preferably a fluorinated alkyl group in which some or all hydrogen atoms constituting a linear alkyl group are substituted with a fluorine atom, and more preferably a fluorinated alkyl group (linear perfluoroalkyl group) in which all of hydrogen atoms constituting a linear alkyl group are substituted with a fluorine atom.

Preferred specific examples of the anion moiety of the component (d2-1) are given below.

[Chemical formula 53]

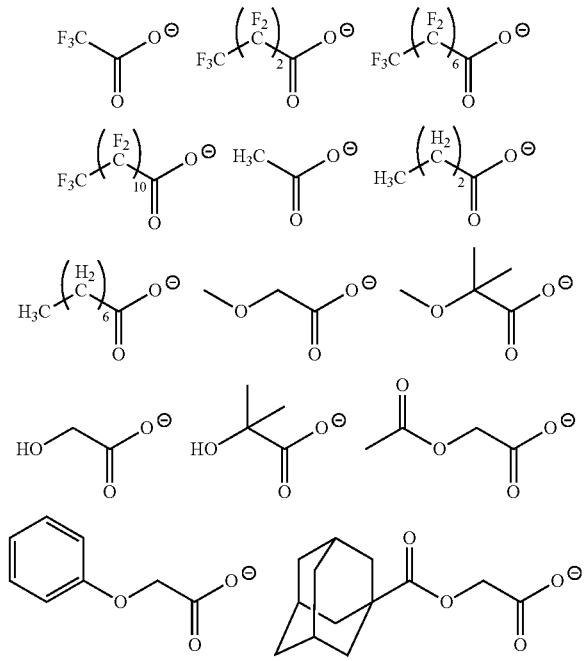

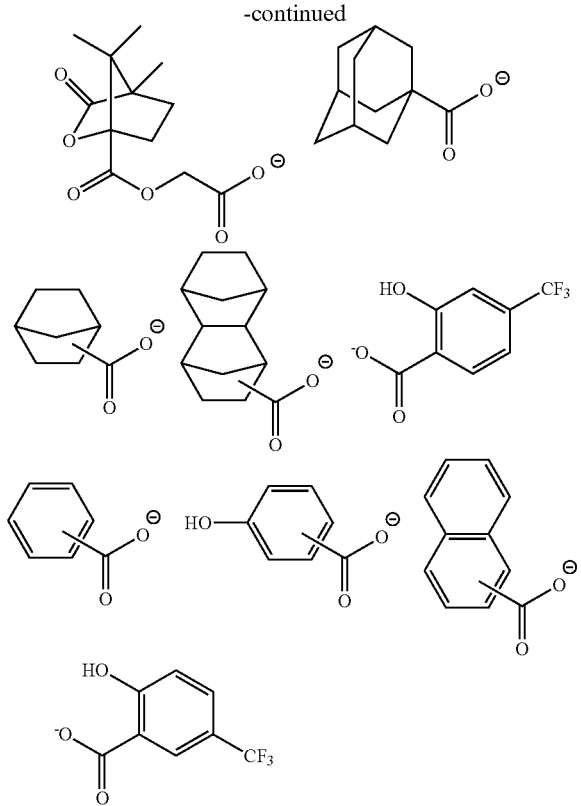

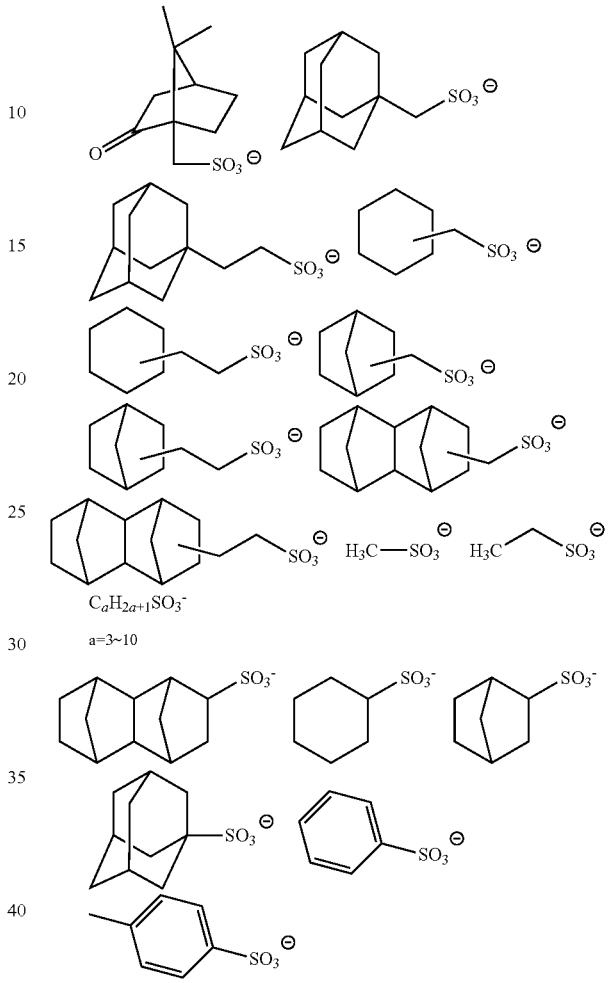

Preferred specific examples of the anion moiety of the component (d2-2) are given below.

[Chemical formula 54]

Cation Moiety of Component (d2-1):

In the formula (d2-1), $M^{m+}$ represents an m-valent organic cation.

Preferred examples of the organic cation represented by $M^{m+}$ include the same cations as those represented by the general formulae (ca-1) to (ca-4), respectively. Specific examples thereof include cations represented by the formulae (ca-1-1) to (ca-1-67), respectively.

The component (d2-1) may be used alone, or in combination of two or more kinds thereof.

Component (d2-2)

Anion Moiety of Component (d2-2):

In the formula (d2-2), $Rd^2$ represents an optionally substituted cyclic group, an optionally substituted chain alkyl group, or an optionally substituted chain alkenyl group, and examples thereof include the same groups as those in $R^{101}$ in the formula (b-1).

However, a fluorine atom is not bonded to (there is no fluorine-substitution at) the carbon atom adjacent to the S atom in $Rd^2$. According to this, the anion of the component (d2-2) becomes an appropriately weak acid anion, whereby the quenching ability is enhanced.

$Rd^2$ is preferably an optionally substituted aliphatic cyclic group, and more preferably a (optionally substituted) group in which one or more hydrogen atoms are eliminated from adamantane, norbornane, isobornane, tricyclodecane, tetracyclododecane, or the like; or a group in which one or more hydrogen atoms are eliminated from camphor or the like.

The hydrocarbon group represented by $Rd^2$ may have a substituent. Examples of the substituent include the same groups as those exemplified above for the substituent which the hydrocarbon group (aromatic hydrocarbon group or aliphatic hydrocarbon group) in $Rd^1$ in the formula (d2-1) may have.

Cation Moiety of Component (d2-2)

In the formula (d2-2), $M^{m+}$ represents an m-valent organic cation and is the same as $M^{m+}$ in the formula (d2-1).

The component (d2-2) may be used alone, or in combination of two or more kinds thereof.

Component (d2-3)

Anion Moiety of Component (d2-3):

In the formula (d2-3), $Rd^3$ represents an optionally substituted cyclic group, an optionally substituted chain alkyl group, or an optionally substituted chain alkenyl group, and examples thereof include the same groups as those in $R^{101}$ in the formula (b-1). $Rd^3$ is preferably a cyclic group, a chain alkyl group, or a chain alkenyl group, each of which contains a fluorine atom. Above all, $Rd^3$ is preferably a fluorinated alkyl group, and more preferably the same fluorinated alkyl group as that represented by $Rd^1$ as described above.

In the formula (d2-3), $Rd^4$ represents an optionally substituted cyclic group, an optionally substituted chain alkyl group, or an optionally substituted chain alkenyl group, and examples thereof include the same groups as those in $R^{101}$ in the formula (b-1).

Above all, $Rd^4$ is preferably an alkyl group, an alkoxy group, an alkenyl group, or a cyclic group, each of which may have a substituent.

The alkyl group in $Rd^4$ is preferably a linear or branched alkyl group having 1 to 5 carbon atoms. Specifically, examples thereof include a methyl group, an ethyl group, a propyl group, an isopropyl group, an n-butyl group, an isobutyl group, a tert-butyl group, a pentyl group, an isopentyl group, and a neopentyl group. Some of the hydrogen atoms of the alkyl group represented by $Rd^4$ may be substituted with a hydroxyl group, a cyano group, or the like.

The alkoxy group in $Rd^4$ is preferably an alkoxy group having 1 to 5 carbon atoms. Specifically, examples of the alkoxy group having 1 to 5 carbon atoms include a methoxy group, an ethoxy group, an n-propoxy group, an isopropoxy group, an n-butoxy group, and a tert-butoxy group. Above all, a methoxy group or an ethoxy group is preferable.

Examples of the alkenyl group in $Rd^4$ include the same groups as those in $R^{101}$ in the formula (b-1). Above all, a vinyl group, a propenyl group (allyl group), a 1-methylpropenyl group, and a 2-methylpropenyl group are preferable. Each of these groups may further have, as a substituent, an alkyl group having 1 to 5 carbon atoms or a halogenated alkyl group having 1 to 5 carbon atoms.

Examples of the cyclic group in $Rd^4$ include the same groups as those in $R^{101}$ in the formula (b-1). Above all, an alicyclic group in which one or more hydrogen atoms are eliminated from a cycloalkane such as cyclopentane, cyclohexane, adamantane, norbornane, isobornane, tricyclodecane, and tetracyclododecane, or an aromatic group such as a phenyl group and a naphthyl group is preferable. In the case where $Rd^4$ is an alicyclic group, in view of the fact that the resist composition is well dissolved in an organic solvent, the lithography properties are enhanced. In addition, in the case where $Rd^4$ is an aromatic group, in the lithography using EUV or the like as an exposure light source, the resist composition exhibits excellent light absorption efficiency, and the sensitivity and lithography properties are enhanced.

In the formula (d2-3), $Yd^1$ represents a single bond or a divalent linking group.

Though the divalent linking group in $Yd^1$ is not particularly limited, examples thereof include an optionally substituted divalent hydrocarbon group (aliphatic hydrocarbon group or aromatic hydrocarbon group) and a divalent linking group containing a hetero atom. Examples of each of these groups include the same groups as the optionally substituted divalent hydrocarbon group and the divalent linking group containing a hetero atom exemplified above in the description of the divalent linking group represented by $Ya^{21}$ in the foregoing formula (a2-1).

$Yd^1$ is preferably a carbonyl group, an ester bond, an amide bond, an alkylene group, or a combination thereof. The alkylene group is more preferably a linear or branched alkylene group, and still more preferably a methylene group or an ethylene group.

Preferred specific examples of the anion moiety of the component (d2-3) are given below.

[Chemical formula 55]

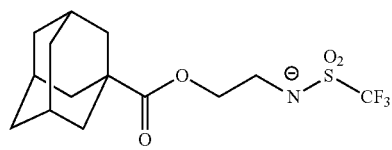

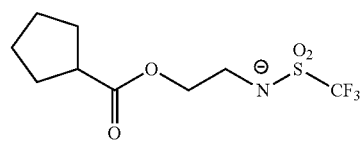

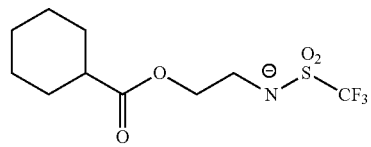

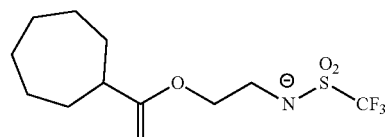

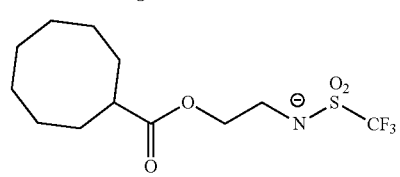

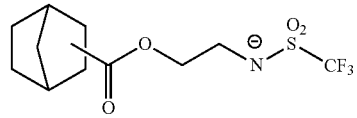

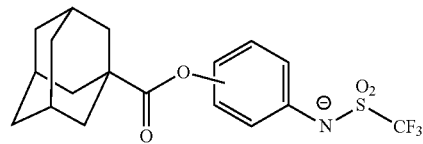

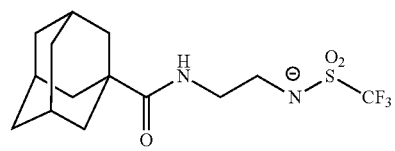

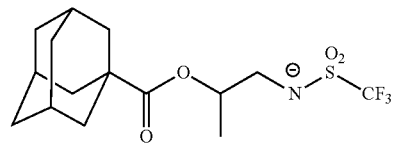

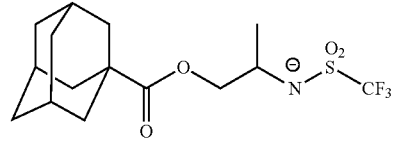

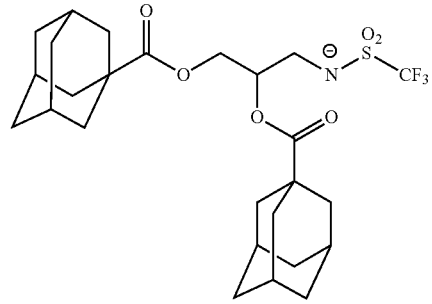

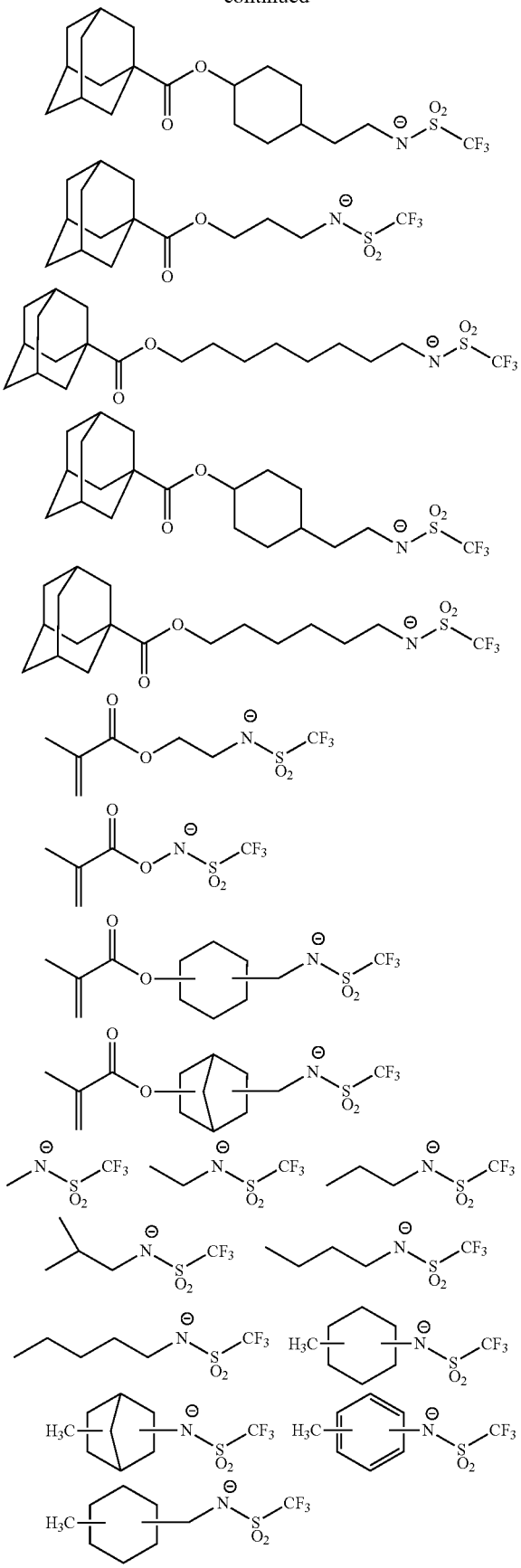

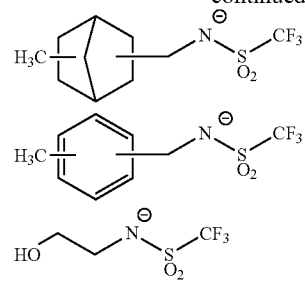

Cation Moiety of Component (d2-3):

In the formula (d2-3), $M^{m+}$ represents an m-valent organic cation and is the same as $M^{m+}$ in the formula (d2-1).

The component (d2-3) may be used alone, or in combination of two or more kinds thereof.

As the component (D2), only one kind of the components (d2-1) to (d2-3) may be used, or a combination of two or more kinds thereof may also be used.

In addition, as the component (D2), a component which generates, upon exposure, an acid having a relatively higher acid dissociation constant (pKa) than pKa of the acid which is generated upon exposure from a component used as the component (B) is preferably used. The pKa of the acid which is generated from the component (D2) upon exposure is preferably more than 0, more preferably 1 or more, and still more preferably 1 to 7.

When the component (D2) is used, the content of the component (D2) is preferably 0.5 part by mass to 10 parts by mass, more preferably 0.5 part by mass to 8 parts by mass, and still more preferably 1 part by mass to 8 parts by mass based on 100 parts by mass of the component (A).

When the content of the component (D2) is the preferred lower limit value or more, particularly good lithography properties and a good resist pattern shape are easily obtained. On the other hand, when it is not more than the preferred upper limit value, the sensitivity can be maintained at a satisfactory level, and the throughput is also improved.

Method of Manufacturing Component (D2)

A method of manufacturing the above-described component (d2-1) and component (d2-2) is not particularly limited, and each of the component (d2-1) and the component (d2-2) can be manufactured by a known method.

In addition, a method of manufacturing the component (d2-3) is not particularly limited, and the component (d2-3) is manufactured in the same manner as in the method disclosed in, for example, US 20120149916 A1.

Component (D3)

The resist composition (1) may contain a nitrogen-containing organic compound component (hereinafter, referred to as "component (D3)") as an optional component.

The component (D3) is not particularly limited so long as it acts as an acid diffusion control agent and does not fall under the definition of the component (D1) or (D2), and any known compound may be arbitrarily used. Above all, an aliphatic amine, in particular, a secondary aliphatic amine or a tertiary aliphatic amine, is preferable.

The aliphatic amine refers to an amine having one or more aliphatic groups, and the number of carbon atoms of the aliphatic group is preferably 1 to 12.

Examples of the aliphatic amine include an amine in which at least one of hydrogen atoms of ammonia $NH_3$ is substituted with an alkyl group or a hydroxyalkyl group each having not more than 12 carbon atoms (i.e., an alkylamine or an alkyl alcoholamine) and a cyclic amine.

Specific examples of the alkylamine and the alkyl alcoholamine include a monoalkylamine such as n-hexylamine, n-heptylamine, n-octylamine, n-nonylamine, and n-decylamine; a dialkylamine such as diethylamine, di-n-propylamine, di-n-heptylamine, di-n-octylamine, and dicyclohexylamine; a trialkylamine such as trimethylamine, triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, and tri-n-dodecylamine; and an alkyl alcoholamine such as diethanolamine, triethanolamine, diisopropanolamine, triisopropanolamine, di-n-octanolamine, and tri-n-octanolamine. Of these, a trialkylamine having 5 to 10 carbon atoms is more preferable, and tri-n-pentylamine or tri-n-octylamine is especially preferable.

Examples of the cyclic amine include a heterocyclic compound containing a nitrogen atom as a hetero atom. The heterocyclic compound may be a monocyclic compound (aliphatic monocyclic amine), or may be a polycyclic compound (aliphatic polycyclic amine).

Specifically, examples of the aliphatic monocyclic amine include piperidine and piperazine.

The aliphatic polycyclic amine is preferably an aliphatic polycyclic amine having 6 to 10 carbon atoms. Specifically, examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, and triethanolamine triacetate, with triethanolamine triacetate being preferable.

In addition, an aromatic amine may also be used as the component (D3).

Examples of the aromatic amine include 4-dimethylaminopyridine, pyrrole, indole, pyrazole, imidazole, and derivatives thereof, as well as tribenzylamine, 2,6-diisopropylaniline, and N-tert-butoxycarbonylpyrrolidine.

The component (D3) may be used alone, or in combination of two or more kinds thereof.

In the case where the component (D3) is used, the component (D3) is generally used in an amount in the range of 0.01 part by mass to 5 parts by mass based on 100 parts by mass of the component (A). When the amount of the component (D3) falls within the foregoing range, the resist pattern shape, the post-exposure temporal stability, and the like are enhanced.

Component (E)

For the purposes of preventing deterioration in sensitivity and enhancing the resist pattern shape, the post-exposure temporal stability, and the like, the resist composition (1) can contain, as an optional component, at least one kind of compound (hereafter, referred to as "component (E)") selected from the group consisting of an organic carboxylic acid and a phosphorus oxo acid and a derivative thereof.

Preferred examples of the organic carboxylic acid include acetic acid, malonic acid, citric acid, malic acid, succinic acid, benzoic acid, and salicylic acid.

Examples of the phosphorus oxo acid include phosphoric acid, phosphonic acid, and phosphinic acid, with phosphonic acid being especially preferable.

Examples of the phosphorus oxo acid derivative include an ester in which a hydrogen atom of the above-described oxo acid is substituted with a hydrocarbon group. Examples of the hydrocarbon group include an alkyl group having 1 to 5 carbon atoms and an aryl group having 6 to 15 carbon atoms.

Examples of the phosphoric acid derivative include a phosphoric acid ester such as di-n-butyl phosphate and diphenyl phosphate.

Examples of the phosphonic acid derivative include a phosphonic acid ester such as dimethyl phosphonate, di-n-butyl phosphonate, phenylphosphonic acid, diphenyl phosphonate, and dibenzyl phosphonate.

Examples of the phosphinic acid derivative include a phosphinic acid ester and phenylphosphinic acid.

The component (E) may be used alone, or in combination of two or more kinds thereof.

In the case where the component (E) is used, in general, the component (E) is used in an amount in the range of 0.01 part by mass to 5 parts by mass based on 100 parts by mass of the component (A).

Component (F)

For the purpose of imparting water repellency to the resist film, the resist composition (1) may contain a fluorine additive (hereinafter, referred to as "component (F)").

As the component (F), fluorine-containing high-molecular weight compounds disclosed in, for example, JP-A-2010-002870, JP-A-2010-032994, JP-A-2010-277043, JP-A-2011-13569, and JP-A-2011-128226 can be used.

More specifically, examples of the component (F) include a polymer having a constituent unit (f1) represented by the following formula (f1-1). The polymer is preferably a polymer (homopolymer) composed of only the constituent unit (f1) represented by the following formula (f1-1); a copolymer of the constituent unit (f1) and the constituent unit (a1); or a copolymer of the constituent unit (f1), a constituent unit derived from acrylic acid or methacrylic acid, and the constituent unit (a1). Here, the constituent unit (a1) which is copolymerized with the constituent unit (f1) is preferably a constituent unit derived from 1-ethyl-1-cyclooctyl (meth)acrylate.

[Chemical formula 57]

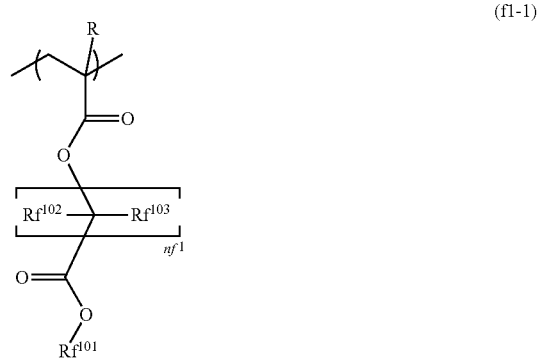

(f1-1)

In the formula, R is the same as that described above; each of $Rf^{102}$ and $Rf^{103}$ independently represents a hydrogen atom, a halogen atom, an alkyl group having 1 to 5 carbon atoms, or a halogenated alkyl group having 1 to 5 carbon atoms, and $Rf^{102}$ and $Rf^{103}$ may be the same as or different from each other; $nf^1$ represents an integer of 1 to 5; and $Rf^{101}$ represents an organic group containing a fluorine atom.

In the formula (f1-1), R which is bonded to the carbon atom at the α-position is the same as that described above. R is preferably a hydrogen atom or a methyl group.

In the formula (f1-1), examples of the halogen atom represented by $Rf^{102}$ and $Rf^{103}$ include a fluorine atom, a chlorine atom, a bromine atom, and an iodine atom, with a fluorine atom being especially preferable. Examples of the alkyl group having 1 to 5 carbon atoms, as represented by $Rf^{102}$ and $Rf^{103}$, include the same groups as those exemplified above for the alkyl group having 1 to 5 carbon atoms, as represented by R. Of these, a methyl group or an ethyl group is preferable. Specifically, examples of the halogenated alkyl group having 1 to 5 carbon atoms, as represented by $Rf^{102}$ and $Rf^{103}$, include a group in which some or all the hydrogen atoms of the above-described alkyl group having 1 to 5 carbon atoms are substituted with a halogen atom. Examples of the halogen atom include a fluorine atom, a chlorine atom, a bromine atom, and an iodine atom, with a fluorine atom being especially preferable. Above all, as $Rf^{102}$ and $Rf^{103}$, a hydrogen atom, a fluorine atom, or an alkyl group having 1 to 5 carbon atoms is preferable, and a hydrogen atom, a fluorine atom, a methyl group, or an ethyl group is more preferable.

In the formula (f1-1), $nf^1$ is an integer of 1 to 5, preferably an integer of 1 to 3, and more preferably 1 or 2.

In the formula (f1-1), $Rf^{101}$ represents an organic group containing a fluorine atom and is preferably a hydrocarbon group containing a fluorine atom.

The hydrocarbon group containing a fluorine atom may be linear, branched, or cyclic, and the number of carbon atoms thereof is preferably 1 to 20, more preferably 1 to 15, and especially preferably 1 to 10.

In addition, in the hydrocarbon group containing a fluorine atom, it is preferable that 25% or more of the hydrogen atoms in the hydrocarbon group are fluorinated; it is more preferable that 50% or more of the hydrogen atoms in the hydrocarbon group are fluorinated; and, it is especially preferable that 60% or more of the hydrogen atoms in the hydrocarbon group are fluorinated in view of the fact that the hydrophobicity of the resist film at the time of immersion exposure is increased.

Above all, $Rf^{101}$ is especially preferably a fluorinated hydrocarbon group having 1 to 5 carbon atoms, and most preferably a trifluoromethyl group, —$CH_2$—$CF_3$, —$CH_2$—$CF_2$—$CF_3$, —$CH(CF_3)_2$, —$CH_2$—$CH_2$—$CF_3$, or —$CH_2$—$CH_2$—$CF_2$—$CF_2$—$CF_3$.

A mass average molecular weight (Mw) (as converted into standard polystyrene by means of gel permeation chromatography) of the component (F) is preferably 1,000 to 50,000, more preferably 5,000 to 40,000, and most preferably 10,000 to 30,000. When the mass average molecular weight of the component (F) is not more than the upper limit value of this range, sufficient solubility in a resist solvent for the use as a resist is exhibited, whereas when it is the lower limit value of this range or more, good dry etching resistance is obtained and the resist pattern has a good cross-sectional shape.

A degree of dispersion (Mw/Mn) of the component (F) is preferably 1.0 to 5.0, more preferably 1.0 to 3.0, and most preferably 1.2 to 2.5.

The component (F) may be used alone, or in combination of two or more kinds thereof.

In the case where the component (F) is used, the component (F) is preferably used in a proportion of 0.5 part by mass to 10 parts by mass based on 100 parts by mass of the component (A).

In the resist composition (1), if desired, miscible additives, for example, an additional resin for improving the performance of the resist film, a dissolution inhibitor, a plasticizer, a stabilizer, a coloring agent, a halation inhibitor, a dye, and the like can be properly added and contained.

Component (S)

The resist composition (1) can be manufactured by dissolving the resist materials in an organic solvent (hereafter, sometimes referred to as "component (S)").

The component (S) may be any organic solvent so long as it is able to dissolve the respective components to be used to give a uniform solution, and any arbitrary one or two or more kinds of organic solvents can be appropriately selected from those which have been conventionally known as solvents for a chemically amplified resist and used.

Examples of the component (S) include a lactone such as γ-butyrolactone; a ketone such as acetone, methyl ethyl ketone (MEK), cyclohexanone, methyl-n-pentyl ketone, methyl isopentyl ketone, and 2-heptanone; a polyhydric alcohol such as ethylene glycol, diethylene glycol, propylene glycol, and dipropylene glycol; a polyhydric alcohol derivative including a compound having an ester bond, such as ethylene glycol monoacetate, diethylene glycol monoacetate, propylene glycol monoacetate, and dipropylene glycol monoacetate, and a compound having an ether bond, such as a monoalkyl ether, (for example, monomethyl ether, monoethyl ether, monopropyl ether, or monobutyl ether) or monophenyl ether of the above-described polyhydric alcohol or the above-described compound having an ester bond [of these, propylene glycol monomethyl ether acetate (PGMEA) or propylene glycol monomethyl ether (PGME) is preferable]; a cyclic ether such as dioxane; an ester such as methyl lactate, ethyl lactate (EL), methyl acetate, ethyl acetate, butyl acetate, methyl pyruvate, ethyl pyruvate, methyl methoxypropionate, and ethyl ethoxypropionate; an aromatic organic solvent such as anisole, ethyl benzyl ether, cresyl methyl ether, diphenyl ether, dibenzyl ether, phenetole, butyl phenyl ether, ethylbenzene, diethylbenzene, pentylbenzene, isopropylbenzene, toluene, xylene, cymene, and mesitylene; and dimethyl sulfoxide (DMSO).

These organic solvents may be used alone, or as a mixed solvent of two or more kinds thereof.

Above all, PGMEA, PGME, γ-butyrolactone, EL, or cyclohexanone is preferable.

In addition, a mixed solvent obtained by mixing PGMEA with a polar solvent is also preferable. Though a blending ratio (mass ratio) of the mixed solvent may be appropriately determined while taking into consideration the compatibility of PGMEA with the polar solvent or the like, it is preferable to allow the blending ratio to fall within the range of 1:9 to 9:1, and more preferably 2:8 to 8:2.

More specifically, in the case where EL or cyclohexanone is blended as the polar solvent, a mass ratio of PGMEA to EL or cyclohexanone is preferably 1:9 to 9:1, and more preferably 2:8 to 8:2. In addition, in the case where PGME is blended as the polar solvent, a mass ratio of PGMEA to PGME is preferably 1:9 to 9:1, more preferably 2:8 to 8:2, and still more preferably 3:7 to 7:3. Furthermore, a mixed solvent of PGMEA, PGME, and cyclohexanone is also preferable.

In addition, as the component (S), besides, a mixed solvent of at least one kind selected from PGMEA and EL with γ-butyrolactone is also preferable. In that case, a mixing proportion is preferably 70:30 to 95:5 in terms of a mass ratio of the former to the latter.

The amount of the component (S) used is not particularly limited, and it is properly set in a concentration at which coating on a substrate or the like can be conducted, according to the thickness of the coating film. In general, the component (S) is used such that the solid content of the resist composition falls within the range of 1 mass % to 20 mass %, and preferably 2 mass % to 15 mass %.

Second Embodiment of Resist Composition

A resist composition of the second embodiment (hereinafter, this resist composition will also be referred to as "resist composition (2)") contains a base material component which generates an acid upon exposure and exhibits changed solubility in a developing solution by the action of the acid, and an acid generator component (B) which generates an acid upon exposure.

Base Material Component

In the resist composition (2), the base material component contains a high-molecular weight compound (hereinafter, this high-molecular weight compound will also be referred to as "component (A2)") having a constituent unit (a0) represented by the general formula (a0-1) and a constituent unit (a15) including a partial structure represented by the general formula (a0-r-1).

Component (A2):

The component (A2) is a high-molecular weight compound having a constituent unit (a0) represented by the general formula (a0-1) and a constituent unit (a15) including a partial structure represented by the general formula (a0-r-1).

Constituent Unit (a0)

The constituent unit (a0) is the same as the above-described constituent unit (a0).

The constituent unit (a0) is preferably at least one kind selected from the group consisting of constituent units represented by the general formulae (a0-r-1), (a0-1-2), and (a0-1-3), respectively, more preferably at least one kind selected from the group consisting of constituent units represented by the general formulae (a0-r-1) and (a0-1-2), respectively, and especially preferably a constituent unit represented by the general formula (a0-r-2), since both a roughness decreasing effect and an exposure margin improving effect are easily obtained.

Specifically, constituent units represented by the formulae (a0-r-212), (a0-1-214), (a0-1-219), (a0-1-220), and (a0-1-221), respectively, are preferable. Of these, constituent units represented by the formulae (a0-r-212) and (a0-1-214), respectively, are more preferable, and a constituent unit represented by the formula (a0-r-214) is especially preferable.

The constituent unit (a0) which the component (A2) has may be either one kind or two or more kinds.

A proportion of the constituent unit (a0) in the component (A2) is preferably 1 mol % to 35 mol %, more preferably 5 mol % to 30 mol %, still more preferably 5 mol % to 25 mol %, and especially preferably 10 mol % to 20 mol % relative to a total sum of all of the constituent units constituting the component (A2).

When the proportion of the constituent unit (a0) is not more than the preferred upper limit value, high sensitivity is maintained and a resist pattern having a good shape is easily obtained. On the other hand, when the proportion of the constituent unit (a0) is the preferred lower limit value or more, sensitivity increases and lithography properties such as resolution and an exposure margin (EL margin) are also enhanced.

Constituent Unit (a15)

In the resist composition (2), the constituent unit (a15) is a constituent unit including a partial structure represented by the general formula (a0-r-1).

The constituent unit (a15) is not particularly limited so long as it is a constituent unit including the partial structure. Preferred examples thereof include a constituent unit represented by the following general formula (a15-1).

[Chemical formula 58]

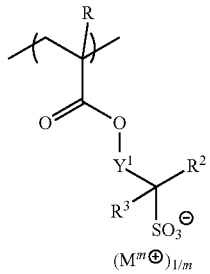

(a15-1)

In the formula, R represents a hydrogen atom, an alkyl group having 1 to 5 carbon atoms, or a halogenated alkyl group having 1 to 5 carbon atoms; $Y^1$ represents a divalent linking group; each of $R^2$ and $R^3$ independently represents a group having 0 to 20 carbon atoms, which is not a fluorine atom, and either $R^2$ or $R^3$ may form a ring with $Y^1$; m represents an integer of 1 or more; and $M^{m+}$ represents an m-valent organic cation.

Anion Moiety of Constituent Unit (a15):

In the formula (a15-1), the alkyl group having 1 to 5 carbon atoms in R is preferably a linear or branched alkyl group having 1 to 5 carbon atoms, and specifically, examples thereof include a methyl group, an ethyl group, a propyl group, an isopropyl group, an n-butyl group, an isobutyl group, a tert-butyl group, a pentyl group, an isopentyl group, and a neopentyl group.

The halogenated alkyl group having 1 to 5 carbon atoms is a group in which some or all hydrogen atoms of the above-described "alkyl group having 1 to 5 carbon atoms in R" are substituted with a halogen atom. Examples of the halogen atom include a fluorine atom, a chlorine atom, a bromine atom, and an iodine atom, with a fluorine atom being especially preferable.

R is preferably a hydrogen atom, an alkyl group having 1 to 5 carbon atoms, or a fluorinated alkyl group having 1 to 5 carbon atoms, and is especially preferably a hydrogen atom or a methyl group in terms of easiness in industrial availability.

In the formula (a15-1), $Y^1$, $R^2$, and $R^3$ are the same as $Y^1$, $R^2$, and $R^3$ in the formula (a0-r-1), respectively.

In the formula (a15-1), $Y^1$ is preferably an optionally substituted linear or branched aliphatic hydrocarbon group, and more preferably a linear or branched alkylene group having 1 to 5 carbon atoms.

In the formula (a15-1), each of $R^2$ and $R^3$ is preferably a hydrogen atom. Both $R^2$ and $R^3$ are especially preferably a hydrogen atom.

Cation Moiety of Constituent Unit (a15):

In the formula (a15-1), $M^{m+}$ represents an m-valent organic cation and is the same as $M^{m+}$ in the formula (a0-r-1). Above all, a cation moiety $[(M^{m+})_{1/m}]$ is preferably an organic cation represented by the general formula (ca-1), and more preferably each of cations represented by the formulae (ca-1-1) to (ca-1-67), respectively.

Specific examples of the constituent unit represented by the formula (a15-1) are given below. In the formulae, Ra represents a hydrogen atom, a methyl group, or a trifluoromethyl group. $(M^{m+})_{1/m}$ is the same as that described above.

[Chemical formula 59]
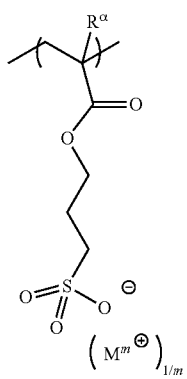 (a15-1-1)
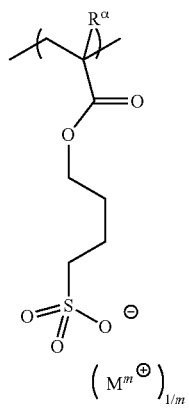 (a15-1-5)
(a15-1-2)
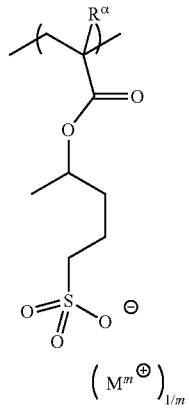 (a15-1-6)
(a15-1-3)
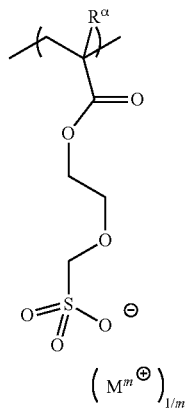 (a15-1-7)
(a15-1-4)
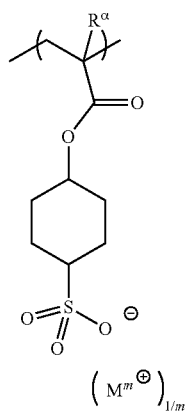 (a15-1-8)

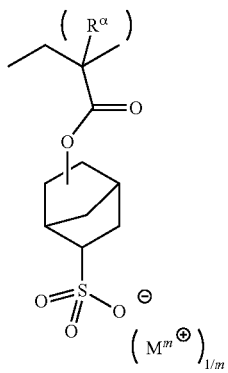

(a15-1-9)

The constituent unit (a15) which the component (A2) has may be either one kind or two or more kinds.

A proportion of the constituent unit (a15) in the component (A2) is preferably 1 mol % to 20 mol %, more preferably 1 mol % to 15 mol %, still more preferably 3 mol % to 15 mol %, and especially preferably 5 mol % to 10 mol % relative to a total sum of all of the constituent units constituting the component (A2).

When the proportion of the constituent unit (a15) is the preferred lower limit value or more, good lithography properties such as, in particular, an improvement of roughness and a good resist pattern shape are easily obtained. On the other hand, when it is not more than the preferred upper limit value, the sensitivity can be maintained at a satisfactory level, and the throughput is also improved.

Other Constituent Units

The component (A2) may further have, in addition to the constituent unit (a0) and the constituent unit (a15), other constituent units.

The foregoing other constituent units are not particularly limited so long as they are a constituent unit which is not classified into the above-described constituent unit (a0) or (a15). A large number of constituent units which have been conventionally known to be used for resins for resist such as those for ArF excimer lasers and KrF excimer lasers (preferably those for ArF excimer lasers), and the like can be used.

In the resist composition (2), the component (A2) preferably further has a constituent unit (a1) which contains an acid decomposable group whose polarity increases by the action of an acid, in addition to the constituent unit (a0) and the constituent unit (a15).

In addition, in the resist composition (2), the component (A2) preferably further has a constituent unit (a2) containing a lactone-containing cyclic group, a —$SO_2$—-containing cyclic group, or a carbonate-containing cyclic group, in addition to the constituent unit (a0), the constituent unit (a15), and the constituent unit (a1).

The component (A2) may have a constituent unit (a3) containing a polar group-containing aliphatic hydrocarbon group, a constituent unit (a4) containing an acid nondissociable aliphatic cyclic group, a constituent unit which generates an acid upon exposure, and the like as other constituent units.

The constituent units (a1), (a2), (a3), and (a4) are the same as the constituent units (a1) to (a4) which the above-described component (A1) may have, respectively.

For example, when the component (A2) has the constituent unit (a1), (a2), (a3), or (a4), the respective constituent units may be used alone, or in combination of two or more kinds thereof.

When the component (A2) has the constituent unit (a1), a proportion of the constituent unit (a1) is preferably 1 mol % to 50 mol %, more preferably 5 mol % to 45 mol %, and still more preferably 5 mol % to 40 mol % relative to a total sum of all of the constituent units constituting the component (A2).

When the proportion of the constituent unit (a1) is the preferred lower limit value or more, a resist pattern can be easily obtained, and thus lithography properties such as sensitivity, resolution, an improvement of roughness, and an EL margin are also enhanced. When the proportion of the constituent unit (a1) is not more than the upper limit value, a balance with other constituent units can be taken.

When the component (A2) has the constituent unit (a2), a proportion of the constituent unit (a2) is preferably 1 mol % to 80 mol %, more preferably 10 mol % to 70 mol %, still more preferably 10 mol % to 65 mol %, and especially preferably 10 mol % to 60 mol % relative to a total sum of all of the constituent units constituting the component (A2).

When the proportion of the constituent unit (a2) is the preferred lower limit value or more, the effects due to the fact that the constituent unit (a2) is contained are sufficiently obtained. When the proportion of the constituent unit (a2) is not more than the preferred upper limit value, a balance with other constituent units can be taken, and various lithography properties and the pattern shape are enhanced.

When the component (A2) has the constituent unit (a3), a proportion of the constituent unit (a3) is preferably 5 mol % to 50 mol %, more preferably 5 mol % to 40 mol %, and still more preferably 5 mol % to 35 mol % relative to a total sum of all of the constituent units constituting the component (A2).

When the proportion of the constituent unit (a3) is the preferred lower limit value or more, the effects due to the fact that the constituent unit (a3) is contained are sufficiently obtained. When the proportion of the constituent unit (a3) is not more than the preferred upper limit value, a balance with other constituent units is easily taken.

When the component (A2) has the constituent unit (a4), a proportion of the constituent unit (a4) is preferably 1 mol % to 30 mol %, and more preferably 3 mol % to 20 mol % relative to a total sum of all of the constituent units constituting the component (A2).

When the proportion of the constituent unit (a4) is the preferred lower limit value or more, the effects due to the fact that the constituent unit (a4) is contained are sufficiently obtained. When the proportion of the constituent unit (a4) is not more than the preferred upper limit value, a balance with other constituent units is easily taken.

In the resist composition (2), the component (A) contains the high-molecular weight compound (A2) having the constituent unit (a0) and the constituent unit (a15), and specific examples of the component (A2) include a high-molecular weight compound composed of a repeating structure of the constituent unit (a0), the constituent unit (a15), the constituent unit (a1), and the constituent unit (a2).

A mass average molecular weight (Mw) (as converted into polystyrene by means of gel permeation chromatography (GPC)) of the component (A2) is not particularly limited, but it is preferably 1,000 to 50,000, more preferably 1,500 to 30,000, and most preferably 2,000 to 20,000.

When the Mw of the component (A2) is not more than the preferred upper limit value of the foregoing range, sufficient solubility in a resist solvent for the use as a resist is exhibited, and when it is the preferred lower limit value of the foregoing range or more, good dry etching resistance is obtained and the resist pattern has a good cross-sectional shape.

A degree of dispersion (Mw/Mn) of the component (A2) is not particularly limited, and is preferably 1.0 to 5.0, more preferably 1.0 to 4.0, and most preferably 1.0 to 3.0. It is to be noted that Mn represents a number average molecular weight.

The component (A2) may be used alone, or in combination of two or more kinds thereof.

A proportion of the component (A2) in the component (A) is preferably 25 mass % or more, more preferably 50 mass % or more, and still more preferably 75 mass % or more relative to a total mass of the component (A), and it may even be 100 mass %. When the proportion is 25 mass % or more, a resist pattern which is excellent in various lithography properties such as an increase of sensitivity and an improvement of roughness is easily formed.

In the resist composition (2), regarding the component (A), a base material component (component (A3)) which does not fall under the definition of the component (A2) and exhibits changed solubility in a developing solution by the action of an acid may be used in combination. The component (A3) is the same as the above-described component (A3), and may be used alone, or in combination of two or more kinds thereof.

In the resist composition (2), the base material component may be used alone, or in combination of two or more kinds thereof.

In the resist composition (2), the content of the base material component may be adjusted in conformity with the thickness of the resist film to be formed, or the like.

Acid Generator Component (B): Component (B)

The acid generator component (B) used in the resist composition (2) is the same as the component (B) used in the resist composition (1).

Other Components

The resist composition (2) may further contain other components in addition to the base material component and the component (B).

Examples of other components include an acid diffusion control agent component; at least one kind of compound (E) selected from the group consisting of an organic carboxylic acid and a phosphorus oxo acid or a derivative thereof; and a fluorine additive.

Examples of the acid diffusion control agent component include the same component (D2) and component (D3) as those which may be used in the resist composition (1).

The compound (E) is the same as the component (E) which may be used in the resist composition (1).

Examples of the fluorine additive include the same component (F) as that which may be used in the resist composition (1).

In addition, in the resist composition (2), if desired, miscible additives, for example, an additional resin for improving the performance of the resist film, a dissolution inhibitor, a plasticizer, a stabilizer, a coloring agent, a halation inhibitor, a dye, and the like can be properly added and contained.

The resist composition (2) can be manufactured by dissolving the resist materials in an organic solvent. As the organic solvent, the same component (S) as that described above can be used in the same manner.

According to the resist composition of the invention, it is possible to form a resist pattern whose roughness is decreased, while maintaining good sensitivity.

In the invention, the resist composition has a partial structure represented by the general formula (a0-r-1) therein. In the partial structure represented by the general formula (a0-r-1), the anion moiety thereof becomes an appropriate weakly acidic anion upon exposure to exhibit a quenching (acid diffusion control) effect to thus trap the acid generated upon exposure. Accordingly, in the formation of a resist pattern, the diffusion of the acid generated upon exposure is suppressed and the roughness of the resist pattern is thus decreased. In addition, even when a component having the partial structure is different from the base material component, the partial structure has a polar group (carbonyloxy group —C(=O)—O—), and thus an interaction acts between the component having the partial structure and the base material component and uniform distribution easily occurs in the resist film. However, when the blending amount of the component having the partial structure is large, sensitivity tends to decrease.

In the invention, the resist composition contains a high-molecular weight compound which has a partial structure represented by the general formula (a0-r-1) and has a constituent unit (a0) having an imide group in a side chain. Due to the combination of the partial structure with the constituent unit (a0), a significant roughness decreasing effect is obtained in the formation of a resist pattern and a decrease of sensitivity is suppressed. Thus, good sensitivity is maintained.

Furthermore, in the formation of a resist pattern using the resist composition of the invention, an exposure margin (EL margin) as an index of a variation in pattern size associated with a fluctuation of the exposure amount, which is difficult to balance with a decrease of roughness, is good.

Resist Pattern Forming Method

A resist pattern forming method of a second aspect of the invention includes a step of forming a resist film on a support using a resist composition of the first aspect of the invention, a step of exposing the resist film, and a step of developing the resist film after the exposure to form a resist pattern.

For example, the resist pattern forming method of this aspect can be performed as follows.

First, the resist composition according to the first aspect is applied to a support using a spinner or the like, and a baking (post applied bake (PAB)) treatment is conducted under a temperature condition of, for example, 80° C. to 150° C. for 40 to 120 seconds, and preferably 60 to 90 seconds, thereby forming a resist film.

Subsequently, using an exposure apparatus, for example, an ArF exposure apparatus, an electron beam drawing apparatus, or an EUV exposure apparatus, the resist film is exposed through a mask having a predetermined pattern formed thereon (mask pattern) or selectively exposed without using a mask pattern by drawing by means of direct irradiation with electron beams, or the like. Then, a baking (post exposure bake (PEB)) treatment is conducted under a temperature condition of, for example, 80° C. to 150° C. for 40 to 120 seconds, and preferably 60 to 90 seconds.

Subsequently, the resist film is subjected to a development treatment. In the case of an alkali development process, an alkali developing solution is used to perform the development treatment, and in the case of a solvent development process, a developing solution containing an organic solvent (organic developing solution) is used to perform the development treatment.

After the development treatment, a rinse treatment is preferably performed. In the rinse treatment, in the case of an alkali development process, water rinsing using pure water is preferable, and in the case of a solvent development process, a rinse solution containing an organic solvent is preferably used.

In the case of the solvent development process, after the development treatment or the rinse treatment, a treatment of removing the developing solution or rinse solution deposited on the pattern with a supercritical fluid may be conducted.

After the development treatment or the rinse treatment, drying is performed. In some cases, a baking treatment (post-baking) may be conducted after the development treatment. In this manner, a resist pattern can be obtained.

The support is not particularly limited, and a conventionally known support can be used. For example, substrates for electronic components, and such substrates having a prescribed wiring pattern formed thereon can be exemplified. More specifically, examples thereof include a metal-made substrate such as silicon wafer, copper, chromium, iron, and aluminum, and a glass substrate. As a material for the wiring pattern, for example, copper, aluminum, nickel, or gold can be used.

In addition, as the support, a support in which an inorganic and/or organic film is provided on the above-described substrate may also be used. Examples of the inorganic film include an inorganic antireflection film (inorganic BARC). Examples of the organic film include an organic film such as an organic antireflection film (organic BARC) and a lower layer organic film in the multilayer resist method.

Here, the multilayer resist method is a method in which at least one layer of an organic film (lower layer organic film) and at least one layer of a resist film (upper layer resist film) are provided on a substrate, and the lower layer organic film is subjected to patterning while using, as a mask, a resist pattern formed on the upper layer resist film, and it is said that a pattern with a high aspect ratio can be formed. That is, according to the multilayer resist method, since a required thickness can be ensured by the lower layer organic film, the resist film can be made thin, so that it becomes possible to form a fine pattern with a high aspect ratio.

Basically, the multilayer resist method is classified into a method of forming a double-layer structure of an upper layer resist film and a lower layer organic film (double-layer resist method), and a method of forming a multilayer structure of three or more layers, in which one or more interlayers (for example, a thin metal film) are provided between an upper layer resist film and a lower layer organic film (triple-layer resist method).

The wavelength to be used for the exposure is not particularly limited, and the exposure can be conducted using radiation such as ArF excimer lasers, KrF excimer lasers, $F_2$ excimer lasers, extreme ultraviolet rays (EUV), vacuum ultraviolet rays (VUV), electron beams (EB), X rays, and soft X rays. The resist composition is high in usefulness for KrF excimer lasers, ArF excimer lasers, EB, or EUV, and is especially useful for ArF excimer lasers, EB, or EUV.

The method of exposing the resist film may be conducted by means of general exposure (dry exposure) which is conducted in air or an inert gas such as nitrogen, or it may be conducted by means of liquid immersion lithography.

The liquid immersion lithography is an exposure method in which a region between a resist film and a lens located at the lowermost position of an exposure apparatus is filled in advance with a solvent (liquid immersion medium) having a refractive index larger than a refractive index of air, and the exposure (immersion exposure) is conducted in that state.

The liquid immersion medium is preferably a solvent having a refractive index larger than a refractive index of air and smaller than a refractive index of a resist film to be exposed. The refractive index of such a solvent is not particularly limited so long as it falls within the foregoing range.

Examples of the solvent having a refractive index larger than a refractive index of air and smaller than a refractive index of the resist film include water, a fluorine-based inert liquid, a silicon-based solvent, and a hydrocarbon-based solvent.

Specific examples of the fluorine-based inert liquid include a liquid composed mainly of a fluorine-based compound such as $C_3HCl_2F_5$, $C_4F_9OCH_3$, $C_4F_9OC_2H_5$, and $C_5H_3F_7$. Of these, fluorine-based inert liquids having a boiling point of 70° C. to 180° C. are preferable, and those having a boiling point of 80° C. to 160° C. are more preferable. A fluorine-based inert liquid having a boiling point falling within the foregoing range is preferable because after completion of the exposure, the removal of the medium used for the liquid immersion can be conducted by a simple method.

As the fluorine-based inert liquid, in particular, a perfluoroalkyl compound in which all of hydrogen atoms of an alkyl group are substituted with a fluorine atom is preferable. Specifically, examples of the perfluoroalkyl compound include a perfluoroalkylether compound and a perfluoroalkylamine compound.

Furthermore, specifically, examples of the perfluoroalkylether compound include perfluoro(2-butyl-tetrahydrofuran) (boiling point: 102° C.), and examples of the perfluoroalkylamine compound include perfluorotributylamine (boiling point: 174° C.).

As the liquid immersion medium, water is preferably used from the viewpoints of cost, safety, environmental issue, and versatility.

Examples of the alkali developing solution used in the development treatment in the alkali development process include a 0.1 mass % to 10 mass % aqueous solution of tetramethylammonium hydroxide (TMAH).

The organic solvent which is contained in an organic developing solution used in the development treatment in the solvent development process may be an organic solvent capable of dissolving the component (A) (component (A) before the exposure) therein, and it can be properly selected among known organic solvents. Specifically, examples thereof include a hydrocarbon-based solvent and a polar solvent such as a ketone-based solvent, an ester-based solvent, an alcohol-based solvent, a nitrile-based solvent, an amide-based solvent, and an ether-based solvent.

The ketone-based solvent is an organic solvent containing C—C(=O)—C in a structure thereof. The ester-based solvent is an organic solvent containing C—C(=O)—O—C in a structure thereof. The alcohol-based solvent is an organic solvent containing an alcoholic hydroxyl group in a structure thereof, and the term "alcoholic hydroxyl group" means a hydroxyl group bonded to a carbon atom of an aliphatic hydrocarbon group. The nitrile-based solvent is an organic solvent containing a nitrile group in a structure thereof. The amide-based solvent is an organic solvent containing an amide group in a structure thereof. The ether-based solvent is an organic solvent containing C—O—C in a structure thereof.

Among organic solvents, there is also present an organic solvent containing plural kinds of functional groups which characterize the above-described respective solvents, in a structure thereof. In that case, the organic solvent is thought to fall under the definition of any solvent species containing a functional group which this organic solvent has. For example, diethylene glycol monomethyl ether falls under the definition of any of the alcohol-based solvent or the ether-based solvent in the above-described classification.

The hydrocarbon-based solvent is a hydrocarbon solvent which is composed of a hydrocarbon which may be halogenated and does not have a substituent other than the halogen atom. Examples of the halogen atom include a fluorine atom, a chlorine atom, a bromine atom, and an iodine atom, with a fluorine atom being preferable.

Above all, the organic solvent which is contained in an organic developing solution is preferably a polar solvent, and preferred examples thereof include a ketone-based solvent, an ester-based solvent, and a nitrile-based solvent.

Specific examples of the ketone-based solvent include 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetyl carbinol, acetophenone, methyl naphthyl ketone, isophorone, propylene carbonate, γ-butyrolactone, and methyl amyl ketone (2-heptanone).

The ketone-based solvent is preferably methyl amyl ketone (2-heptanone).

Examples of the ester-based solvent include methyl acetate, butyl acetate, ethyl acetate, isopropyl acetate, amyl acetate, isoamyl acetate, ethyl methoxyacetate, ethyl ethoxyacetate, propylene glycol monomethyl ether acetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monoethyl ether acetate, diethylene glycol monophenyl ether acetate, diethylene glycol monobutyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monomethyl ether acetate, propylene glycol monoethyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, methyl 2-hydroxypropionate, ethyl 2-hydroxypropionate, methyl 3-methoxypropionate, ethyl 3-methoxypropionate, ethyl 3-ethoxypropionate, and propyl 3-methoxypropionate.

The ester-based solvent is preferably butyl acetate.

Examples of the nitrile-based solvent include acetonitrile, propionitrile, valeronitrile, and butyronitrile.

If desired, the organic developing solution can be blended with a known additive. Examples of the additive include a surfactant. Though the surfactant is not particularly limited, for example, an ionic or nonionic fluorine-based and/or silicon-based surfactant can be used. The surfactant is preferably a nonionic surfactant, and is more preferably a fluorine-based surfactant or a silicon-based surfactant.

In the case of blending the surfactant, the blending amount thereof is usually 0.001 mass % to 5 mass %, preferably 0.005 mass % to 2 mass %, and more preferably 0.01 mass % to 0.5 mass % relative to the whole amount of the organic developing solution.

It is possible to carry out the development treatment through a known development method. Examples of the development treatment include a method of immersing a support in a developing solution for a certain period of time (dip method); a method of raising a developing solution on the surface of a support due to a surface tension and making it stationary for a certain period of time (puddle method); a method of spraying a developing solution onto the surface of a support (spray method); and a method of continuously dispensing a developing solution onto a support rotating at a fixed rate while scanning a developing solution dispense nozzle at a fixed rate (dynamic dispense method).

As the organic solvent contained in the rinse solution which is used in the rinse treatment after the development treatment in the solvent development process, among the organic solvents exemplified above for the organic solvent which is used in the organic developing solution, an organic solvent which hardly dissolves the resist pattern can be properly selected and used. In general, at least one kind of solvent selected from a hydrocarbon-based solvent, a ketone-based solvent, an ester-based solvent, an alcohol-based solvent, an amide-based solvent, and an ether-based solvent is used. Of these, at least one kind selected from a hydrocarbon-based solvent, a ketone-based solvent, an ester-based solvent, an alcohol-based solvent, and an amide-based solvent is preferable; at least one kind selected from an alcohol-based solvent and an ester-based solvent is more preferable; and an alcohol-based solvent is especially preferable.

The alcohol-based solvent which is used in the rinse solution is preferably a monohydric alcohol having 6 to 8 carbon atoms, and the monohydric alcohol may be linear, branched, or cyclic. Specifically, examples thereof include 1-hexanol, 1-heptanol, 1-octanol, 2-hexanol, 2-heptanol, 2-octanol, 3-hexanol, 3-heptanol, 3-octanol, 4-octanol, and benzyl alcohol. Of these, 1-hexanol, 2-heptanol, or 2-hexanol is preferable, and 1-hexanol or 2-hexanol is more preferable.

These organic solvents may be used alone, or as a mixture of two or more kinds thereof. In addition, such an organic solvent may be mixed with an organic solvent other than the foregoing organic solvents or water and used. However, taking into consideration the development properties, an amount of water blended in the rinse solution is preferably not more than 30 mass %, more preferably not more than 10 mass %, still more preferably not more than 5 mass %, and especially preferably not more than 3 mass % relative to the whole amount of the rinse solution.

The rinse solution can be blended with a known additive, if desired. Examples of the additive include a surfactant. Examples of the surfactant include the same surfactants as those described above. Above all, a nonionic surfactant is preferable, and a fluorine-based surfactant or a silicon-based surfactant is more preferable.

In the case of blending the surfactant, the blending amount thereof is usually 0.001 mass % to 5 mass %, preferably 0.005 mass % to 2 mass %, and more preferably 0.01 mass % to 0.5 mass % relative to the whole amount of the rinse solution.

The rinse treatment (washing treatment) using a rinse solution can be carried out through a known rinse method. Examples of the method include a method of continuously dispensing a rinse solution onto a support rotating at a fixed rate (rotary coating method); a method of immersing a support in a rinse solution for a certain period of time (dip method); and a method of spraying a rinse solution onto the surface of a support (spray method).

EXAMPLES

The invention is hereunder described in more detail by reference to the following Examples, but it should not be construed that the invention is limited to these Examples.

In Examples, a compound represented by a chemical formula (1) is designated as "compound (1)", and the same applies for compounds represented by other chemical formulae.

Examples of Manufacturing of High-Molecular Weight Compound

In Examples, to obtain a high-molecular weight compound used as a base material component, compounds as monomers represented by the following chemical formulae were used in combination in a predetermined molar ratio and copolymerized through a known radical polymerization method.

[Chemical formula 60]

(21)
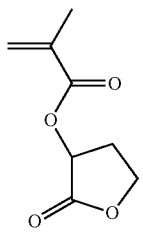

(11)
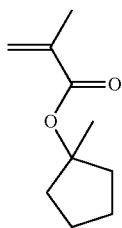

(31)
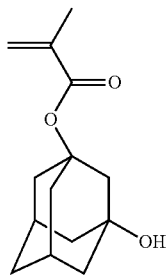

(151)
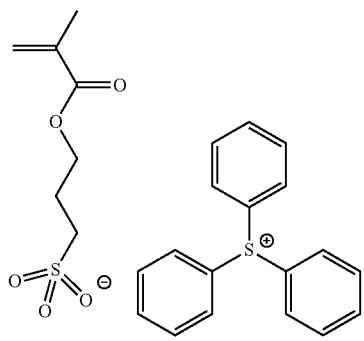

(01)
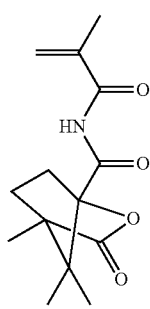

(02)
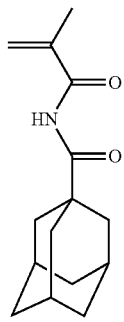

(03)
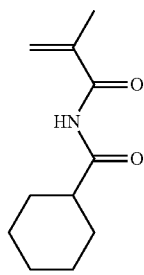

(04)
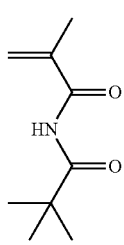

High-Molecular Weight Compounds 1 to 9

Regarding obtained high-molecular weight compounds 1 to 9, a monomer composition ratio of the high-molecular weight compound obtained by means of $^{13}$C-NMR (a proportion (molar ratio) of each constituent unit in a structure), a mass average molecular weight (Mw) as converted into standard polystyrene determined through GPC measurement, and a degree of molecular weight dispersion (Mw/Mn) are recorded together in Table 1.

TABLE 1

| High-molecular weight compound | Compound (molar ratio) | | | | | | | | Mw | Mw/Mn |
|---|---|---|---|---|---|---|---|---|---|---|
| | (21) | (11) | (01) | (02) | (03) | (04) | (31) | (151) | | |
| 1 | 45 | 35 | 20 | | | | | | 6800 | 1.6 |
| 2 | 45 | 35 | | 20 | | | | | 6500 | 1.6 |
| 3 | 50 | 30 | 20 | | | | | | 6600 | 1.6 |
| 4 | 50 | 40 | 10 | | | | | | 6900 | 1.6 |
| 5 | 50 | 35 | 15 | | | | | | 6800 | 1.6 |
| 6 | 41 | 31 | 18 | | | | | 10 | 7000 | 1.7 |
| 7 | 45 | 35 | | | 20 | | | | 7000 | 1.6 |
| 8 | 45 | 35 | | | | 20 | | | 6900 | 1.6 |
| 9 | 45 | 35 | | | | | 20 | | 6900 | 1.6 |

Preparation of Resist Composition

Examples 1 to 14 and Comparative Examples 1 to 4

A resist composition of each of Examples and Comparative Examples was prepared by mixing and dissolving the respective components shown in Table 2.

TABLE 2

| | Component (A) | Component (B) | Component (D) | Molar ratio (D)/(B) | Component (F) | Component (S) |
|---|---|---|---|---|---|---|
| Example 1 | (A)-1 [100] | (B)-1 [14.0] | (D1)-1 [5.3] | 0.4 | (F)-1 [3.0] | (S)-1 [3200] |
| Example 2 | (A)-1 [100] | (B)-1 [14.0] | (D1)-1 [8.0] | 0.6 | (F)-1 [3.0] | (S)-1 [3200] |
| Example 3 | (A)-1 [100] | (B)-1 [10.0] | (D1)-1 [9.5] | 1.0 | (F)-1 [3.0] | (S)-1 [3200] |
| Example 4 | (A)-1 [100] | (B)-1 [7.0] | (D1)-1 [8.0] | 1.2 | (F)-1 [3.0] | (S)-1 [3200] |
| Example 5 | (A)-1 [100] | (B)-1 [14.0] | (D1)-2 [7.7] | 0.6 | (F)-1 [3.0] | (S)-1 [3200] |
| Example 6 | (A)-1 [100] | (B)-1 [10.0] | (D1)-2 [9.2] | 1.0 | (F)-1 [3.0] | (S)-1 [3200] |
| Example 7 | (A)-1 [100] | (B)-1 [7.0] | (D1)-2 [7.7] | 1.2 | (F)-1 [3.0] | (S)-1 [3200] |
| Example 8 | (A)-2 [100] | (B)-1 [14.0] | (D1)-1 [8.0] | 0.6 | (F)-1 [3.0] | (S)-1 [3200] |
| Example 9 | (A)-3 [100] | (B)-1 [14.0] | (D1)-1 [8.0] | 0.6 | (F)-1 [3.0] | (S)-1 [3200] |
| Example 10 | (A)-4 [100] | (B)-1 [14.0] | (D1)-1 [8.0] | 0.6 | (F)-1 [3.0] | (S)-1 [3200] |
| Example 11 | (A)-5 [100] | (B)-1 [14.0] | (D1)-1 [8.0] | 0.6 | (F)-1 [3.0] | (S)-1 [3200] |
| Example 12 | (A)-6 [100] | (B)-1 [14.0] | — | — | (F)-1 [3.0] | (S)-1 [3200] |
| Example 13 | (A)-7 [100] | (B)-1 [14.0] | (D1)-1 [8.0] | 0.6 | (F)-1 [3.0] | (S)-1 [3200] |
| Example 14 | (A)-8 [100] | (B)-1 [14.0] | (D1)-1 [8.0] | 0.6 | (F)-1 [3.0] | (S)-1 [3200] |
| Comparative Example 1 | (A)-1 [100] | (B)-1 [14.0] | (D2)-1 [4.6] | 0.4 | (F)-1 [3.0] | (S)-1 [3200] |
| Comparative Example 2 | (A)-9 [100] | (B)-1 [14.0] | (D2)-1 [4.6] | 0.4 | (F)-1 [3.0] | (S)-1 [3200] |
| Comparative Example 3 | (A)-1 [100] | (B)-1 [14.0] | (D2)-2 [4.4] | 0.4 | (F)-1 [3.0] | (S)-1 [3200] |
| Comparative Example 4 | (A)-1 [100] | (B)-1 [14.0] | (D3)-1 [1.4] | 0.4 | (F)-1 [3.0] | (S)-1 [3200] |

In Table 2, the respective symbols have the following meanings. The numerical values in the square brackets represent a blending amount (parts by mass).

The term "molar ratio (D)/(B)" refers to a mixing ratio of the component (D) (component (D1), component (D2), or component (D3)) to the component (B) contained in the resist composition, that is, a proportion (molar ratio) of the content of the component (D) to the content of the component (B).

(A)-1 to (A)-9: The above-described high-molecular weight compounds 1 to 9.

(B)-1: An acid generator formed of a compound represented by the following chemical formula (B)-1.

(D1)-1 and (D1)-2: Compounds represented by the following chemical formulae (D1)-1 and (D1)-2, respectively.

(D2)-1 and (D2)-2: Photodegradable bases composed of compounds represented by the following chemical formulae (D2)-1 and (D2)-2, respectively.

(D3)-1: Triethanolamine (F)-1: A fluorine-containing high-molecular weight compound represented by the following chemical formula (F)-1. A mass average molecular weight (Mw) as converted into standard polystyrene determined through GPC measurement is 25,000, and a degree of molecular weight dispersion (Mw/Mn) is 2.0.

(S)-1: A mixed solvent of propylene glycol monomethyl ether acetate/propylene glycol monomethyl ether/cyclohexanone=45/30/25 (mass ratio).

[Chemical formula 61]

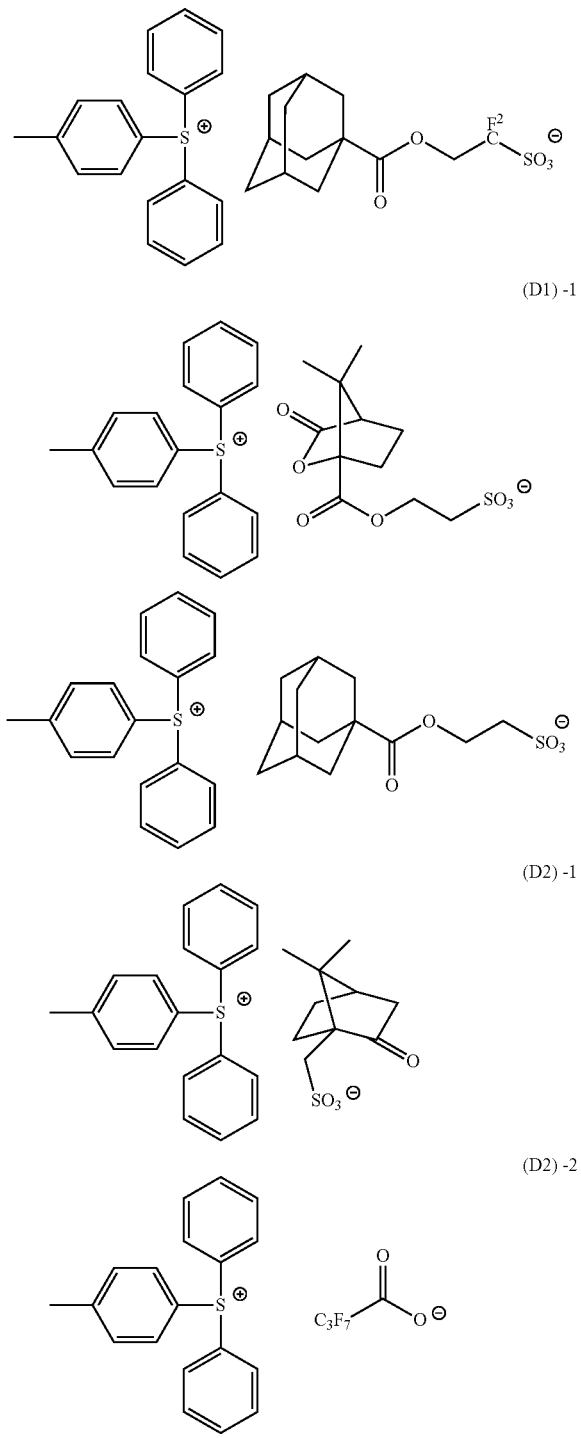
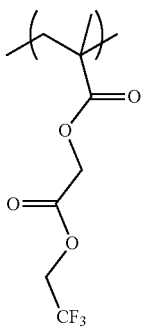

Using the obtained resist compositions, resist patterns were formed, and sensitivity, line wise roughness (LWR), and an exposure margin (EL margin) thereof were evaluated as follows.

Formation of Resist Pattern

An organic antireflection film composition "ARC95" (product name, manufactured by Brewer Science Ltd.) was applied onto an 12-inch silicon wafer using a spinner, and the composition was then baked and dried at 205° C. for 60 seconds on a hotplate, thereby forming an organic antireflection film having a thickness of 90 nm.

Then, each of the resist compositions of Examples and Comparative Examples was applied onto the organic antireflection film using a spinner, and was then prebaked (PAB) and dried on a hotplate at a temperature of 110° C. for 60 seconds, thereby forming a resist film having a thickness of 90 nm.

Subsequently, using an ArF exposure apparatus for liquid immersion, NSR-S609B (manufactured by Nikon Corporation; numerical aperture (NA)=1.07, Dipole 0.97/0.78 with polano, liquid immersion medium: water), the resist film was selectively irradiated with ArF excimer lasers (193 nm) through a binary mask.

Thereafter, a post-exposure baking (PEB) treatment was conducted at a temperature of 95° C. for 60 seconds.

Next, alkali development was performed for 10 seconds at 23° C. in a 2.38 mass % aqueous solution of TMAH (product name: NMD-3, manufactured by Tokyo Ohka Kogyo Co., Ltd.), and then the resist film was water-rinsed for 30 seconds using pure water, followed by drying by shaking.

As a result, in each of Examples and Comparative Examples, a 1:1 line-and-space (LS) pattern having a line width of 50 nm and a pitch of 100 nm was formed.

In the formation of the resist pattern in each of Examples and Comparative Examples, an optimum exposure amount (sensitivity) Eop (mJ/cm$^2$) at which the LS pattern was formed was determined. The results are shown in Table 3.

Evaluation of Line Wise Roughness (LWR)

In the LS pattern formed through the above-described "formation of resist pattern", a space width was measured at 400 places in a longitudinal direction of the space using a measuring scanning electron microscope (SEM) (accelerating voltage: 300 V, product name: S-9380, manufactured by Hitachi High-Technologies Corporation). From the results thereof, a value (3s) three times larger than a standard deviation (s) was obtained, and an average value (nm) of 3s at 400 places was calculated as a measure of LWR. The results thereof are shown in Table 3.

The smaller the value of 3s, the less the roughness of the line width, and it means that a LS pattern having a more uniform width is obtained.

Evaluation of Exposure Margin (EL Margin)

An exposure amount at which the LS pattern was formed to have a line width within the range of ±5% (47.5 nm to 52.5 nm) of the target size (line width: 50 nm) through the above-described "formation of resist pattern" was obtained, and an EL margin (unit: %) was obtained through the following expression. The results thereof are shown in Table 3.

EL margin(%)=(|E1−E2|/Eop)×100

E1: An exposure amount (mJ/cm²) in the formation of a LS pattern having a line width of 47.5 nm.

E2: An exposure amount (mJ/cm²) in the formation of a LS pattern having a line width of 52.5 nm.

The EL margin indicates that the larger the value thereof, the smaller the variation in pattern size associated with a fluctuation of the exposure amount.

TABLE 3

|  | Eop (mJ/cm²) | LWR (nm) | EL margin (%) |
|---|---|---|---|
| Example 1 | 12 | 3.3 | 7.9 |
| Example 2 | 14 | 3.2 | 7.8 |
| Example 3 | 16 | 3.1 | 7.8 |
| Example 4 | 18 | 2.9 | 7.9 |
| Example 5 | 15 | 3.2 | 8.0 |
| Example 6 | 17 | 3.0 | 8.2 |
| Example 7 | 20 | 2.8 | 8.1 |
| Example 8 | 14 | 3.3 | 7.9 |
| Example 9 | 14 | 3.1 | 7.9 |
| Example 10 | 14 | 3.0 | 7.9 |
| Example 11 | 14 | 3.2 | 8.0 |
| Example 12 | 18 | 3.1 | 8.4 |
| Example 13 | 14 | 3.4 | 7.8 |
| Example 14 | 12 | 3.5 | 7.7 |
| Comparative Example 1 | 14 | 3.6 | 7.7 |
| Comparative Example 2 | 22 | 3.3 | 7.3 |
| Comparative Example 3 | 14 | 3.4 | 7.5 |
| Comparative Example 4 | 28 | 4.2 | 8.0 |

From the results shown in Table 3, it is possible to confirm that with the resist compositions of Examples 1 to 14 to which the invention is applied, it is possible to form a resist pattern whose roughness is decreased, while maintaining good sensitivity.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A resist composition which generates an acid upon exposure and exhibits changed solubility in a developing solution by the action of the acid, comprising:
a partial structure represented by the following general formula (a0-r-1) bonded to a compound comprising the resist composition or to a base material component (A), the base material component (A) comprising a high-molecular weight compound having a constituent unit (a0) represented by the following general formula (a0-1):

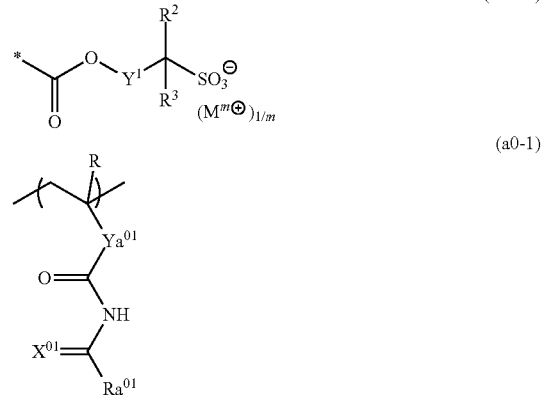

wherein in the formula (a0-r-1), $Y^1$ represents a divalent linking group; each of $R^2$ and $R^3$ independently represents a hydrogen atom, an alkyl group, an alkenyl group, an alkynyl group, an aryl group, a substituted or unsubstituted amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a hydroxy group, a mercapto group, a chlorine atom, a bromine atom, an iodine atom, a cyano group, a sulfo group, a carboxyl group, a nitro group, a hydroxamic acid group, a sulfino group, a hydrazino group, an imino group, a heterocyclic group, a silyl group; or a cyclic hydrocarbon group including an aromatic cyclic hydrocarbon group and an alicyclic hydrocarbon group which may contain a hetero atom in a ring structure thereof, in which some of hydrogen atoms bonded to the carbon atoms constituting the ring structure thereof may be substituted; and when either $R^2$ or $R^3$ is an alkyl group, one hydrogen atom of the alkyl group may be substituted with —C(=O)—O—$R^{11}$ or —O—C(=O)—$R^{11}$, wherein $R^{11}$ represents an optionally substituted hydrocarbon group having 4 to 20 carbon atoms; and either $R^2$ or $R^3$ may form a ring with $Y^1$; m represents an integer of 1 or more; $M^{m+}$ represents an m-valent organic cation; and * represents a bond to the remainder of the compound comprising the resist composition or to the base material component (A), and in the formula (a0-1), R represents a hydrogen atom, an alkyl group having 1 to 5 carbon atoms, or a halogenated alkyl group having 1 to 5 carbon atoms; $Ya^{01}$ represents a single bond or a divalent linking group; $X^{01}$ represents a sulfur atom or an oxygen atom; and $Ra^{01}$ represents an optionally substituted cyclic group, an optionally substituted chain alkyl group, or an optionally substituted chain alkenyl group.

2. The resist composition according to claim 1, wherein the high-molecular weight compound has a constituent unit (a1) which contains an acid decomposable group whose polarity increases by the action of an acid.

3. The resist composition according to claim 2, wherein the high-molecular weight compound further has a constituent unit (a2) containing a lactone-containing cyclic group, a —SO₂—-containing cyclic group, or a carbonate-containing cyclic group.

4. A resist composition according to claim 1, wherein the partial structure represented by the formula (a0-r-1) is selected from the group consisting of:

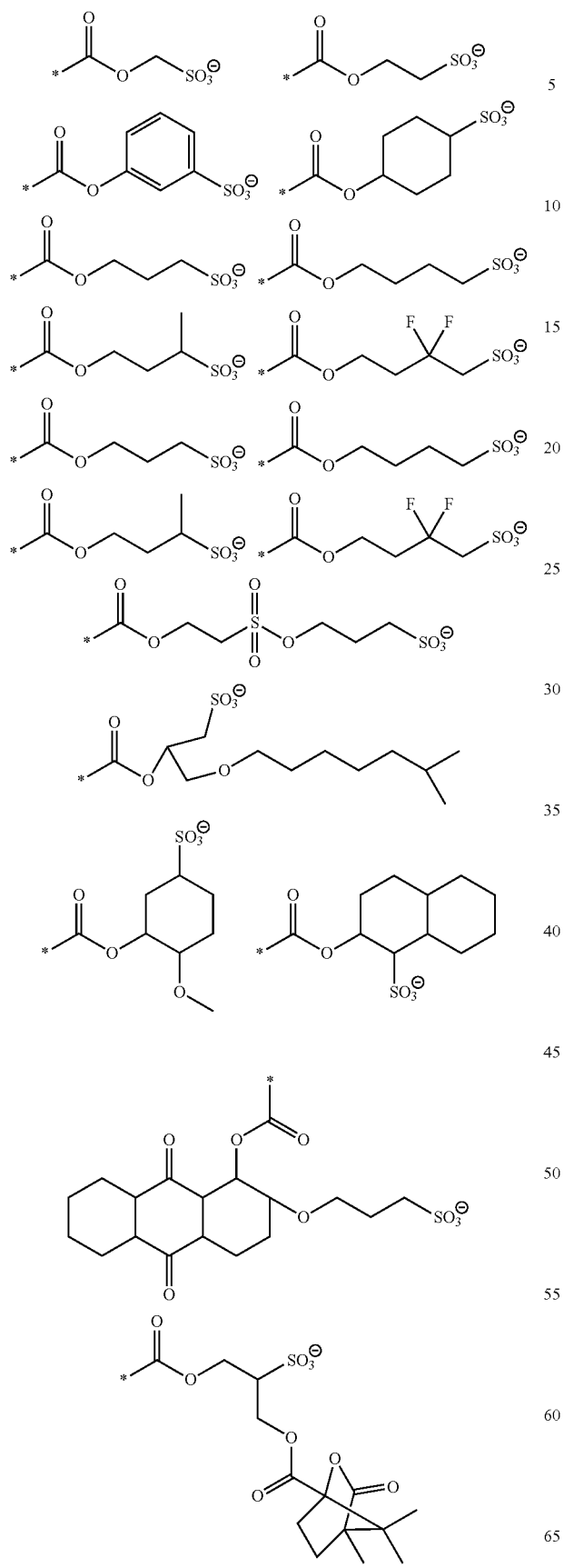

wherein * represents a bond to the remainder of the compound comprising the resist composition or to the base material component (A).

5. A resist composition which generates an acid upon exposure and exhibits changed solubility in a developing solution by the action of the acid, comprising:
  a base material component (A) which exhibits changed solubility in a developing solution by the action of an acid;
  an acid generator component (B) which generates an acid upon exposure; and
  a compound (D1) which includes a partial structure represented by the following general formula (a0-r-1),
  wherein the base material component (A) contains a high-molecular weight compound having a constituent unit (a0) represented by the following general formula (a0-1):

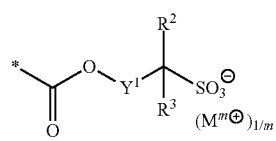

(a0-r-1)

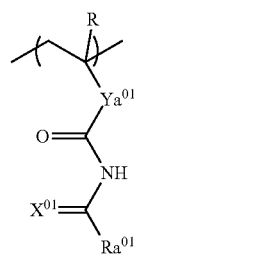

(a0-1)

wherein in the formula (a0-r-1), $Y^1$ represents a divalent linking group; each of $R^2$ and $R^3$ independently represents a hydrogen atom, an alkyl group, an alkenyl group, an alkynyl group, an aryl group, a substituted or unsubstituted amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a hydroxy group, a mercapto group, a chlorine atom, a bromine atom, an iodine atom, a cyano group, a sulfo group, a carboxyl group, a nitro group, a hydroxamic acid group, a sulfino group, a hydrazino group, an imino group, a heterocyclic group, a silyl group; or a cyclic hydrocarbon group including an aromatic cyclic hydrocarbon group and an alicyclic hydrocarbon group which may contain a hetero atom in a ring structure thereof, in which some of hydrogen atoms bonded to the carbon atoms constituting the ring structure thereof may be substituted; and when either $R^2$ or $R^3$ is an alkyl group, one hydrogen atom of the alkyl group may be substituted with —C(=O)—O—$R^{11}$ or —O—C(=O)—$R^{11}$, wherein $R^{11}$ represents an optionally substituted hydrocarbon group having 4 to 20 carbon atoms; and either $R^2$ or $R^3$ may form a ring with $Y^1$; m represents an integer of 1 or more; $M^{m+}$ represents an m-valent organic cation; and * represents a bond to the remainder of the compound (D1), and in the formula (a0-1), R represents a hydrogen atom, an alkyl group having 1 to 5 carbon atoms, or a halogenated alkyl group having 1 to 5 carbon atoms; $Ya^{01}$ represents a single bond or a divalent linking group; $X^{01}$ represents a sulfur atom or an oxygen atom; and $Ra^{01}$ represents an optionally substituted cyclic group, an optionally substituted chain alkyl group, or an optionally substituted chain alkenyl group.

6. The resist composition according to claim 5, wherein the high-molecular weight compound has a constituent unit (a1) which contains an acid decomposable group whose polarity increases by the action of an acid.

7. The resist composition according to claim 6, wherein the high-molecular weight compound further has a constituent unit (a2) containing a lactone-containing cyclic group, a —$SO_2$—-containing cyclic group, or a carbonate-containing cyclic group.

8. A resist composition according to claim 5, wherein the partial structure represented by the formula (a0-r-1) is selected from the group consisting of:

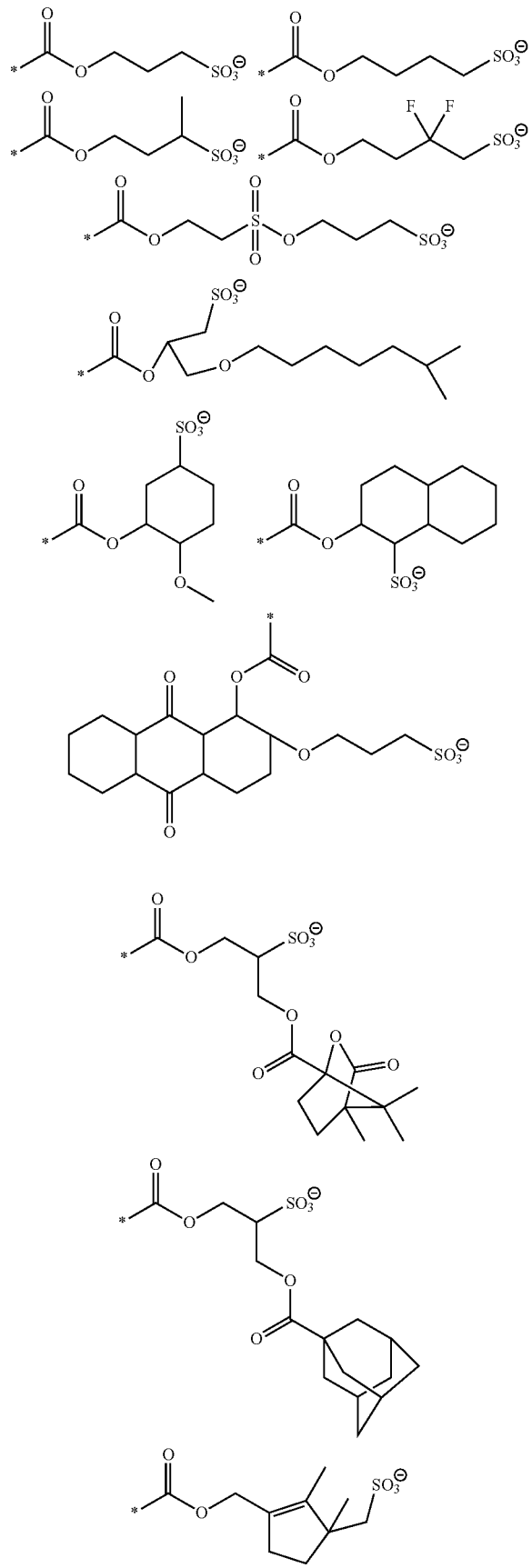

-continued

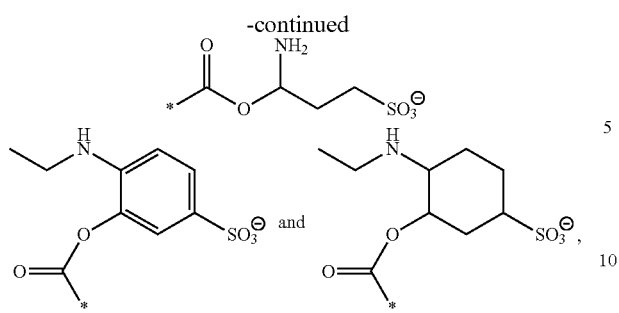

wherein * represents a bond to the remainder of the compound (D1).

9. A resist composition comprising:
a base material component which generates an acid upon exposure and exhibits changed solubility in a developing solution by the action of the acid; and
an acid generator component (B) which generates an acid upon exposure,
wherein the base material component contains a high-molecular weight compound having a constituent unit (a0) represented by the following general formula (a0-1) and a constituent unit (a15) including a partial structure represented by the following general formula (a0-r-1):

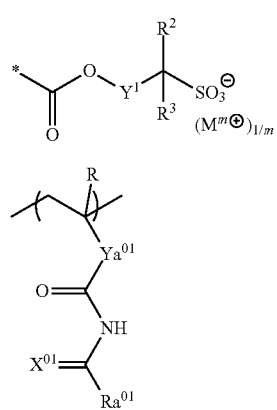

wherein in the formula (a0-r-1), $Y^1$ represents a divalent linking group; each of $R^2$ and $R^3$ independently represents a hydrogen atom, an alkyl group, an alkenyl group, an alkynyl group, an aryl group, a substituted or unsubstituted amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a hydroxy group, a mercapto group, a chlorine atom, a bromine atom, an iodine atom, a cyano group, a sulfo group, a carboxyl group, a nitro group, a hydroxamic acid group, a sulfino group, a hydrazino group, an imino group, a heterocyclic group, a silyl group; or a cyclic hydrocarbon group including an aromatic cyclic hydrocarbon group and an alicyclic hydrocarbon group which may contain a hetero atom in a ring structure thereof, in which some of hydrogen atoms bonded to the carbon atoms constituting the ring structure thereof may be substituted; and when either $R^2$ or $R^3$ is an alkyl group, one hydrogen atom of the alkyl group may be substituted with $-C(=O)-O-R^{11}$ or $-O-C(=O)-R^{11}$, wherein $R^{11}$ represents an optionally substituted hydrocarbon group having 4 to 20 carbon atoms; and either $R^2$ or $R^3$ may form a ring with $Y^1$; m represents an integer of 1 or more; $M^{m+}$ represents an m-valent organic cation; and * represents a bond to the remainder of the constituent unit (a15) in the base material component, and in the formula (a0-1), R represents a hydrogen atom, an alkyl group having 1 to 5 carbon atoms, or a halogenated alkyl group having 1 to 5 carbon atoms; $Ya^{01}$ represents a single bond or a divalent linking group; $X^{01}$ represents a sulfur atom or an oxygen atom; and $Ra^{01}$ represents an optionally substituted cyclic group, an optionally substituted chain alkyl group, or an optionally substituted chain alkenyl group.

10. The resist composition according to claim 9,
wherein the high-molecular weight compound has a constituent unit (a1) which contains an acid decomposable group whose polarity increases by the action of an acid.

11. The resist composition according to claim 10,
wherein the high-molecular weight compound further has a constituent unit (a2) containing a lactone-containing cyclic group, a $-SO_2-$-containing cyclic group, or a carbonate-containing cyclic group.

12. A resist composition according to claim 9,
wherein the partial structure represented by the formula (a0-r-1) is selected from the group consisting of:

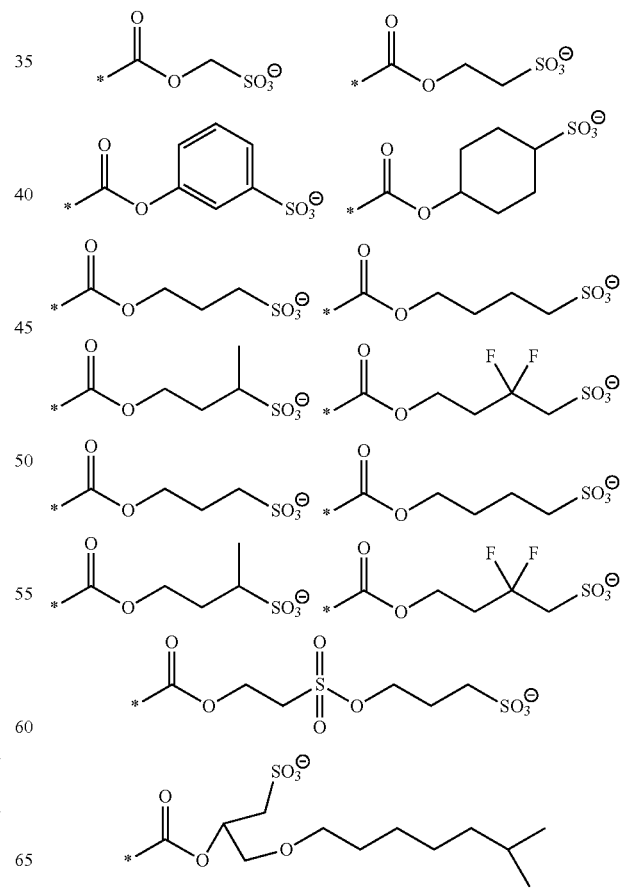

149

-continued

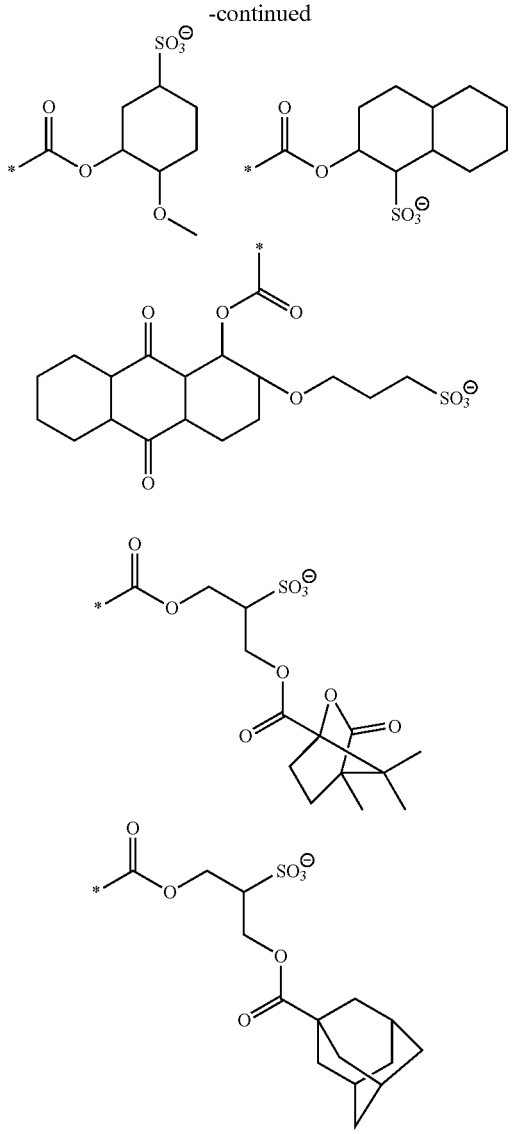

150

-continued

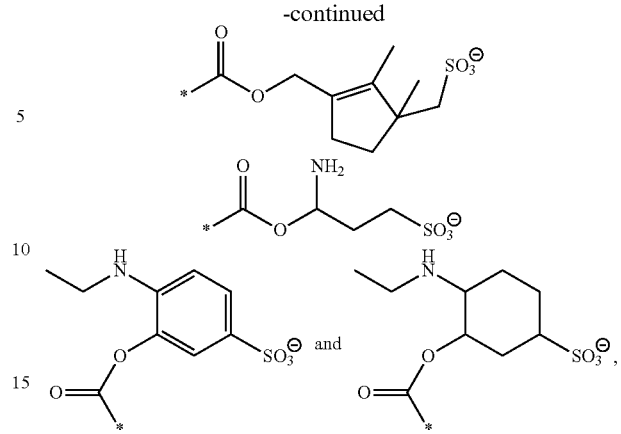

wherein * represents a bond to the remainder of the constituent unit (a15) in the base material component.

13. A resist pattern forming method comprising:

forming a resist film on a support using the resist composition according to claim 1;

exposing the resist film; and developing the resist film after the exposure to form a resist pattern.

14. A resist pattern forming method comprising:

forming a resist film on a support using the resist composition according to claim 5;

exposing the resist film; and developing the resist film after the exposure to form a resist pattern.

15. A resist pattern forming method comprising:

forming a resist film on a support using the resist composition according to claim 9;

exposing the resist film; and developing the resist film after the exposure to form a resist pattern.

* * * * *

UNITED STATES PATENT AND TRADEMARK OFFICE
CERTIFICATE OF CORRECTION

PATENT NO.         : 9,052,592 B2
APPLICATION NO.    : 14/218249
DATED              : June 9, 2015
INVENTOR(S)        : Tsuyoshi Nakamura et al.

Page 1 of 2

It is certified that error appears in the above-identified patent and that said Letters Patent is hereby corrected as shown below:

In the specification

Col. 10, line 57, "Y." should be --$Y^1$.--.
Col. 11, line 35, "7 to 12" should be --2 to 12--.
Col. 13, line 38, "amercapto" should be --a mercapto--.
Col. 16, line 33, "(a0-r-1)" should be --(ca-r-1)--.
Col. 39, line 13, "—$Y^{21}$—O—" should be -- —$Y^{21}$—O—,--.
Col. 39, line 28, "—C(=O)O—$Y^{21}$—," should be -- —C(=O)—O—$Y^{21}$—,--.
Col. 45, line 62, "(a0-r-1)," should be --(a0-1-1),--.
Col. 45, line 66, "(a0-r-1)," should be --(a0-1-1),--.
Col. 46, line 13, "(a0-r-2)," should be --(a0-1-2),--.
Col. 46, line 27, "(a0-r-3)," should be --(a0-1-3),--.
Col. 46, line 33, "(a0-1)" should be --(a0-1).--.
Col. 58, line 47, "(a1-r-1)," should be --(a1-r2-1),--.
Col. 58, line 53, "(a0-r2-2)," should be --(a1-r2-2),--.
Col. 58, line 60, "(a0-r2-2)," should be --(a1-r2-2),--.
Col. 65, line 56, "(a0-r-1)" should be --(a1-r-1)--.
Col. 76, line 47, "(A1)" should be --(A1).--.
Col. 85, line 65, "$Ra^{'15}$" should be --$Ra^{'51}$--.
Col. 104, line 7, "amethylene" should be --a methylene--.
Col. 106, line 32, "(a0-r-1)" to --(ca-r-1)--.
Col. 106, line 54, "$R^{101}$" should be --$R^{101'}$--.
Col. 111, line 51, "$R^{d2}$" should be --$Rd^2$--.
Col. 123, line 28, "(a0-r-1)," should be --(a0-1-1),--.
Col. 123, line 32, "(a0-r-1)" to --(a0-1-1)--.
Col. 123, line 34, "(a0-r-2)," should be --(a0-1-2),--.
Col. 123, line 38, "(a0-r-212)," should be --(a0-1-212),--.
Col. 123, line 40, "(a0-r-212)" should be --(a0-1-212)--.
Col. 123, line 42, "(a0-r-214)" should be --(a0-1-214)--.

Signed and Sealed this
Twenty-second Day of March, 2016

Michelle K. Lee
*Director of the United States Patent and Trademark Office*

CERTIFICATE OF CORRECTION (continued)

In the claims

Col. 144, lines 60-65 (claim 5):

" 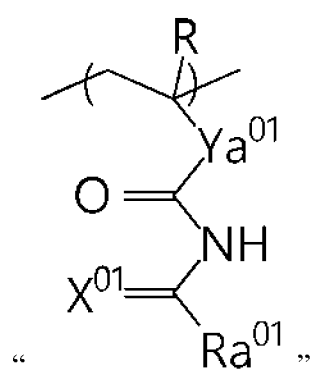 " should be -- 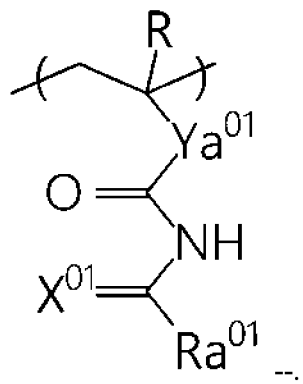 --.

Col. 147, lines 35-45:

" 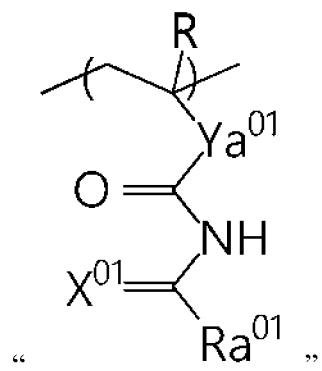 " should be -- 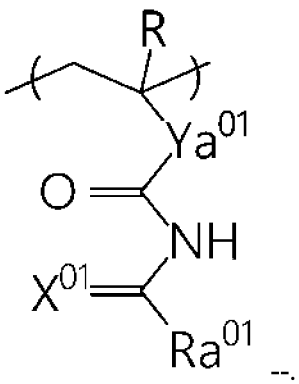 --.

Col. 148, line 20 (claim 10), change "(al)" to --(a1)--.